United States Patent
Dymock et al.

(10) Patent No.: US 6,699,887 B2
(45) Date of Patent: Mar. 2, 2004

(54) ANTI-HIV PYRAZOLE DERIVATIVES

(75) Inventors: Brian William Dymock, St. Albans (GB); Philip Stephen Jones, Welwyn Garden City (GB); John Herbert Merrett, Baldock (GB); Martin John Parratt, Hertford (GB)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/956,656

(22) Filed: Sep. 20, 2001

(65) Prior Publication Data

US 2003/0018197 A1 Jan. 23, 2003

(30) Foreign Application Priority Data

Oct. 10, 2000 (GB) ................................. 0024795

(51) Int. Cl.[7] .................... C07D 231/18; C07D 231/22; C07D 401/12; A61K 31/415; A61D 31/18
(52) U.S. Cl. .................... 514/341; 514/407; 546/276.1; 548/366.1
(58) Field of Search ................ 546/276.1; 514/341, 514/407; 548/366.1

(56) References Cited

U.S. PATENT DOCUMENTS 6,005,109 A    12/1999   Faraci et al.

FOREIGN PATENT DOCUMENTS

| EP | 627423 | 12/1994 |
| WO | 0627423 | * 1/1993 |

* cited by examiner

Primary Examiner—John M. Ford
Assistant Examiner—Hong Liu
(74) Attorney, Agent, or Firm—George W. Johnston; Dennis P. Tramaloni

(57) ABSTRACT

The present invention comprises novel and known pyrazole derivatives having anti-HIV activity, a process for their manufacture, pharmaceutical compositions and the use of such compounds in medicine. In particular, the compounds of formula I are inhibitors of the human immunodeficiency virus reverse transcriptase enzyme which is involved in viral replication. Consequently the compounds of this invention may be advantageously used as therapeutic agents for HIV infection.

11 Claims, No Drawings

ANTI-HIV PYRAZOLE DERIVATIVES

BACKGROUND OF THE INVENTION

The present invention relates to methods and compounds for the treatment of HIV infection. The disease Acquired Immunodeficiency Syndrome (AIDS) is the end result of infection by the distinct retroviruses, human immunodeficiency virus type-1 (HIV-1) or type-2 (HIV-2). Several critical points in the virus life cycle have been identified as possible targets for therapeutic intervention. Inhibition of one of these, the transcription of viral RNA to viral DNA (reverse transcriptase, RT), has provided a number of the current therapies used in treating AIDS. Inhibition of reverse transcriptase provided the first form of treatment for HIV infection with 3'-azido-3'-deoxythymidine (AZT). Since then several inhibitors have been launched, broadly forming two classes: nucleoside analogues and non-nucleosides. As an example of the latter it has been found that certain benzoxazinones, e.g. efavirenz are useful in the inhibition of HIV RT. However, development of strains of the virus resistant to current RT inhibitors is a constant problem. Therefore, development of compounds effective against resistant strains is an important goal.

Pyrazole derivatives have been described in the literature with different uses (e.g. agrochemistry or treatment of stress-relating illness).

EP 0 627 423 describes pyrazole derivatives and their use as agrohorticultural bactericides.

U.S. Pat. No. 6,005,109 describes pyrazole derivatives and their use in the treatment of stress-relating illness.

No pyrazole derivatives have yet been described in the literature for the treatment of diseases mediated by the human immunodeficiency virus (HIV).

SUMMARY OF THE INVENTION

The invention is concerned with novel and known pyrazole derivatives, a process for their manufacture, pharmaceutical compositions and the use of such compounds in medicine, especially in the treatment of viral diseases. In particular, the compounds are inhibitors of the human immunodeficiency virus reverse transcriptase enzyme which is involved in viral replication. Consequently the compounds of this invention may be advantageously used as therapeutic agents for the treatment of diseases mediated by the human immunodeficiency virus (HIV).

DETAILED DESCRITPTION OF THE INVENTION

The present invention describes the use of compounds of formula I

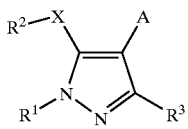

wherein
$R^1$ is optionally substituted $C_{1-12}$-alkyl, $C_{3-8}$-cycloalkyl, acyl, $C_{1-4}$-alkylsulfonyl, optionally substituted phenylsulfonyl, aryl, heterocyclyl or $C_{1-4}$-alkyl substituted with optionally substituted phenyl;
$R^2$ is aryl;
$R^3$ is $C_{1-12}$-alkyl or $C_{1-4}$-alkoxy-$C_{1-4}$-alkyl;
A is a group selected from $CH_2$-(aryl-$C_{1-4}$-alkylamino), $CH_2$-(aryl-$C_{1-4}$-alkoxy),
$CH_2$-(heterocyclyl-$C_{1-4}$-alkoxy), $C_{1-4}$-alkyl substituted with aryl or with heterocyclyl; or
A is a group of formula $CH_2$-U-heterocyclyl,
wherein U is O, S or NR″, wherein R″ is hydrogen or $C_{1-4}$-alkyl; or
A is a group of formula CH(V)Z,
wherein V is OH or F, and
wherein Z is aryl or heterocyclyl; or
A is a group of formula CH=CHW,
wherein W is aryl or heterocyclyl;
X represents S or O;
for the treatment of diseases mediated by the human immunodeficiency virus (HIV) or for the preparation of a medicament for such treatment.

The term "alkyl" as used herein denotes an optionally substituted straight or branched chain hydrocarbon residue containing 1 to 12 carbon atoms, such as methyl, ethyl, n-propyl, isopropyl, n-butyl, 1-sec-butyl, isobutyl, tert.-butyl, pentyl, hexyl, heptyl, octyl, nonyl, decyl, undecyl, dodecyl including their different isomers. Preferably, "alkyl" optionally substituted straight or branched chain hydrocarbon residue containing 1 to 7 or 1 to 6 carbon atoms. Most preferred, "alkyl" denotes an optionally substituted straight or branched chain hydrocarbon residue containing 1 to 4 carbon atoms.

Suitable substituents for the alkyl chain can be selected from one or more of aryl, heterocyclyl, alkoxy, hydroxy or halogen. The terms "aryl", "heterocyclyl", "alkoxy" and "halogen" are defined below. Preferred substituents for the alkyl chain are 1–5 substituents selected from fluorine, chlorine and bromine, more preferred 1–5 fluorine substituents and most preferred 1–3 fluorine substituents.

In case more than one substituent is attached to the alkyl group, these substituents can be identical or different from each other.

Aryl (defined below) as substituent for the alkyl group can also be substituted with 1–5 substituents selected from $C_{1-4}$-alkyl, $C_{1-4}$-alkoxy, hydroxy, fluorine, chlorine or bromine. More preferred, the aryl is substituted with 1–3 substituents selected from methyl, ethyl, methoxy, ethoxy, hydroxy, fluorine, chlorine or bromine.

Heterocyclyl (defined below) as substituent for the alkyl group can also be substituted with 1, 2, 3 or 4 (where chemically possible) substituents selected from $C_{1-4}$-alkyl, $C_{1-4}$-alkoxy, hydroxy, fluorine, chlorine or bromine. More preferred, the heterocyclyl is substituted with 1–2 substituents selected from methyl, ethyl, methoxy, ethoxy, hydroxy, fluorine, chlorine or bromine.

Alkyl in $R^1$ is preferably an optionally substituted straight or branched chain hydrocarbon residue containing 1 to 7, 1 to 6 or 1 to 4 carbon atoms as defined above. Suitable substituents for the alkyl group are selected from aryl, heterocyclyl or halogen. Preferred substituents for the alkyl chain are 1–5 substituents selected from fluorine, chlorine and bromine, more preferred 1–5 fluorine substituents and most preferred 1–3 fluorine substituents. More preferred alkyl in $R^1$ is methyl, ethyl, n-propyl, isopropyl, n-butyl, 1-sec-butyl, isobutyl, tert.-butyl, pentyl, hexyl, heptyl including their different isomers, trifluoromethyl or 2,2,2-trifluoro-ethyl. Most preferred alkyl in $R^1$ is methyl, ethyl, n-propyl, isopropyl, n-butyl, 1-sec-butyl, isobutyl, tert.-butyl, pentyl, hexyl, heptyl.

Alkyl in $R^3$ is preferably an unsubstituted straight or branched chain hydrocarbon residue containing 1 to 7 carbon atoms and most preferred methyl, ethyl, n-propyl, isopropyl, n-butyl, 1-sec-butyl, isobutyl, tert.-butyl, pentyl, hexyl, heptyl including their different isomers. More preferred alkyl in $R^3$ is an unsubstituted straight or branched chain hydrocarbon residue containing 1 to 4 carbon atoms.

The term "cycloalkyl" as used herein denotes an optionally substituted cycloalkyl group containing 3 to 8 carbon atoms, e.g. cyclopropyl, cyclobutyl, cyclopentyl, cyclohexyl, cycloheptyl or cyclooctyl, which can also be fused to an optionally substituted saturated, partially unsaturated or aromatic monocyclic, bicyclic or tricyclic heterocycle or carbocycle, e.g. to phenyl.

Suitable substituents for cycloalkyl can be selected from one or more of those named for alkyl.

Cycloalkyl in $R^1$ is as defined above, preferably an unsubstituted cycloalkyl group containing 3 to 6 carbon atoms such as cyclopropyl, cyclobutyl, cyclopentyl or cyclohexyl. More preferred cycloalkyl in $R^1$ is cyclopentyl or cyclohexyl.

The term "alkoxy" as used herein denotes an optionally substituted straight or branched chain alkyl-oxy group containing 1 to 7 carbon atoms wherein the "alkyl" portion is as defined above. Examples for alkoxy groups are methoxy, ethoxy, n-propyloxy, iso-propyloxy, n-butyloxy, 1-sec-butyloxy, iso-butyloxy, tert.-butyloxy, pentyloxy, hexyloxy, heptyloxy including their different isomers.

Suitable substituents for the alkoxy group are selected from aryl, hydroxy, halogen or amino.

The term "alkoxyalkyl" as used herein denotes an alkoxy group containing 1 to 4 carbon atoms as defined above which is bonded to an alkyl group containing 1 to 4 carbon atoms (preferably 1–2 carbon atoms) as defined above. Examples are methoxymethyl, methoxyethyl, methoxypropyl, ethoxymethyl, ethoxyethyl, ethoxypropyl, propyloxypropyl, methoxybutyl, ethoxybutyl, propyloxybutyl, butyloxybutyl, tert.-butyloxybutyl including their different isomers. Preferred alkoxyalkyl group within the invention is $C_{1-2}$-alkoxy-$C_{1-2}$-alkyl.

Alkoxyalkyl in $R^3$ is preferably methoxymethyl, methoxyethyl, ethoxymethyl or ethoxyethyl.

The term "acyl" as used herein denotes a group of formula C(=O)H, C(=O)alkyl or C(=O)phenyl wherein alkyl is an optionally substituted straight or branched chain hydrocarbon residue containing 1 to 4 carbon atoms. Most preferred acyl groups are C(=O)H, C(=O)alkyl or C(=O)phenyl wherein alkyl is an unsubstituted straight chain or branched hydrocarbon residue containing 1 to 4 carbon atoms.

Acyl in $R^1$ is independently of each other preferably methylcarbonyl (acetyl), ethylcarbonyl (propionyl), propylcarbonyl, butylcarbonyl or phenylcarbonyl (benzoyl).

The term "alkylsulfonyl" as used herein denotes a group of formula $S(=O)_2$(alkyl) wherein the alkyl is an optionally substituted straight or branched chain hydrocarbon residue containing 1 to 4 carbon atoms, preferably an unsubstituted straight or branched chain hydrocarbon residue containing 1 to 4 carbon atoms. More preferred alkylsulfonyl groups are methylsulfonyl, ethylsulfonyl, n-propylsulfonyl, iso-propylsulfonyl, n-butylsulfonyl, 1-sec-butylsulfonyl, iso-butylsulfonyl or tert.-butylsulfonyl. Alkylsulfonyl in $R^1$ is preferably methylsulfonyl, ethylsulfonyl, n-propylsulfonyl, iso-propylsulfonyl, n-butylsulfonyl, 1-sec-butylsulfonyl, iso-butylsulfonyl or tert.-butylsulfonyl.

The term "aryl" as used herein denotes an optionally substituted phenyl and naphthyl, both optionally benz-fused to an optionally substituted saturated, partially unsaturated or aromatic monocyclic, bicyclic or tricyclic heterocycle or carbocycle e.g. to cyclohexyl or cyclopentyl. Suitable substituents for aryl can be selected from 1, 2, 3, 4 or 5, preferably 1, 2 or 3 residues of those named for alkyl, preferably selected from $C_{1-4}$-alkyl, $C_{1-4}$-alkoxy, hydroxy, fluorine, chlorine, bromine, cyano, nitro, S—$C_{1-4}$-alkyl and NRR', wherein R and R' are independently of each other hydrogen or $C_{1-4}$-alkyl. The substituents for aryl can also be selected from $C_{1-4}$-alkyl, $C_{1-4}$-alkoxy, hydroxy, fluorine, chlorine or bromine. In case more than one substituent is attached to the aryl group, these substituents can be identical or different from each other.

Aryl in $R^1$ is preferably phenyl, 2-chloro-phenyl, 3-chloro-phenyl, 4-chloro-phenyl, 1-fluoro-phenyl, 2-fluoro-phenyl or 3-fluoro-phenyl. Most preferred aryl in $R^1$ is phenyl.

Aryl in $R^2$ is preferably phenyl or naphthyl.

"Optionally substituted phenyl" as used herein includes phenyl substituted with 1–5 substituents, preferably 1, 2 or 3 residues of those selected $C_{1-4}$-alkyl, $C_{1-4}$-alkoxy, hydroxy, fluorine, chlorine, bromine, cyano and nitro. The substituents for phenyl in R' may also be selected from $C_{1-4}$-alkyl, $C_{1-4}$-alkoxy, hydroxy, fluorine, chlorine or bromine. Examples for the optionally substituted phenyl are phenyl, 2-methyl-phenyl, 3-methyl-phenyl, 4-methyl-phenyl, 2,3-dimethylphenyl, 2,4-dimethylphenyl, 2,5-dimethylphenyl, 2,6-dimethylphenyl, 3,4-dimethylphenyl, 3,5-dimethylphenyl, 3,6-dimethylphenyl, 2-methoxy-phenyl, 3-methoxy-phenyl, 4-methoxy-phenyl, 2,3-dimethoxyphenyl, 2,4-dimethoxyphenyl, 2,5-dimethoxyphenyl, 2,6-dimethoxyphenyl, 3,4-dimethoxyphenyl, 3,5-dimethoxyphenyl, 3,6-dimethoxyphenyl, 2-hydroxyphenyl, 3-hydroxyphenyl, 4-hydroxyphenyl, 2,3-dihydroxyphenyl, 2,4-dihydroxyphenyl, 2,5-dihydroxyphenyl, 2,6-dihydroxyphenyl, 3,4-dihydroxyphenyl, 3,5-dihydroxyphenyl, 3,6-dihydroxyphenyl, 2-fluoro-phenyl, 3-fluoro-phenyl, 4-fluoro-phenyl, 2,3-difluorophenyl, 2,4-difluorophenyl, 2,5-difluorophenyl, 2,6-difluorophenyl, 3,4-difluorophenyl, 3,5-difluorophenyl, 2,3,4-trifluorophenyl, 3,4,5-trifluorophenyl, 2,3,4,5,6-pentafluorophenyl, 2-chloro-phenyl, 3-chloro-phenyl, 4-chloro-phenyl, 2,3-dichlorophenyl, 2,4-dichlorophenyl, 2,5-dichlorophenyl, 2,6-dichlorophenyl, 3,4-dichlorophenyl, 3,5-dichlorophenyl, 2,3,4-trichlorophenyl, 3,4,5-trichlorophenyl, 2,3,4,5,6-pentachlorophenyl, 2-bromophenyl, 3-bromophenyl, 4-bromophenyl, 2,3-dibromophenyl, 2,4-dibromophenyl, 2,5-dibromophenyl, 2,6-dibromophenyl, 3,4-dibromophenyl, 3,5-dibromophenyl, 3,6-dibromophenyl, 2-cyano-phenyl, 3-cyano-phenyl, 4-cyano-phenyl, 2,3-dicyanophenyl, 2,4-dicyanophenyl, 2,5-dicyanophenyl, 2,6-dicyanophenyl, 3,4-dicyanophenyl, 3,5-dicyanophenyl, 3,6-dicyanophenyl, 2-nitro-phenyl, 3-nitro-phenyl, 4-nitro-phenyl, 2,3-dinitrophenyl, 2,4-dinitrophenyl, 2,5-dinitrophenyl, 2,6-dinitrophenyl, 3,4-dinitrophenyl, 3,5-dinitrophenyl, 3,6-dinitrophenyl, 1-chloro-2-methoxy-phenyl, 1-chloro-3-methoxy-phenyl, 1-chloro-4-methoxy-phenyl, 1-chloro-5-methoxy-phenyl, 2-chloro-1-methoxy-phenyl, 2-chloro-3-methoxy-phenyl, 2-chloro-4-methoxy-phenyl, 2-chloro-5-methoxy-phenyl, 3-chloro-1-methoxy-phenyl, 3-chloro-2-methoxy-phenyl, 3-chloro-4-methoxy-phenyl, 3-chloro-5-methoxy-phenyl. More preferred examples for the optionally substituted phenyl are phenyl, 2-methoxy-phenyl, 3-methoxy-phenyl, 4-methoxy-phenyl, 2-chloro-phenyl, 3-chloro-phenyl, 4-chloro-phenyl, 2,3-dichlorophenyl, 2,4-dichlorophenyl, 2,5-dichlorophenyl, 2,6-dichlorophenyl, 3,4-dichlorophenyl, 3,5-dichlorophenyl, 2,3,4-trichlorophenyl, 3,4,5-trichlorophenyl or 2,3,4,5,6-pentachlorophenyl. Most preferred examples for the optionally substituted phenyl are phenyl, 4-methoxyphenyl, 3-chloro-phenyl or 3,5-dichlorophenyl.

The term "optionally substituted phenylsulfonyl" as used herein denotes a group of formula S(=O)$_2$(phenyl) wherein phenyl is optionally substituted with 1–5 substituents, preferably 1, 2 or 3 residues of those selected from $C_{1-4}$-alkyl, $C_{1-4}$-alkoxy, hydroxy, fluorine, chlorine or bromine. Examples for the optionally substituted phenyl are as mentioned above, preferably phenylsulfonyl.

The term "$C_{1-4}$-alkyl substituted with aryl" as used herein denotes a $C_{1-4}$-alkyl as defined above which is substituted with an aryl group (preferably a phenyl group) or preferably a substituted aryl group (preferably a substituted phenyl group) which is substituted with 1, 2, 3, 4 or 5, preferably 1, 2 or 3 residues of those substituents selected from $C_{1-4}$-alkyl, $C_{1-4}$-alkoxy, hydroxy, fluorine, chlorine, bromine, cyano, S—$C_{1-4}$-alkyl and NRR', wherein R and R' are independently of each other hydrogen or $C_{1-4}$-alkyl. The substituents for substituted aryl (preferably phenyl) may also be selected from $C_{1-4}$-alkyl, $C_{1-4}$-alkoxy, hydroxy, fluorine, chlorine, bromine and cyano, or the substituents may optionally be selected from $C_{1-4}$-alkyl, $C_{1-4}$-alkoxy, hydroxy, fluorine, chlorine or bromine. In case more than one substituent is attached to the aryl group (preferably phenyl group), these substituents can be identical or different from each other. Preferred substituents for the substituted aryl (preferably phenyl) are selected from methyl, ethyl, methoxy, ethoxy, hydroxy, fluorine, chlorine, bromine or the substituents are selected from methyl, ethyl, methoxy, ethoxy, hydroxy, fluorine, chlorine, bromine, cyano, amino, methyl-amino and di-methyl-amino. Within the invention "$C_{1-2}$-alkyl substituted with optionally substituted phenyl" is preferred. Examples are phenylmethyl (benzyl), phenylethyl, phenylpropyl, phenylbutyl, tolylmethyl, tolylethyl, tolylpropyl, tolylbutyl, 2,3-dimethylphenylmethyl, 2,4-dimethylphenylmethyl, 2,5-dimethylphenylmethyl, 2,6-dimethylphenylmethyl, 3,4-dimethylphenylmethyl, 3,5-dimethylphenylmethyl, 3,6-dimethylphenylmethyl, methoxyphenylmethyl, methoxyphenylethyl, methoxyphenylpropyl, methoxyphenylbutyl, dimethoxyphenylmethyl, dimethoxyphenylethyl, dimethoxyphenylpropyl, dimethoxyphenylbutyl, 2-hydroxyphenylmethyl, 3-hydroxyphenylmethyl, 4-hydroxyphenylmethyl, 2,3-dihydroxyphenylmethyl, 2,4-dihydroxyphenylmethyl, 2,5-dihydroxyphenylmethyl, 2,6-dihydroxyphenylmethyl, 3,4-dihydroxyphenylmethyl, 3,5-dihydroxyphenylmethyl, 3,6-dihydroxyphenylmethyl, 2-hydroxyphenylethyl, 3-hydroxyphenylethyl, 4-hydroxyphenylethyl, 2-hydroxyphenylpropyl, 3-hydroxyphenylpropyl, 4-hydroxyphenylpropyl, 2-hydroxyphenylbutyl, 3-hydroxyphenylbutyl, 4-hydroxyphenylbutyl, 2-fluorophenylmethyl, 3-fluorophenylmethyl, 4-fluorophenylmethyl, 2,3-difluorophenylmethyl, 2,4-difluorophenylmethyl, 2,5-difluorophenylmethyl, 2,6-difluorophenylmethyl, 3,4-difluorophenylmethyl, 3,5-difluorophenylmethyl, 3,6-difluorophenylmethyl, 2-fluorophenylethyl, 3-fluorophenylethyl, 4-fluorophenylethyl, 2-chlorophenylmethyl, 3-chlorophenylmethyl, 4-chlorophenylmethyl, 2,3-dichlorophenylmethyl, 2,4-dichlorophenylmethyl, 2,5-dichlorophenylmethyl, 2,6-dichlorophenylmethyl, 3,4-dichlorophenylmethyl, 3,5-dichlorophenylmethyl, 3,6-dichlorophenylmethyl, 2-chlorophenylethyl, 3-chlorophenylethyl, 4-chlorophenylethyl, 2-bromophenylmethyl, 3-bromophenylmethyl, 4-bromophenylmethyl, 2,3-dibromophenylmethyl, 2,4-dibromophenylmethyl, 2,5-dibromophenylmethyl, 2,6-dibromophenylmethyl, 3,4-dibromophenylmethyl, 3,5-dibromophenylmethyl, 3,6-dibromophenylmethyl, 2-bromophenylethyl, 3-bromophenylethyl, 4-bromophenylethyl, 2-cyanophenylmethyl, 3-cyanophenylmethyl, 4-cyanophenylmethyl, 2,3-dicyanophenylmethyl, 2,4-dicyanophenylmethyl, 2,5-dicyanophenylmethyl, 2,6-dicyanophenylmethyl, 3,4-dicyanophenylmethyl, 3,5-dicyanophenylmethyl, 3,6-dicyanophenylmethyl, 2-dimethylaminophenylmethyl, 3-dimethylaminophenylmethyl 4-dimethylaminophenylmethyl, 2,3-di-dimethylaminophenylmethyl, 2,4-di-dimethylaminophenylmethyl, 3,5-di-dimethylaminophenylmethyl, 2,6-di-dimethylaminophenylmethyl, 3,4-di-dimethylaminophenylmethyl, 3,5-di-dimethylaminophenylmethyl or 3,6-di-dimethylaminophenylmethyl.

$C_{1-4}$-alkyl substituted with optionally substituted phenyl for $R^1$ is as defined above, preferably phenylmethyl (benzyl).

$C_{1-4}$-alkyl substituted with optionally substituted phenyl for the substituent A are as defined above, preferably phenylmethyl (benzyl), 4-methylphenylmethyl, 4-methoxyphenylmethyl, 4-nitrophenylmethyl, 4-fluorophenylmethyl, 4-chlorophenylmethyl, 4-bromophenylmethyl, phenylethyl, 4-methylphenylethyl, 4-methoxyphenylethyl, 4-nitrophenylethyl, 4-fluorophenylethyl, 4-chlorophenylethyl, 4-bromophenylethyl, phenylpropyl, phenylbutyl, 2-cyanophenylmethyl, 3-cyanophenylmethyl, 4-cyanophenylmethyl, 2,3-dicyanophenylmethyl, 2,4-dicyanophenylmethyl, 2,5-dicyanophenylmethyl, 2,6-dicyanophenylmethyl, 3,4-dicyanophenylmethyl, 3,5-dicyanophenylmethyl, 3,6-dicyanophenylmethyl, 2-dimethylaminophenylmethyl, 3-dimethylaminophenylmethyl, 4-dimethylaminophenylmethyl, 2,3-di-dimethylaminophenylmethyl, 2,4-di-dimethylaminophenylmethyl, 2,5-di-dimethylaminophenylmethyl, 2,6-di-dimethylaminophenylmethyl, 3,4-di-dimethylaminophenylmethyl, 3,5-di-dimethylaminophenylmethyl or 3,6-di-dimethylaminophenylmethyl. More preferred examples are phenylmethyl (benzyl), phenylethyl, 2-cyanophenylmethyl, 3-cyanophenylmethyl, 4-cyanophenylmethyl, 2-dimethylaminophenylmethyl, 3-dimethylaminophenylmethyl or 4-dimethylaminophenylmethyl.

Aryl in CH(OH)-aryl for the substituent A is as defined above, preferably phenyl, naphtyl or an optionally substituted phenyl group. Suitable substituents for aryl can be selected from 1, 2, 3, 4 or 5 of $C_{1-4}$-alkyl, $C_{1-4}$-alkoxy, hydroxy, fluorine, chlorine or bromine, preferably 1, 2 or 3 residues of methyl, ethyl, methoxy, ethoxy, hydroxy, fluorine, chlorine or bromine. Preferred aryl in CH(OH)-aryl for the substituent A is phenyl.

Aryl in CH(F)-aryl for the substituent A is as defined above, preferably phenyl, naphtyl or an optionally substituted phenyl group. Suitable substituents for aryl can be selected from 1, 2, 3, 4 or 5 of $C_{1-4}$-alkyl, $C_{1-4}$-alkoxy, hydroxy, fluorine, chlorine or bromine, preferably 1, 2 or 3 residues of methyl, ethyl, methoxy, ethoxy, hydroxy, fluorine, chlorine or bromine. Preferred aryl in CH(OH)-aryl for the substituent A is phenyl.

Aryl in CH=CH-aryl for the substituent A is as defined above, preferably phenyl or an optionally substituted phenyl group. The ethenediyl group (—CH=CH—) can have the (E) or (Z) configuration. Both isomeric forms of these compounds are embraced by the present invention. The preferred configuration of the ethenediyl group within the invention is the (E) configuration. Suitable substituents for aryl can be selected from 1, 2, 3, 4 or 5 of $C_{1-4}$-alkyl, $C_{1-4}$-alkoxy, hydroxy, fluorine, chlorine or bromine, preferably 1, 2 or 3 residues of methyl, ethyl, methoxy, ethoxy, hydroxy, fluorine, chlorine or bromine. Preferred aryl in CH=CH-aryl for the substituent A is phenyl, 4-methylphenyl, 4-methoxyphenyl, 4-fluorophenyl or 4-chlorophenyl. Most preferred aryl in CH=CH-aryl for the substituent A is phenyl.

The term "arylalkoxy" as used herein denotes an aryl or an optionally substituted aryl group as defined above which is bonded to an alkoxy group containing 1 to 4 carbon atoms as defined above. Preferred examples are phenyl-methyl-oxy (phenylmethoxy or benzyloxy), 4-methylphenylmethoxy, 4-methoxyphenylmethoxy, 4-fluorophenylmethoxy or 4-chlorophenylmethoxy. Most preferred example is phenyl-methyl-oxy.

The term "arylalkylamino" as used herein denotes a group of formula N(R)—$C_{1-4}$-alkyl-aryl wherein an aryl or an optionally substituted aryl group as defined above is bonded to an alkyl group containing 1 to 4 carbon, which is bonded to an amino group. The amino group is also substituted with R, wherein R is a hydrogen or unsubstituted straight or branched chain hydrocarbon residue containing 1 to 4 carbon atoms. An example is phenyl-methyl-amino(methyl) (benzylaminomethyl).

The term "heterocyclyl" as used herein denotes optionally substituted aromatic or non-aromatic monocyclic or bicyclic heterocycle which contains one or more hetero atoms selected from nitrogen, oxygen and sulfur. Also included within the present invention are heterocyclyl compounds with an oxo (=O) group. Examples of suitable heterocycles are furyl, 1-pyrrolyl, 2-pyrrolyl, 1-thiophenyl, 2-thiophenyl, 2-pyridinyl (2-pyridyl), 3-pyridinyl (3-pyridyl), 4-pyridinyl (4-pyridyl), 1H-pyridin-2-one, 1H-pyridin-4-one, 3H-pyrimidine-4-one, pyridazine (1,2-diazine), pyrimidine (1,3-diazine), pyrazine (1,4-diazine), oxazole or isoxazole (iso-oxazole).

Suitable substituents for heterocyclyl can be selected from, 1, 2, 3 or 4 (where chemically possible), more preferred 1, 2 or 3, most preferred 1 or 2 substituents selected from $C_{1-4}$-alkyl, fluorine, chlorine, bromine, cyano, nitro and NRR', wherein R and R' are independently of each other hydrogen or $C_{1-4}$-alkyl. The substituents for substituted heterocyclyl may also be selected from $C_{1-4}$-alkyl, $C_{1-4}$-alkoxy, hydroxy, cyano, fluorine, chlorine and bromine, or the substituents may optionally be selected from $C_{1-4}$-alkyl, $C_{1-4}$-alkoxy, hydroxy, fluorine, chlorine and bromine. In case more than one substituent is attached to the heterocyclyl group, these substituents can be identical or different from each other. For all the cited examples for "heterocyclyl" these substituents can be at any chemically possible position. For example methylpyridyl means that the methyl substituent may be attached in the 3, 4, 5 or 6 position of a 2-pyridyl or in the 2, 4, 5 or 6 position of a 3-pyridyl or in the 2, 3, 5 or 6 position of a 4-pyridyl.

The term "$C_{1-4}$-alkyl substituted with heterocyclyl" as used herein for the substituent A denotes a $C_{1-4}$-alkyl as defined above which is substituted with a heterocyclyl group or with a substituted heterocyclyl group which is substituted with 1, 2, 3 or 4 (where chemically possible), more preferred 1, 2 or 3, most preferred 1 or 2 of those substituents selected from $C_{1-4}$-alkyl, $C_{1-4}$-alkoxy, hydroxy, fluorine, chlorine, bromine, cyano, S—$C_{1-4}$-alkyl and NRR', wherein R and R' are independently of each other hydrogen or $C_{1-4}$-alkyl. The substituents for substituted heterocyclyl may also be selected from $C_{1-4}$-alkyl, $C_{1-4}$-alkoxy, hydroxy, fluorine, chlorine and bromine. Within the invention $C_1$, $C_{1-2}$-and $C_{3-4}$-alkyl substituted with optionally substituted heterocyclyl are preferred. Examples are furylmethyl, furylethyl, furylpropyl, furylbutyl, methylfurylmethyl, methylfurylethyl, dimethylfurylmethyl, ethylfurylmethyl, methoxyfurylmethyl, methoxyfurylethyl, dimethoxyfurylmethyl, hydroxyfurylmethyl, hydroxyfurylethyl, dihydroxyfurylmethyl, fluorofurylmethyl, difluorofurylmethyl, chloro furylmethyl, chlorofurylethyl, dichlorofurylmethyl, dichlorofurylmethyl, bromofurylmethyl, dibromofurylmethyl, pyrrolylmethyl, pyrrolylethyl, pyrrolylpropyl, pyrrolylbutyl, methylpyrrolylmethyl, methylpyrrolylethyl, dimethylpyrrolylmethyl, ethylpyrrolylmethyl, methoxypyrrolylmethyl, methoxypyrrolylethyl, dimethoxypyrrolylmethyl, hydroxypyrrolylmethyl, hydroxypyrrolylethyl, dihydroxypyrrolylmethyl, fluoropyrrolylmethyl, difluoropyrrolylmethyl, chloropyrrolylmethyl, chloropyrrolylethyl, dichloropyrrolylmethyl, dichloropyrrolylmethyl, bromorpyrrolylmethyl, dibromopyrrolylmethyl, thiophenyl-methyl (2-thiophenylmethyl, 3-thiophenylmethyl), thiophenylethyl, thiophenylpropyl, thiophenylbutyl, methylthiophenylmethyl, methylthiophenylethyl, dimethylthiophenylmethyl, ethylthiophenylmethyl, methoxythiophenylmethyl, methoxythiophenylethyl, dimethoxythiophenylmethyl, hydroxythiophenylmethyl, hydroxythiophenylethyl, dihydroxythiophenylmethyl, fluorothiophenylmethyl, difluorothiophenylmethyl, chlorothiophenylmethyl, chlorothiophenylethyl, dichlorothiophenylmethyl, dichlorothiophenylmethyl, bromorthiophenylmethyl, dibromothiophenylmethyl, pyridinylmethyl (2-pyridinylmethyl, 3-pyridinylmethyl, 4-pyridinylmethyl), pyridinylethyl, pyridinylpropyl, pyridinylbutyl, 3-methyl-2-pyridinylmethyl, 4-methyl-2-pyridinylmethyl, 5-methyl-2-pyridinylmethyl, 6-methyl-2-pyridinylmethyl, 2-methyl-3-pyridinylmethyl, 4-methyl-3-pyridinylmethyl, 5-methyl-3-pyridinylmethyl, 6-methyl-3-pyridinylmethyl, 24 methyl-4-pyridinylmethyl, 3-methyl-4-pyridinylmethyl, 5-methyl-4-pyridinylmethyl, 6-methyl-4-pyridinylmethyl, 3-m ethoxy-2-pyridinylmethyl, 4-methoxy-2-pyridinylmethyl, 5-methoxy-2-pyridinylmethyl, 6-methoxy-2-pyridinylmethyl, 2-methoxy-3-pyridinylmethyl, 4-methoxy-3-pyridinylmethyl, 5-methoxy-3-pyridinylmethyl, 6-methoxy-3-pyridinylmethyl, 2-methoxy-4-pyridinylmethyl, 3-methoxy-4-pyridinylmethyl, 5-methoxy-4-pyridinylmethyl, 6-methoxy-4-pyridinylmethyl, 3-fluoro-2-pyridinylmethyl, 4-fluoro-2-pyridinylmethyl, 5-fluoro-2-pyridinylmethyl, 6-fluoro-2-pyridinylmethyl, 2-fluoro-3-pyridinylmethyl, 4-fluoro-3-pyridinylmethyl, 5-fluoro-3-pyridinylmethyl, 6-fluoro-3-pyridinylmethyl, 2-fluoro-4-pyridinylmethyl, 3-fluoro-4-pyridinylmethyl, 5-fluoro-4-pyridinylmethyl, 6-fluoro-4-pyridinylmethyl, 3-chloro-2-pyridinylmethyl, 4-chloro-2-pyridinylmethyl, 5-chloro-2-pyridinylmethyl, 6-chloro-2-pyridinylmethyl, 2-chloro-3-pyridinylmethyl, 4-chloro-3-pyridinylmethyl, 5-chloro-3-pyridinylmethyl, 6-chloro-3-pyridinylmethyl, 2-chloro-4-pyridinylmethyl, 3-chloro-4-pyridinylmethyl, 5-chloro-4-pyridinylmethyl, 6-chloro-4-pyridinylmethyl, 3-bromo-2-pyridinylmethyl, 4-bromo-2-pyridinylmethyl, 5-bromo-2-pyridinylmethyl, 6-bromo-2-pyridinylmethyl, 2-bromo-3-pyridinylmethyl, 4-bromo-3-pyridinylmethyl, 5-bromo-3-pyridinylmethyl, 6-bromo-3-pyridinylmethyl, 2-bromo-4-pyridinylmethyl, 3-bromo-4-pyridinylmethyl, 5-bromo-4-pyridinylmethyl, 6-bromo-4-pyridinylmethyl, 3-cyano-2-pyridinylmethyl, 4-cyano-2-pyridinylmethyl, 5-cyano-2-pyridinylmethyl, 6-cyano-2-pyridinylmethyl, 2-cyano-3-pyridinylmethyl, 4-cyano-3-pyridinylmethyl, 5-cyano-3-pyridinylmethyl, 6-cyano-3-pyridinylmethyl, 2-cyano-4-pyridinylmethyl, 3-cyano-4-pyridinylmethyl, 5-cyano-4-pyridinylmethyl, 6-cyano-4-pyridinylmethyl, 3-(methylthio)-2-pyridinylmethyl, 4-(methylthio)-2-pyridinylmethyl, 5-(methylthio)-2-pyridinylmethyl, 6-(methylthio)-2-pyridinylmethyl, 2-(methylthio)-3-pyridinylmethyl, 4-(methylthio)-3-pyridinylmethyl, 5-(methylthio)-3-pyridinylmethyl, 6-(methylthio)-3-pyridinylmethyl, 2-(methylthio)-4-pyridinylmethyl, 3-(methylthio)-4-pyridinylmethyl, 5-(methylthio)-4-pyridinylmethyl, 6-(methylthio)-4-pyridinylmethyl, 2-chloro-3-methyl-4-pyridinylmethyl, 2-chloro-5-methyl-4-pyridinylmethyl, 2-chloro-6-methyl-4-pyridinylmethyl, 3-chloro-5-methyl-4-pyridinylmethyl, 3-chloro-6-methyl-4-pyridinylmethyl, 5-chloro-6-methyl-4-pyridinylmethyl, methylpyridinylethyl, dimethylpyridinylmethyl, ethylpyridinylmethyl, methoxypyridinylmethyl, methoxypyridinylethyl, dimethoxypyridinylmethyl, hydroxypyridinylmethyl, hydroxypyridinylethyl, dihydroxypyridinylmethyl, fluoropyridinylmethyl, difluoropyridinylmethyl, chloropyridinylmethyl, chloropyridinylethyl, dichloropyridinylmethyl, dichloropyridinylmethyl, fromorpyridinylmethyl, dibromopyridinylmethyl, indolylmethyl, indolylethyl, indolylpropyl, indolylbutyl, methylindolylmethyl, methylindolylethyl, dimethylindolylmethyl, ethylindolylmethyl, methoxyindolylmethyl, methoxyindolylmethyl, dimethoxyindolylmethyl, hydroxyindolylmethyl, hydroxyindolylethyl, dihydroxyindolylmethyl, fluoroindolylmethyl, difluoroindolylmethyl, chloroindolylmethyl, chloroindolylethyl, dichloroindolylmethyl, dichloroindolylmethyl, bromorindolylmethyl, dibromoindolylmethyl, 2-bromo-pyrimidin-4-yl, 5-bromo-pyrimidin-4-yl, 6-bromo-pyrimidin-4-yl, oxazolylmethyl, 3-methyl-oxazolylmethyl, 4-methyl-oxazolylmethyl, 5-methyl-oxazolylmethyl, 3,5-dimethyl-oxazolylmethyl, 3,4-dimethyl-oxazolylmeth, 1, 4,5-dimethyl-oxazolylmethyl, oxazolylmethyl or isoxazolylmethyl. Preferred examples are furylmethyl, furylethyl, pyrrolylmethyl, pyrrolylethyl, 4-pyridinylmethyl (2-pyridinylmethyl, 3-pyridinylmethyl, 4-pyridinylmethyl), 4-pyridinylethyl, indolylmethyl, indolylethyl, 2-bromo-pyrimidin-4-yl, 5-bromo-pyrimidin-4-yl, 6-bromo-pyrimidin-4-yl, thiophenylmethyl (2-thiophenylmethyl, 3-thiophenylmethyl), thiophenylethyl, 6-bromo-pyrimidin-4-yl, oxazolylmethyl, 3-methyl-oxazolylmethyl, 4-methyl-oxazolylmethyl, 5-methyl-oxazolylmethyl, 3,5-dimethyl-oxazolylmethyl, 3,4-dimethyl-oxazolylmethyl, 4,5-dimethyl-oxazolylmethyl, oxazolylmethyl, isoxazolylmethyl, 3-methoxy-4-pyridinylmethyl, 2-fluoro-4-pyridinylmethyl, 2-chloro-4-pyridinylmethyl, 3-chloro-4-pyridinylmethyl, 5-bromo-3-pyridinylmethyl, 3-cyano-2-pyridinylmethyl, 2-(methylthio)-3-pyridinylmethyl, 3-chloro-5-methyl-4-pyridinylmethyl, and most preferred examples are 4-pyridinylmethyl and 4-pyridinylethyl.

The formula "CH$_2$-U-heterocyclyl" as used herein for the substituent A denotes a heterocyclyl group as defined above, which is connected to the group "U" which represents O, S or NR", wherein R" is hydrogen or C$_{1-4}$-alkyl. The "heterocyclyl-U"-moiety is connected to a methyl group. The above mentioned heterocyclyl group is optionally substituted with 1–4, preferred 1–3, more preferred 1–2 substituents selected from C$_{1-4}$-alkyl, fluorine, chlorine, bromine, cyano, nitro and NRR', wherein R and R' are independently of each other hydrogen or C$_{1-4}$-alkyl. Preferred examples for the "heterocyclyl-U"-moiety are 4-pyridyl-oxy, 3-pyridyl-oxy, 2-pyridyl-oxy, 2-nitro-3-pyridyl-oxy, 2-amino-3-pyridyl-oxy, 4-methyl-3-pyridyl-oxy, 5-chloro-3-pyridyl-oxy, 2-amino-6-methyl-1,3-pyrimidin-4yl-oxy, 4-pyridyl-mercapto, 3-pyridyl-mercapto, 2-pyridyl-mercapto, 4-pyridyl-amino, 3-pyridyl-amino or 2-pyridyl-amino.

Heterocyclyl in CH(OH)-heterocyclyl for the substituent A is as defined above, preferably furyl, 1-pyrrolyl, 2-pyrrolyl, 2-pyridinyl, 3-pyridinyl or 4-pyridinyl or an optionally substituted heterocyclyl group. Suitable substituents for heterocyclyl can be selected from 1, 2, 3 or 4 (where chemically possible) of C$_{1-4}$-alkyl, C$_{1-4}$-alkoxy, hydroxy, fluorine, chlorine or bromine, preferably 1 or 2 of methyl, ethyl, methoxy, ethoxy, hydroxy, fluorine, chlorine or bromine. Preferred heterocyclyl in CH(OH)-heterocyclyl for the substituent A are 2-pyridinyl, 3-pyridinyl or 4-pyridinyl.

Heterocyclyl in CH(F)-heterocyclyl for the substituent A is as defined above, preferably furyl, 1-pyrrolyl, 2-pyrrolyl, 2-pyridinyl, 3-pyridinyl or 4-pyridinyl or an optionally substituted heterocyclyl group. Suitable substituents for heterocyclyl can be selected from 1, 2, 3 or 4 (where chemically possible) of C$_{1-4}$-alkyl, C$_{1-4}$-alkoxy, hydroxy, fluorine, chlorine or bromine, preferably 1 or 2 of methyl, ethyl, methoxy, ethoxy, hydroxy, fluorine, chlorine or bromine. Preferred heterocyclyl in CH(OH)-heterocyclyl for the substituent A is 4-pyridinyl.

Heterocyclyl in CH=CH-heterocyclyl for the substituent A is as defined above, preferably pyridinyl or an optionally substituted pyridinyl group. The ethenediyl group (—CH=CH—) can have the (E) or (Z) configuration. Both isomeric forms of these compounds are embraced by the present invention. The preferred configuration of the ethenediyl group within the invention is the (E) configuration. Suitable substituents for heterocyclyl can be selected from 1, 2, 3 or 4 (where chemically possible) of C$_{1-4}$-alkyl, C$_{1-4}$-alkoxy, hydroxy, fluorine, chlorine or bromine, preferably 1 or 2 of methyl, ethyl, methoxy, ethoxy, hydroxy, fluorine, chlorine or bromine. Preferred heterocyclyl in CH=CH-heterocyclyl for the substituent A is pyridinyl, 4-methylpyridinyl, 4-methoxypyridinyl, 4-fluoropyridinyl or 4-chloropyridinyl. Most preferred heterocyclyl in CH=CH-heterocyclyl for the substituent A is pyridinyl.

The term "heterocyclylalkoxy" as used herein denotes an aryl or an optionally substituted heterocyclyl group as defined above which is bonded to an alkoxy group containing 1 to 4 carbon atoms as defined above. Preferred examples are 4-pyridyl-methyl-oxy (4-pyridylmethoxy), 3-pyridyl-methyl-oxy (3-pyridylmethoxy), 2-pyridyl-methyl-oxy (2-pyridylmethoxy).

The term halogen stands for fluorine, chlorine, bromine and iodine. More preferred halogen is fluorine, chlorine or bromine and most preferred halogen is fluorine or chlorine.

Within the invention the term "X" represents S or O, preferably S.

Any functional (i.e. reactive) group present in a side-chain may be protected, with the protecting group being a group which is known per se, for example, as described in "Protective Groups in Organic Synthesis", 2nd Ed., T. W. Greene and P. G. M. Wuts, John Wiley & Sons, New York, N.Y., 1991. For example, an amino group can be protected by tert.-butoxycarbonyl (BOC) or benzyloxycarbonyl (Z).

The compounds of this invention may contain one or more asymmetric carbon atoms and may therefore occur as racemates and racemic mixtures, single enantiomers, diastereomeric mixtures and individual diastereomers. Furthermore, where a compound of the invention contains an olefinic double bond, this can have the (E) or (Z) configuration. Also, each chiral center may be of the R or S configuration. All such isomeric forms of these compounds are embraced by the present invention.

Compounds of formula I which are acidic can form pharmaceutically acceptable salts with bases such as alkali metal hydroxides, e.g. sodium hydroxide and potassium hydroxide; alkaline earth metal hydroxides, e.g. calcium hydroxide, barium hydroxide and magnesium hydroxide, and the like; with organic bases e.g. N-ethyl piperidine, dibenzylamine, and the like. Those compounds of formula I which are basic can form pharmaceutically acceptable salts with inorganic acids, e.g. with hydrohalic acids such as hydrochloric acid and hydrobromic acid, sulphuric acid, nitric acid and phosphoric acid, and the like, and with organic acids, e.g. with acetic acid, formic acid, tartaric acid, succinic acid, fumaric acid, maleic acid, malic acid, salicylic acid, citric acid, methanesulphonic acid and p-toluene sulphonic acid, and the like. The formation and isolation of such salts can be carried out according to methods known in the art.

A preferred embodiment of the invention is the use of compounds of formula I wherein

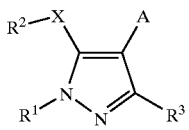

I $R^1$ is optionally substituted $C_{1-12}$-alkyl, $C_{3-8}$-cycloalkyl, acyl, $C_{1-4}$-alkylsulfonyl,
optionally substituted phenylsulfonyl, aryl, heterocyclyl or $C_{1-4}$-alkyl substituted with optionally substituted phenyl,
wherein $C_{1-12}$-alkyl may be substituted with 1–5 substituents selected from fluorine, chlorine and bromine, and
wherein phenyl may be substituted with 1–5 substituents selected from $C_{1-4}$-alkyl, $C_{1-4}$-alkoxy, hydroxy, fluorine, chlorine, bromine and cyano;
$R_2$ is optionally substituted phenyl,
wherein phenyl may be substituted with 1–5 substituents selected from $C_{1-4}$-alkyl, $C_{1-4}$-alkoxy, hydroxy, fluorine, chlorine, bromine, cyano and nitro;
$R^3$ is $C_{1-2}$-alkyl or $C_{1-4}$-alkoxy-$C_{1-4}$-alkyl;
A is a group selected from $CH_2$-(aryl-$C_{1-4}$-alkylamino), $CH_2$-(aryl-$C_{1-4}$-alkoxy), $CH_2$-(heterocyclyl-$C_{1-4}$-alkoxy), $C_{1-4}$-alkyl substituted with optionally substituted aryl or with optionally substituted heterocyclyl,
wherein aryl may be substituted with 1–5 substituents or heterocyclyl is substituted with 1–4 substituents and the substituents are selected from $C_{1-4}$-alkyl, $C_{1-4}$-alkoxy, hydroxy, fluorine, chlorine, bromine, cyano, S—$C_{1-4}$-alkyl and NRR', wherein R and R' are independently of each other hydrogen or $C_{1-4}$-alkyl; or
A is a group of formula $CH_2$-U-heterocyclyl,
wherein U is O, S or NR", wherein R" is hydrogen or $C_{1-4}$-alkyl, and wherein heterocyclyl is optionally substituted with 1–4 substituents selected from $C_{1-4}$-alkyl, fluorine, chlorine, bromine, cyano, nitro and NRR', wherein R and R' are independently of each other hydrogen or $C_{1-4}$-alkyl; or
A is a group of formula CH(V)Z,
wherein V represents OH or F, and
wherein Z represents aryl or heterocyclyl; or
A is a group of formula CH=CHW,
wherein W represents optionally substituted aryl or optionally substituted heterocyclyl, and
wherein aryl may be substituted with 1–5 substituents or heterocyclyl may be substituted with 1–4 substituents and the substituents are selected from $C_{1-4}$-alkyl, $C_{1-4}$-alkoxy, hydroxy, cyano, fluorine, chlorine and bromine;
X represents S or O;
for the treatment of diseases mediated by the human immunodeficiency virus (HIV) or for the preparation of a medicament for such treatment.

Further preferred embodiments of the invention is the use of compounds of formula I wherein
R' is optionally substituted $C_{1-12}$-alkyl, $C_{3-8}$-cycloalkyl, aryl, heterocyclyl or $C_{1-4}$-alkyl substituted with phenyl,
wherein $C_{1-12}$-alkyl may be substituted with 1–5 fluorine substituents,
preferred wherein
R' is optionally substituted $C_{1-7}$-alkyl, $C_{3-8}$-cycloalkyl, aryl, heterocyclyl or $C_{1-4}$-alkyl substituted with phenyl,
wherein $C_{1-7}$-alkyl maybe substituted with 1–3 fluorine substituents,
more preferred wherein
R' is optionally substituted $C_{1-7}$-alkyl, $C_{3-6}$-cycloalkyl, phenyl, pyridyl or benzyl,
wherein $C_{1-7}$-alkyl may be substituted with 1–3 fluorine substituents,
most preferred wherein
R' is $C_{1-7}$-alkyl;
$R^2$ is substituted phenyl, substituted with 1–5 substituents selected from $C_{1-4}$-alkyl, $C_{1-4}$-alkoxy, fluorine, chlorine, bromine, cyano and nitro,
preferred wherein
$R^2$ is substituted phenyl, substituted with 1–3 substituents selected from $C_{1-4}$-alkyl, $C_{1-4}$-alkoxy, fluorine, chlorine, bromine, cyano and nitro,
more preferred wherein
$R^2$ is substituted phenyl, substituted with 1–3 substituents selected from, chlorine and cyano,
most preferred wherein
$R^2$ is substituted phenyl, substituted with 1–3 substituents selected from chlorine and cyano;
$R^3$ is $C_{1-12}$-alkyl or $C_{1-4}$-alkoxy-$C_{1-4}$-alkyl,
preferred wherein
$R^3$ is $C_{1-7}$-alkyl or $C_{1-4}$-alkoxy-$C_{1-2}$-alkyl,
more preferred wherein
$R^3$ is $C_{1-7}$-alkyl or $C_{1-2}$-alkoxy-$C_{1-2}$-alkyl,
most preferred wherein
$R^3$ is $C_{1-7}$-alkyl;
A is a group selected from $CH_2$-(aryl-$C_{1-4}$-alkoxy), $CH_2$-(heterocyclyl-$C_{1-4}$-alkoxy), $C_{1-4}$-alkyl substituted with optionally substituted phenyl or with optionally substituted heterocyclyl,
wherein phenyl may be substituted with 1–5 substituents or heterocyclyl is substituted with 1–4 substituents and the substituents are selected from $C_{1-4}$-alkyl, $C_{1-4}$-alkoxy, hydroxy, fluorine, chlorine, bromine, cyano, S—$C_{1-4}$-alkyl and NRR', wherein R and R' are independently of each other hydrogen or $C_{1-4}$-alkyl; or A is a group of formula CH$_2$-U-heterocyclyl,
wherein U is O, S or NR", wherein R" is hydrogen or C$_{1-4}$-alkyl, and
wherein heterocyclyl is optionally substituted with 1–4 substituents selected from C$_{1-4}$-alkyl, fluorine, chlorine, bromine, cyano, nitro and NRR', wherein R and R' are independently of each other hydrogen or C$_{1-4}$-alkyl; or
A is a group of formula CH(V)heterocyclyl,
wherein V represents OH or F; or
A is a group of formula CH=CHW,
wherein W represents optionally substituted aryl, substituted with 1–5 substituents and the substituents are selected from C$_{1-4}$-alkyl, C$_{1-4}$-alkoxy,
hydroxy, cyano, fluorine, chlorine and bromine,
preferred wherein
A is a group selected from CH$_2$-(phenyl-C$_{1-2}$-alkoxy), CH$_2$-(pyridyl-C$_{1-2}$-alkoxy), C$_{1-2}$-alkyl substituted with optionally substituted phenyl or with optionally substituted heterocyclyl,
wherein phenyl maybe substituted with 1–3 substituents or heterocyclyl is substituted with 1–2 substituents and the substituents are selected from C$_{1-4}$-alkyl, C$_{1-4}$-alkoxy, hydroxy, fluorine, chlorine, bromine, cyano, S—C$_{1-4}$-alklyl and NRR', wherein R and R' are independently of each other hydrogen or C$_{1-4}$-alkyl; or
A is a group of formula CH$_2$-U-heterocyclyl,
wherein U is O, S or NR", wherein R" is hydrogen or C$_{1-4}$-alkyl, and
wherein heterocyclyl is optionally substituted with 1–2 substituents selected from C$_{1-4}$-alkyl, fluorine, chlorine, bromine, cyano, nitro and NRR', wherein R and R' are independently of each other hydrogen or C$_{1-4}$-alkyl; or
A is a group of formula CH(F)heterocyclyl,
more preferred wherein
A is a group selected from CH$_2$-(phenyl-C$_{1-2}$-alkoxy), CH$_2$-(pyridyl-C$_{1-2}$-alkoxy), C$_{1-2}$-alkyl substituted with optionally substituted phenyl or with optionally substituted heterocyclyl,
wherein phenyl may be substituted with 1–3 substituents or heterocyclyl is substituted with 1–2 substituents and the substituents are selected from C$_{1-2}$-alkyl) C$_{1-2}$-alkoxy, hydroxy, fluorine, chlorine, bromine, cyano, S—C$_{1-2}$-alkyl and NRR', wherein R and R' are independently of each other hydrogen or C$_{1-2}$-alkyl; or
A is a group of formula CH(F)Z,
wherein Z represents heterocyclyl,
most preferred wherein
A is a group selected from CH$_2$-(phenyl-C$_{1-2}$-alkoxy), CH$_2$-(pyridyl-C$_{1-2}$-alkoxy), C$_{1-2}$-alkyl substituted with optionally substituted heterocyclyl,
wherein heterocyclyl is substituted with 1–2 substituents and the substituents are selected from C$_{1-2}$-alkyl, C$_{1-2}$-alkoxy, hydroxy, fluorine, chlorine, bromine, cyano, S—C$_{1-2}$-alkyl and NRR', wherein R and R' are independently of each other hydrogen or C$_{1-2}$-alkyl;
X represents S or O;
for the treatment of diseases mediated by the human immunodeficiency virus (HIV) r for the preparation of a medicament for such treatment.

Further preferred embodiments of the invention is the use of compounds of formula I wherein
R$^1$ is C$_{1-4}$-alkyl,
preferred wherein
R$^1$ is ethyl or iso-propyl;
R$^2$ is substituted phenyl, substituted with 1–3 chlorine substituents,
preferred wherein
R$_2$ is 3,5-dichlorophenyl;
R$^3$ is C$_{1-4}$-alkyl,
preferred wherein
R$^3$ is methyl;
A is a group C$_{1-2}$-alkyl substituted with optionally substituted heterocyclyl,
wherein heterocyclyl is substituted with 1–2 substituents and the substituents are selected from C$_{1-2}$-alkyl and chlorine,
preferred wherein
A is a group C$_{1-2}$-alkyl substituted with optionally substituted heterocyclyl,
wherein heterocyclyl is substituted with 1–2 substituents and the substituents are selected from C$_{1-2}$-alkyl and chlorine;
X represents S or O.

A more preferred embodiment of the invention is the use of compounds of formula I wherein
X represents S.

Also part of the present invention is the use of compounds of formula I $$R^2-X\diagup\diagdown A$$
$$\diagdown_N\diagup$$
$$R^1\diagup N\diagdown R^3$$

R$^1$ is C$_{1-12}$-alkyl, C$_{3-8}$-cycloalkyl, acyl, C$_{1-4}$-alkylsulfonyl, optionally substituted phenylsulfonyl, aryl or C$_{1-4}$-alkyl substituted with optionally substituted phenyl,
wherein phenyl may be substituted with 1–5 substituents selected from C$_{1-4}$-alkyl, C$_{1-4}$-alkoxy, hydroxy, fluorine, chlorine and bromine;
R$_2$ is aryl or optionally substituted phenyl,
wherein phenyl maybe substituted with 1–5 substituents selected from C$_{1-4}$-alkyl, C$_{1-4}$-alkoxy, hydroxy, fluorine, chlorine and bromine;
R$^3$ is C$_{1-2}$-alkyl or C$_{1-4}$-alkoxy-C$_{1-4}$-alkyl;
A is a group selected from CH$_2$-(aryl-C$_{1-4}$-alkylamino), CH$_2$-(aryl-C$_{1-4}$-alkoxy),
C$_{1-4}$-alkyl substituted with optionally substituted aryl or with optionally substituted heterocyclyl,
wherein aryl may be substituted with 1–5 substituents or heterocyclyl is substituted with 1–4 substituents and the substituents are selected from C$_{1-4}$-alkyl, C$_{1-4}$-alkoxy, hydroxy, fluorine, chlorine and bromine; or
A is a group of formula CH(OH)Z,
wherein Z represents aryl or heterocyclyl; or
A is a group of formula CH=CHW,
wherein W represents optionally substituted aryl or optionally substituted heterocyclyl; and
wherein aryl may be substituted with 1–5 substituents or heterocyclyl may be substituted with 1–4 substituents and the substituents are selected from C$_{1-4}$-alkyl, C$_{1-4}$-alkoxy, hydroxy, fluorine, chlorine and bromine;
X represents S or O;
for the treatment of diseases mediated by the human immunodeficiency virus (HIV) or for the preparation of a medicament for such treatment.

More preferred embodiments for the use of compound of formula I for the treatment of diseases mediated by the human immunodeficiency virus (HIV) or for the preparation of a medicament for such treatment are set out in table 1 (see below):

TABLE 1

| STRUCTURE | SYSTEMATIC NAME |
|---|---|
| 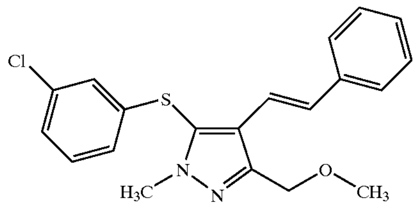 | 5-(3-Chlorophenylthio)-3-methoxymethyl-1-methyl-4-styryl-1H-pyrazole |
| 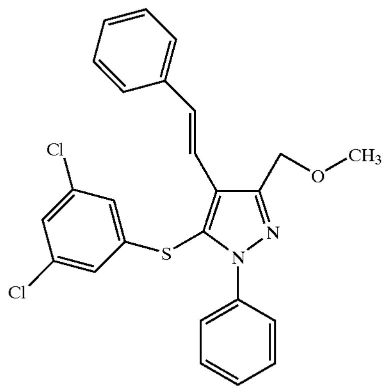 | (E)-5-(3,5-Dichlorophenylthio)-3-(methoxymethyl)-1-phenyl-4-styryl-1H-pyrazole |
| 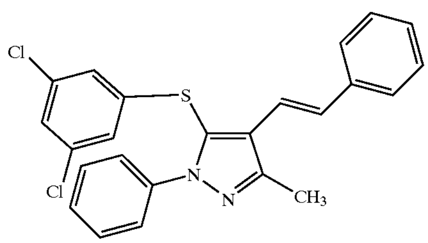 | 5-(3,5-Dichlorophenylthio)-3-methyl-1-phenyl-4-styryl-1H-pyrazole |
| 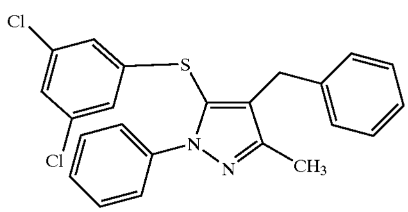 | 4-Benzyl-5-(3,5-dichlorophenylthio)-3-methyl-1-phenyl-1H-pyrazole |
| 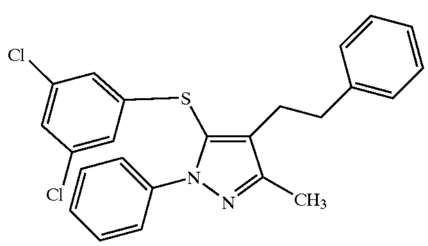 | 5-(3,5-Dichlorophenylthio)-3-methyl-4-(2-phenylethyl)-1-phenyl-1H-pyrazole |

TABLE 1-continued

| STRUCTURE | SYSTEMATIC NAME |
|---|---|
| 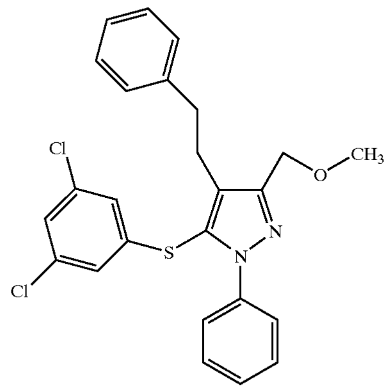 | 5-(3,5-Dichlorophenylthio)-3-(methoxymethyl)-1-phenyl-4-(2-phenylethyl)-1H-pyrazole |
| 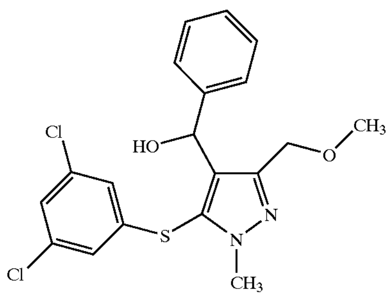 | [5-(3,5-Dichlorophenylthio)-3-(methoxymethyl)-1-methyl-1H-pyrazol-4-yl]-phenyl-methanol |
| 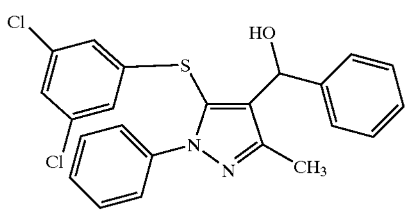 | [5-(3,5-Dichlorophenylthio)-3-methyl-1-phenyl-1H-pyrazol-4-yl]-phenyl-methanol |
| 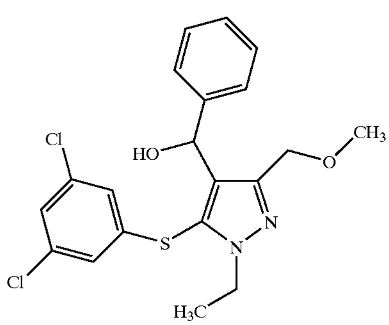 | [5-(3,5-Dichlorophenylthio)-1-ethyl-3-(methoxymethyl)-1H-pyrazol-4-yl]-phenyl-methanol |
| 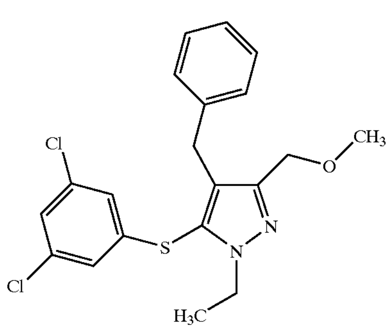 | 4-Benzyl-5-(3,5-dichlorophenylthio)-1-ethyl-3-(methoxymethyl)-1H-pyrazole |

TABLE 1-continued

| STRUCTURE | SYSTEMATIC NAME |
|---|---|
|  | 4-Benzyl-5-(3,5-dichloro-phenylthio)-3-methoxymethyl-1-methyl-1H-pyrazole |
| 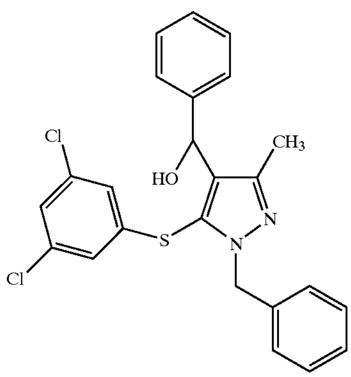 | 5-(3,5-Dichlorophenylthio)-3-methyl-alpha(RS)-phenyl-1H-pyrazole-4-methanol |
| 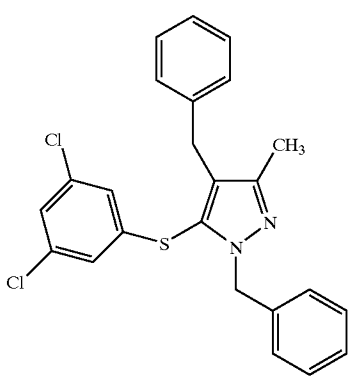 | 1,4-Dibenzyl-5-(3,5-dichlorophenylthio)-3-methyl-1H-pyrazole |
| 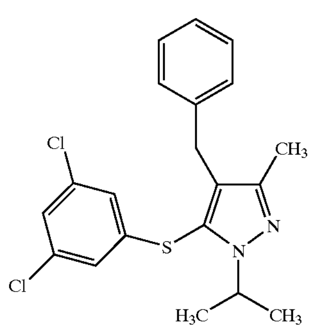 | 4-Benzyl-5-(3,5-dichloro-phenylthio)-1-isopropyl-3-methyl-1H-pyrazole |

TABLE 1-continued

| STRUCTURE | SYSTEMATIC NAME |
|---|---|
| 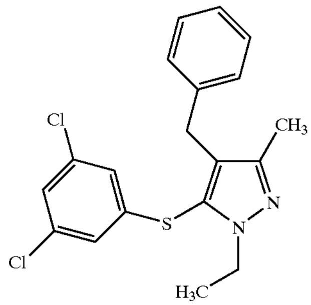 | 4-Benzyl-5-(3,5-dichlorophenylthio)-1-ethyl-3-methyl-1H-pyrazole |
| 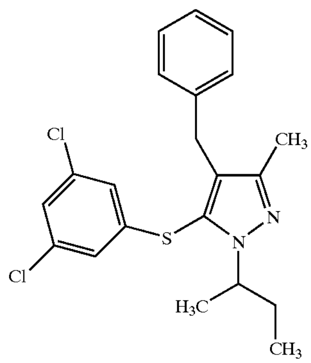 | 4-Benzyl-1-sec-butyl-5-(3,5-dichlorophenylthio)-3-methyl-1H-pyrazole |
| 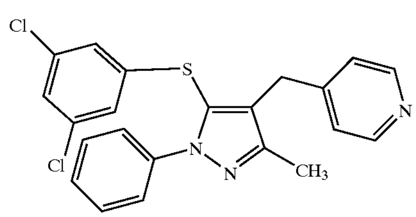 | 4-[5-(3,5-Dichlorophenylthio)-3-methyl-1-phenyl-4-[(4-pyridyl)methyl]-1H-pyrazole |
| 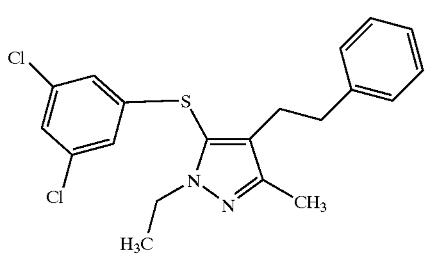 | 5-(3,5-Dichlorophenylthio)-1-ethyl-3-methyl-4-(2-phenylethyl)-1H-pyrazole |
| 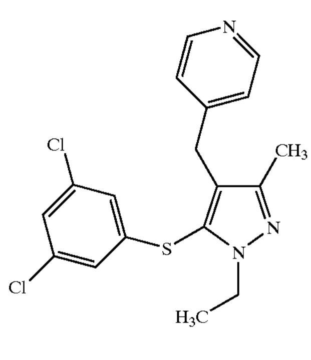 | 4-[5-(3,5-Dichlorophenylthio)-1-ethyl-3-methyl-[(4-pyridyl)methyl]-1H-pyrazole |

TABLE 1-continued

| STRUCTURE | SYSTEMATIC NAME |
| --- | --- |
| 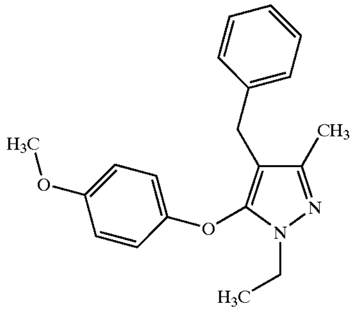 | 4-Benzyl-1-ethyl-5-(4-methoxyphenoxy-3-methyl-1H-pyrazole |
| 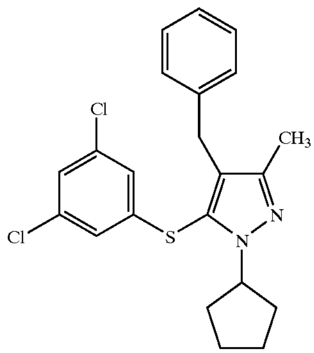 | 4-Benzyl-1-cyclopentyl-5-(3,5-dichlorophenylthio)-3-methyl-1H-pyrazole |
| 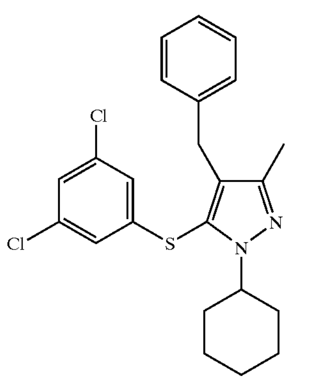 | 4-Benzyl-1-cyclohexyl-5-(3,5-dichlorophenylthio)-3-methyl-1H-pyrazole |
| 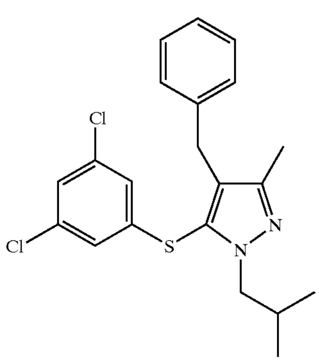 | 4-Benzyl-5-(3,5-dichlorophenylthio)-1-isobutyl-3-methyl-1H-pyrazole |

TABLE 1-continued

| STRUCTURE | SYSTEMATIC NAME |
|---|---|
| 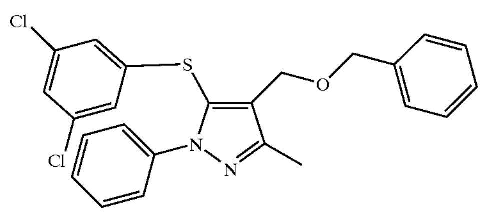 | 4-Benzyloxymethyl-5-(3,5-dichlorophenylthio)-3-methyl-1-phenyl-1H-pyrazole |
| 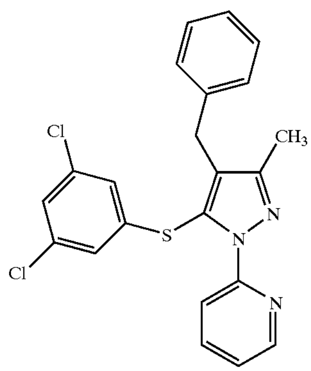 | 2-[4-Benzyl-5-(3,5-dichloro-phenylsulfanyl)-3-methyl-pyrazol-1-yl]-pyridine |
| 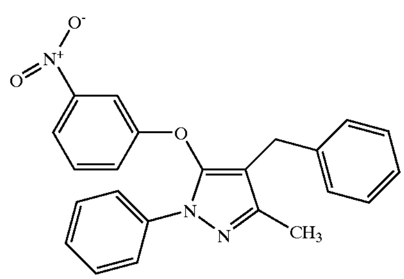 | 4-Benzyl-3-methyl-5-(3-nitro-phenoxy)-1-phenyl-1H-pyrazole |
| 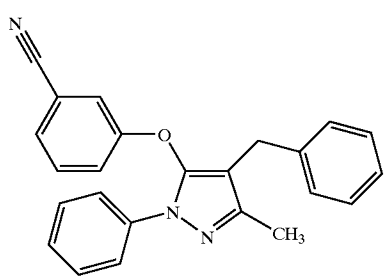 | 3-(4-Benzyl-5-methyl-2-phenyl-2H-pyrazol-3-yloxy)-benzonitrile |
| 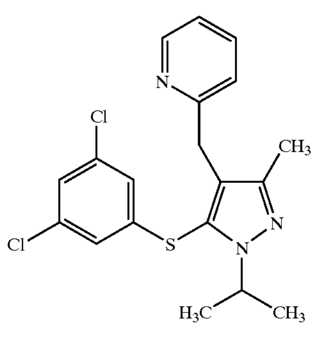 | 2-[5-(3,5-Dichloro-phenylsulfanyl)-1-isopropyl-3-methyl-1H-pyrazol-4-ylmethyl]-pyridine |

TABLE 1-continued

| STRUCTURE | SYSTEMATIC NAME |
|---|---|
| 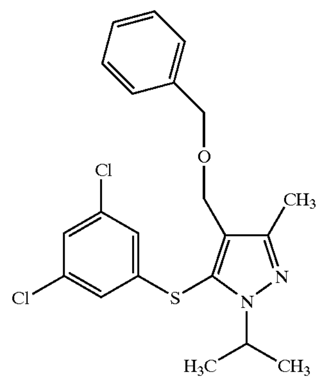 | 4-Benzyloxymethyl-5-(3,5-dichloro-phenylsulfanyl)-1-isopropyl-3-methyl-1H-pyrazole |
| 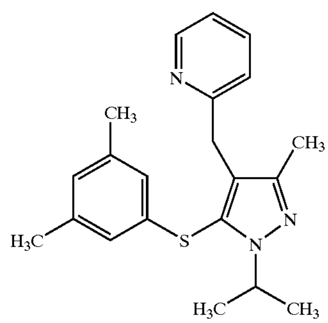 | 2-[5-(3,5-Dimethyl-phenylsulfanyl)-1-isopropyl-3-methyl-1H-pyrazol-4-ylmethyl]-pyridine |
| 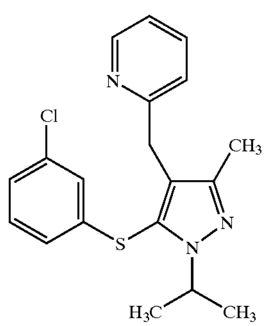 | 2-[5-(3-Chloro-phenylsulfanyl)-1-isopropyl-3-methyl-1H-pyrazol-4-ylmethyl]-pyridine |
| 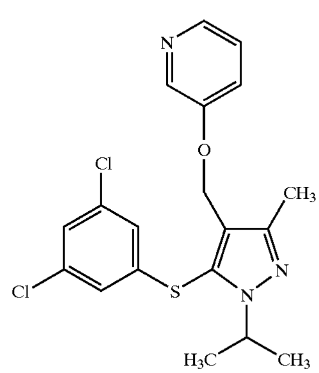 | 2-[5-(3,5-Dichloro-phenylsulfanyl)-1-isopropyl-3-methyl-1H-pyrazol-4-ylmethoxy]-pyridine |

TABLE 1-continued

| STRUCTURE | SYSTEMATIC NAME |
| --- | --- |
| 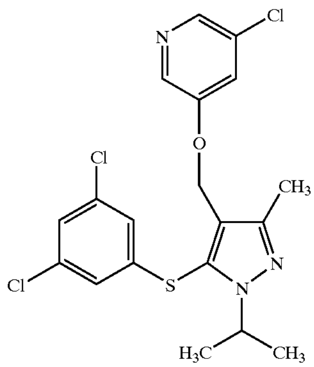 | 3-Chloro-5-[5-(3,5-dichloro-phenylsulfanyl)-1-isopropyl-3-methyl-1H-pyrazol-4-ylmethoxy]-pyridine |
| 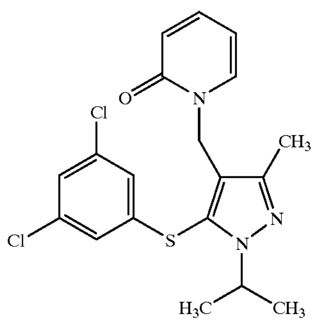 | 1-[5-(3,5-Dichloro-phenylsulfanyl)-1-isopropyl-3-methyl-1H-pyrazol-4-ylmethyl]-1H-pyridin-2-one |
| 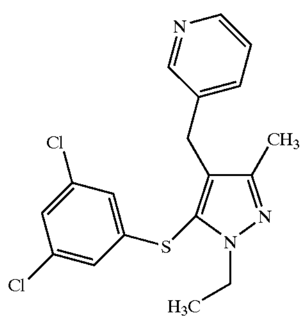 | 3-[5-(3,5-Dichloro-phenylsulfanyl)-1-ethyl-3-methyl-1H-pyrazol-4-ylmethyl]-pyridine |
| 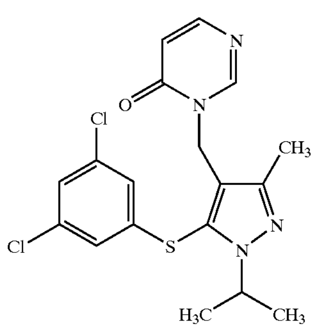 | 3-[5-(3,5-Dichloro-phenylsulfanyl)-1-isopropyl-3-methyl-1H-pyrazol-4-ylmethyl]-3H-pyrimidin-4-one |

TABLE 1-continued

| STRUCTURE | SYSTEMATIC NAME |
|---|---|
| 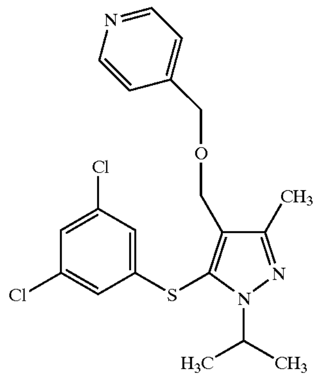 | 4-[5-(3,5-Dichloro-phenylsulfanyl)-1-isopropyl-3-methyl-1H-pyrazol-4-ylmethoxymethyl]-pyridine |
| | 3-(4-Benzyl-5-methyl-2-phenyl-2H-pyrazol-3-ylsulfanyl)-benzonitrile |
| 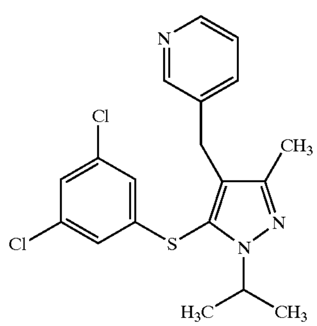 | 3-[5-(3,5-Dichloro-phenylsulfanyl)-1-isopropyl-3-methyl-1H-pyrazol-4-ylmethyl]-pyridine |
| 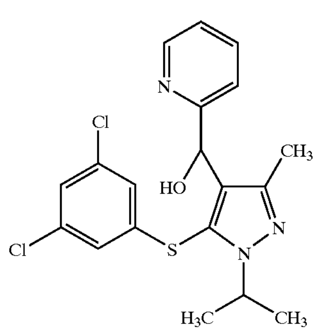 | [5-(3,5-Dichloro-phenylsulfanyl)-1-isopropyl-3-methyl-1H-pyrazol-4-yl]-pyridin-2-yl-methanol |

TABLE 1-continued

| STRUCTURE | SYSTEMATIC NAME |
|---|---|
| 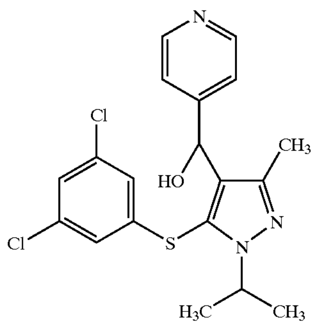 | [5-(3,5-Dichloro-phenylsulfanyl)-1-isopropyl-3-methyl-1H-pyrazol-4-yl]-pyridin-4-yl-methanol |
| 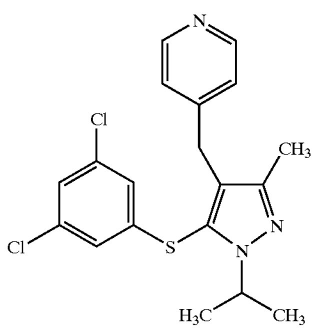 | 4-[5-(3,5-Dichloro-phenylsulfanyl)-1-isopropyl-3-methyl-1H-pyrazol-4-ylmethyl]-pyridine |
| 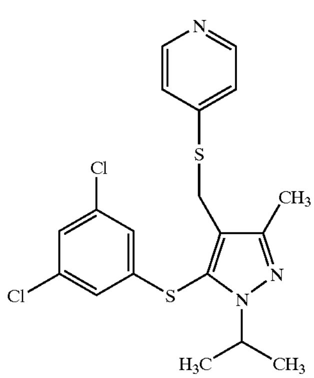 | 4-[5-(3,5-Dicbloro-phenylsulfanyl)-1-isopropyl-3-methyl-1H-pyrazol-4-ylmethylsulfanyl]-pyridine |
| 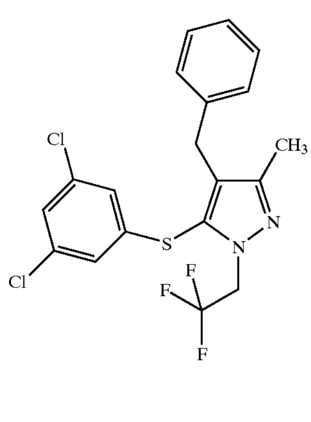 | 4-Benzyl-5-(3,5-dichloro-phenylsulfanyl)-3-methyl-1-(2,2,2-trifluoro-ethyl)-1H-pyrazole |

TABLE 1-continued

| STRUCTURE | SYSTEMATIC NAME |
|---|---|
| 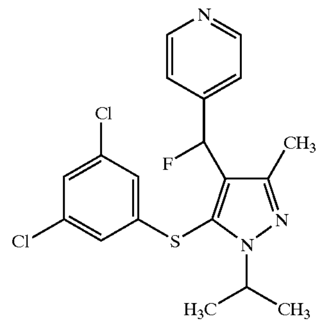 | 4-{[5-(3,5-Dichloro-phenylsulfanyl)-1-isopropyl-3-methyl-1H-pyrazol-4-yl]-fluoro-methyl}-pyridine |
| 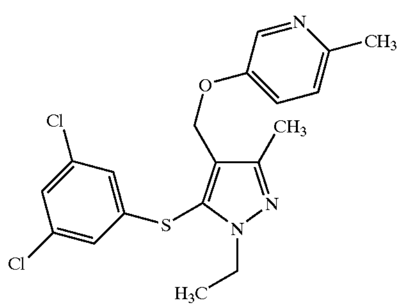 | 5-[5-(3,5-Dichloro-phenylsulfanyl)-1-ethyl-3-methyl-1H-pyrazol-4-ylmethoxy]-2-methyl-pyridine |
| 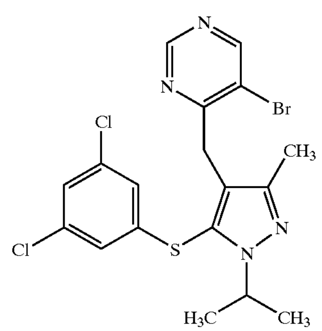 | 5-Bromo-4-[5-(3,5-dichloro-phenylsulfanyl)-1-isopropyl-3-methyl-1H-pyrazol-4-ylmethyl]-pyrimidine |
| 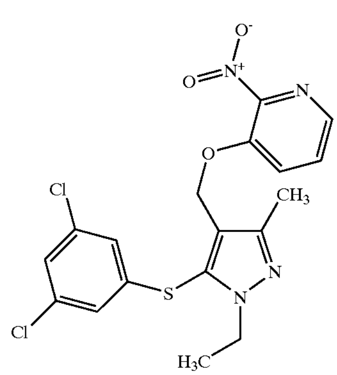 | 3-[5-(3,5-Dichloro-phenylsulfanyl)-1-ethyl-3-methyl-1H-pyrazol-4-ylmethoxy]-2-nitro-pyridine |

TABLE 1-continued

| STRUCTURE | SYSTEMATIC NAME |
| --- | --- |
| 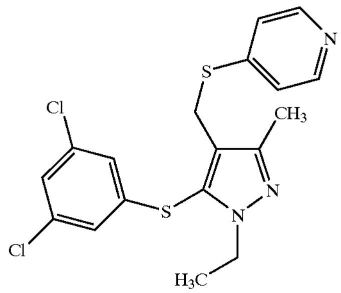 | 4-[5-(3,5-Dichloro-phenylsulfanyl)-1-ethyl-3-methyl-1H-pyrazol-4-ylmethylsulfanyl]-pyridine |
| 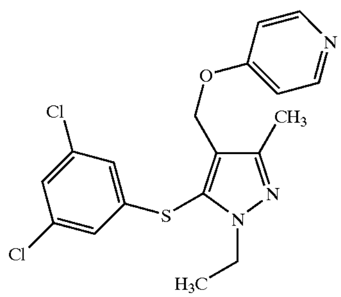 | 4-[5-(3,5-Dichloro-phenylsulfanyl)-1-ethyl-3-methyl-1H-pyrazol-4-ylmethoxy]-pyridine |
| 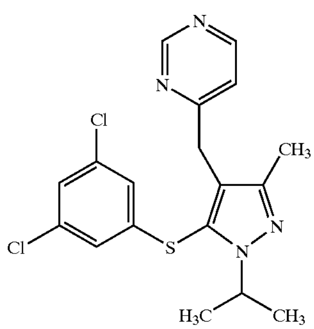 | 4-[5-(3,5-Dichloro-phenylsulfanyl)-1-isopropyl-3-methyl-1H-pyrazol-4-ylmethyl]-pyrimidine |
| 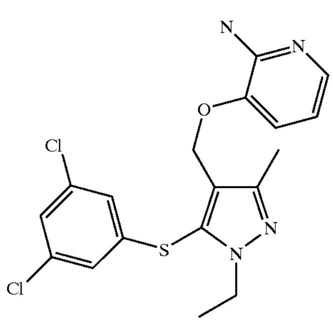 | 3-[5-(3,5-Dichloro-phenylsulfanyl)-1-ethyl-3-methyl-1H-pyrazol-4-ylmethoxy]-pyridin-2-ylamine |

TABLE 1-continued

| STRUCTURE | SYSTEMATIC NAME |
| --- | --- |
| 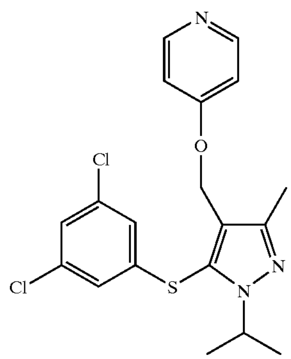 | 4-[5-(3,5-Dichloro-phenylsulfanyl)-1-isopropyl-3-methyl-1H-pyrazol-4-ylmethoxy]-pyridine |
| 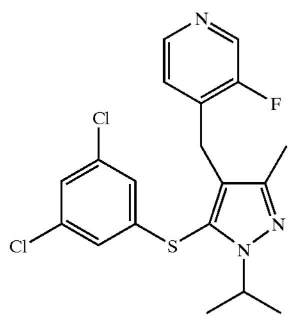 | 4-[5-(3,5-Dichloro-phenylsulfanyl)-1-isopropyl-3-methyl-1H-pyrazol-4-ylmethyl]-3-fluoro-pyridine |
| 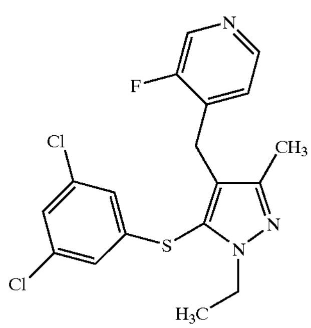 | 4-[5-(3,5-Dichloro-phenylsulfanyl)-1-ethyl-3-methyl-1H-pyrazol-4-ylmethyl]-3-fluoro-pyridine |
| 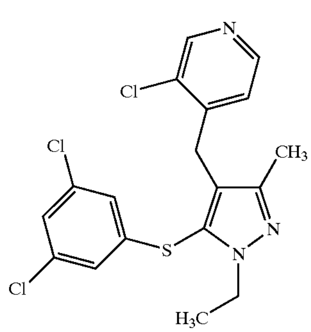 | 3-Chloro-4-[5-(3,5-dichloro-phenylsulfanyl)-1-ethyl-3-methyl-1H-pyrazol-4-ylmethyl]-pyridine |

TABLE 1-continued

| STRUCTURE | SYSTEMATIC NAME |
|---|---|
| 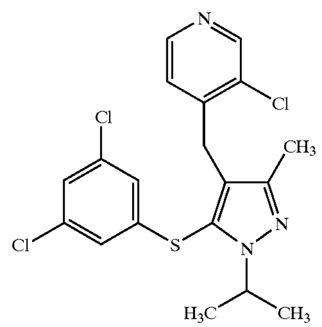 | 3-Chloro-4-[5-(3,5-dichloro-phenylsulfanyl)-1-isopropyl-3-methyl-1H-pyrazol-4-ylmethyl]-pyridine |
| 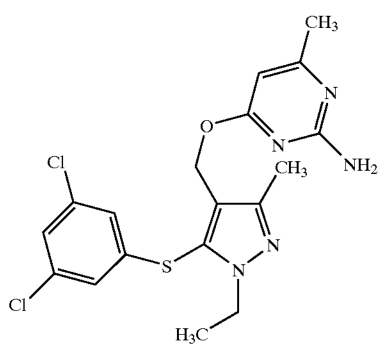 | 4-[5-(3,5-Dichloro-phenylsulfanyl)-1-ethyl-3-methyl-1H-pyrazol-4-ylmethoxy]-6-methyl-pyrimidin-2-ylamine |
| 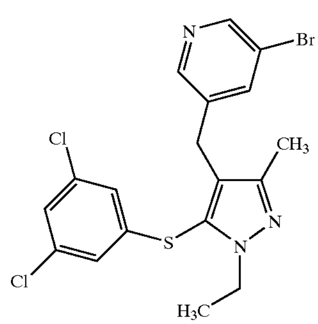 | 3-Bromo-5-[5-(3,5-dichloro-phenylsulfanyl)-1-ethyl-3-methyl-1H-pyrazol-4-ylmethyl]-pyridine |
| 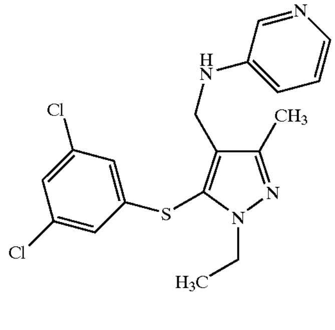 | [5-(3,5-Dichloro-phenylsulfanyl)-1-ethyl-3-methyl-1H-pyrazol-4-ylmethyl]-pyridin-3-yl-amine |

TABLE 1-continued

| STRUCTURE | SYSTEMATIC NAME |
| --- | --- |
| 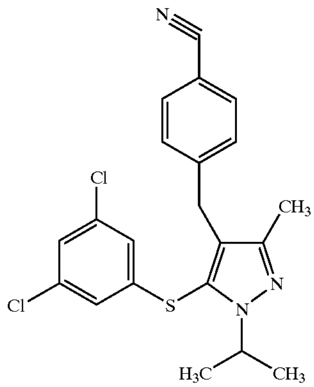 | 4-[5-(3,5-Dichloro-phenylsulfanyl)-1-isopropyl-3-methyl-1H-pyrazol-4-ylmethyl]-benzonitrile |
| 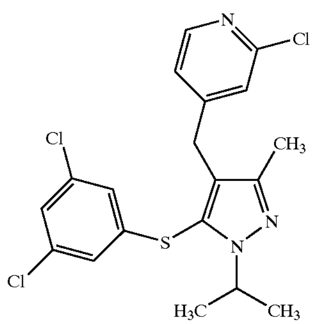 | 2-Chloro-4-[5-(3,5-dichloro-phenylsulfanyl)-1-isopropyl-3-methyl-1H-pyrazol-4-ylmethyl]-pyridine |
| 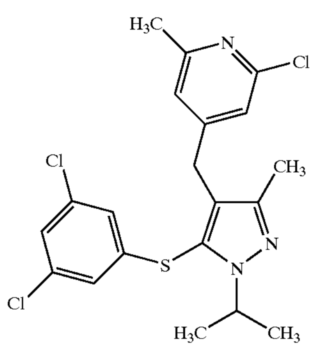 | 2-Chloro-4-[5-(3,5-dichloro-phenylsulfanyl)-1-isopropyl-3-methyl-1H-pyrazol-4-ylmethyl]-6-methyl-pyridine |
| 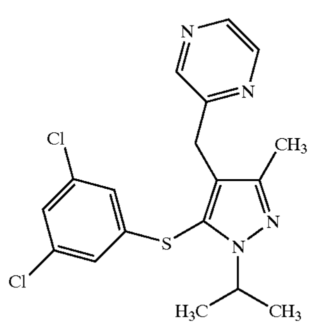 | 2-[5-(3,5-Dichloro-phenylsulfanyl)-1-isopropyl-3-methyl-1H-pyrazol-4-ylmethyl]-pyrazine |

TABLE 1-continued

| STRUCTURE | SYSTEMATIC NAME |
|---|---|
| 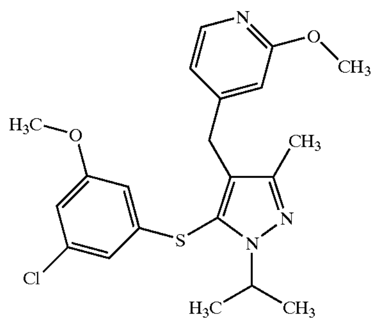 | 4-[5-(3-Chloro-5-methoxy-phenylsulfanyl)-1-isopropyl-3-methyl-1H-pyrazol-4-ylmethyl]-2-methoxy-pyridine |
| 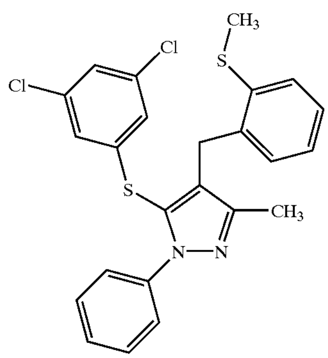 | 3-[[5-(3,5-Dichlorophenylthio)-3-methyl-1-phenyl-1H-pyrazol-4-yl]methyl]-2-(methylthio)pyridine |
| 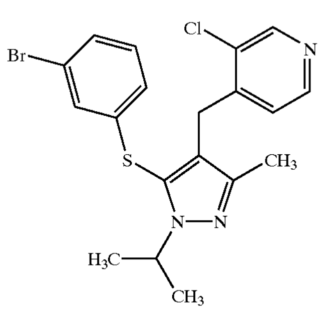 | 4-[5-(3-Bromo-phenylsulfanyl)-1-isopropyl-3-methyl-1H-pyrazol-4-ylmethyl]-3-chloro-pyridine |
| 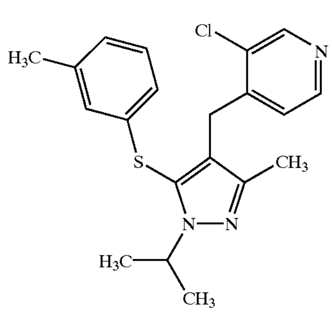 | 3-Chloro-4-(1-isopropyl-3-methyl-5-m-tolylsulfanyl-1H-pyrazol-4-ylmethyl)-pyridine |

TABLE 1-continued

| STRUCTURE | SYSTEMATIC NAME |
| --- | --- |
| 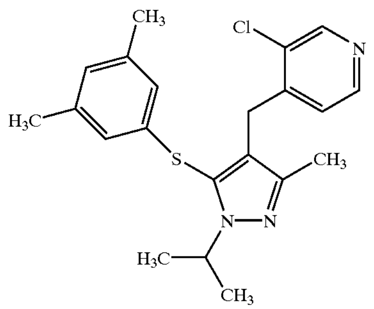 | 3-Chloro-4-[5-(3,5-dimethyl-phenylsulfanyl)-1-isopropyl-3-methyl-1H-pyrazol-4-ylmethyl]-pyridine |
| 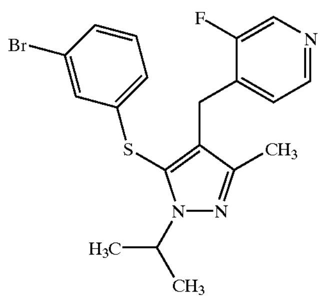 | 4-[5-(3-Bromo-phenylsulfanyl)-1-isopropyl-3-methyl-1H-pyrazol-4-ylmethyl]-3-fluoro-pyridine |
| 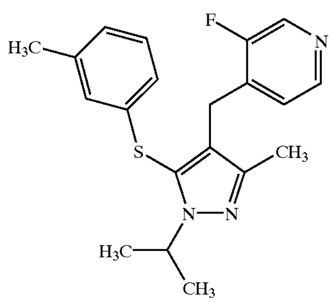 | 3-Fluoro-4-(1-isopropyl-3-methyl-5-m-tolylsulfanyl-1H-pyrazol-4-ylmethyl)-pyridine |
| 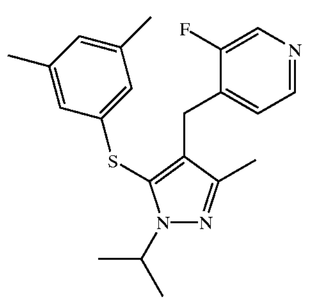 | 4-[5-(3,5-Dimethyl-phenylsulfanyl)-1-isopropyl-3-methyl-1H-pyrazol-4-ylmethyl]-3-fluoro-pyridine |
| 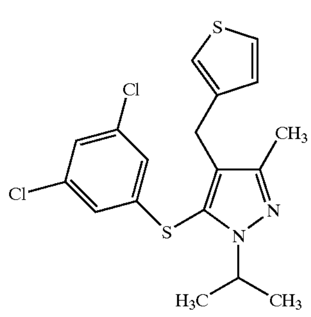 | 5-(3,5-Dichloro-phenylsulfanyl)-1-isopropyl-3-methyl-4-thiophen-3-ylmethyl-1H-pyrazole |

TABLE 1-continued

| STRUCTURE | SYSTEMATIC NAME |
|---|---|
| 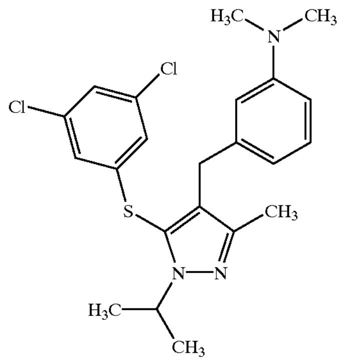 | {3-[5-(3,5-Dichloro-phenylsulfanyl)-1-isopropyl-3-methyl-1H-pyrazol-4-ylmethyl]-phenyl}-dimethyl-amine |
| 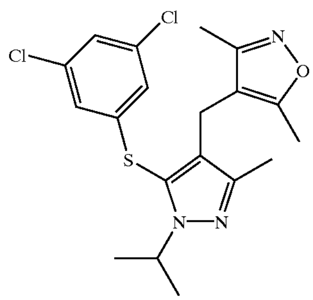 | 4-[5-(3,5-Dichloro-phenylsulfanyl)-1-isopropyl-3-methyl-1H-pyrazol-4-ylmethyl]-3,5-dimethyl-isoxazole |
| 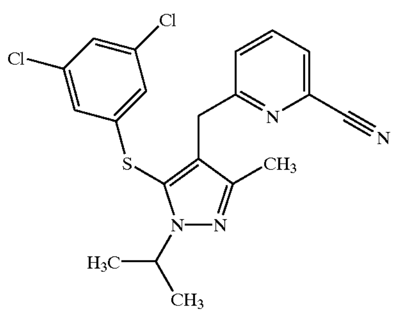 | 6-[5-(3,5-Dichloro-phenylsulfanyl)-1-isopropyl-3-methyl-1H-pyrazol-4-ylmethyl]-pyridine-2-carbonitrile |

Also part of the present invention are novel pyrazole derivatives, a process for their manufacture, pharmaceutical compositions and the use of such compounds in medicine. In particular, the compounds are inhibitors of the human immunodeficiency virus reverse transcriptase enzyme which is involved in viral replication.

The novel compounds of this invention are compounds of formula I-A

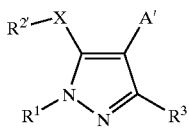

I-A wherein $R^1$ is optionally substituted $C_{1-12}$-alkyl, $C_{3-8}$-cycloalkyl, acyl, $C_{1-4}$-alkylsulfonyl, optionally substituted phenylsulfonyl, aryl, heterocyclyl or $C_{1-4}$-alkyl substituted with phenyl, wherein $C_{1-2}$-alkyl maybe substituted with 1–5 substituents selected from fluorine, chlorine and bromine, and wherein phenyl may be substituted with 1–5 substituents selected from $C_{1-4}$-alkyl, $C_{1-4}$-alkoxy, hydroxy, fluorine, chlorine, bromine and cyano;

$R^{2'}$ is optionally substituted phenyl;

wherein phenyl may be substituted with 1–5 substituents selected from $C_{1-4}$-alkyl, $C_{1-4}$-alkoxy, hydroxy, fluorine, chlorine, bromine, cyano and nitro;

$R^3$ is $C_{1-2}$-alkyl or $C_{1-4}$-alkoxy-$C_{1-4}$-alkyl;

A' is a group selected from $CH_2$-(aryl-$C_{1-4}$-alkylamino), $CH_2$-(aryl-$C_{1-4}$-alkoxy), $CH_2$-(heterocyclyl-$C_{1-4}$-alkoxy), $C_{1-4}$-alkyl substituted with optionally substituted aryl or with optionally substituted 4-pyridyl, wherein aryl may be substituted with 1–5 substituents or 4-pyridyl is substituted with 1–4 substituents and the substituents are selected from $C_{1-4}$-alkyl, $C_{1-4}$-alkoxy, hydroxy, fluorine, chlorine, bromine, cyano, S—$C_{1-4}$-alkyl and NRR', wherein R and R' are independently of each other hydrogen or $C_{1-4}$-alkyl; or A' is a group of formula $CH_2$-U-heterocyclyl, wherein U is O, S or NR", wherein R" is hydrogen or $C_{1-4}$-alkyl, and wherein heterocyclyl is optionally substituted with 1–4 substituents selected from $C_{1-4}$-alkyl, fluorine, chlorine, bromine, cyano, nitro and NRR', wherein R and R' are independently of each other hydrogen or $C_{1-4}$-alkyl; or A' is a group of formula CH(OH)aryl; or A' is a group of formula CH=CHW wherein W represents optionally substituted aryl or optionally substituted heterocyclyl; and wherein aryl may be substituted with 1–5 substituents or heterocyclyl may be substituted with 1–4 substituents and the substituents are selected from $C_{1-4}$-alkyl, $C_{1-4}$-alkoxy, hydroxy, cyano, fluorine, chlorine and bromine;

X represents S or O;

hydrolyzable esters or ethers thereof, and pharmaceutically acceptable salts thereof.

The terms used for the substituents of novel pyrazole derivatives are as defined above.

Further embodiments of the invention are novel compounds of formula I-A wherein $R^1$ is optionally substituted $C_{1-2}$-alkyl, $C_{3-8}$-cycloalkyl, aryl, heterocyclyl or $C_{1-4}$-alkyl substituted with phenyl, wherein $C_{1-12}$-alkyl maybe substituted with 1–5 fluorine substituents, preferred wherein $R^1$ is optionally substituted $C_{1-7}$-alkyl, $C_{3-8}$-cycloalkyl, aryl, heterocyclyl or $C_{1-4}$-alkyl substituted with optionally substituted phenyl, wherein $C_{1-7}$-alkyl may be substituted with 1–3 fluorine substituents, more preferred wherein $R^1$ is optionally substituted $C_{1-7}$-alkyl, $C_{3-8}$-cycloalkyl, phenyl, pyridyl or benzyl, wherein $C_{1-7}$-alkyl may be substituted with 1–3 fluorine substituents, most preferred wherein R' is $C_{1-7}$-alkyl;

$R^{2'}$ is substituted phenyl, substituted with 1–5 substituents selected from $C_{1-4}$-alkyl, $C_{1-4}$-alkoxy, fluorine, chlorine, bromine, cyano and nitro, preferred wherein $R^{2'}$ is substituted phenyl, substituted with 1–3 substituents selected from $C_{1-4}$-alkyl, $C_{1-4}$-alkoxy, fluorine, chlorine, bromine, cyano and nitro, more preferred wherein $R^{2'}$ is substituted phenyl, substituted with 1–3 substituents selected from $C_{1-2}$-alkyl, fluorine, chlorine and cyano, most preferred wherein $R^{2''}$ is substituted phenyl, substituted with 1–3 substituents selected from chlorine and cyano;

$R^3$ is $C_{1-12}$-alkyl or $C_{1-4}$-alkoxy-$C_{1-4}$-alcyl, preferred wherein $R^3$ is $C_{1-7}$-alkyl or $C_{1-4}$-alkoxy-$C_{1-2}$-alkyl, more preferred wherein $R^3$ is $C_{1-7}$-alkyl or $C_{1-2}$-alkoxy-$C_{1-2}$-alkyl, most preferred wherein $R^3$ is $C_{1-7}$-alkyl;

A' is a group selected from $CH_2$-(phenyl-$C_{1-4}$-alkoxy), $CH_2$-(pyridyl-$C_{1-4}$-alkoxy), $C_{1-4}$-alkyl substituted with optionally substituted aryl or with optionally substituted 4-pyridyl, wherein aryl may be substituted with 1–5 substituents or 4-pyridyl is substituted with 1–4 substituents and the substituents are selected from $C_{1-4}$-alkyl, $C_{1-4}$-alkoxy, hydroxy, fluorine, chlorine, bromine, cyano, S—$C_{1-4}$-alkyl and NRR', wherein R and R' are independently of each other hydrogen or $C_{1-4}$-alkyl; or A' is a group of formula $CH_2$-U-heterocyclyl, wherein U is O, S or NR'', wherein R'' is hydrogen or $C_{1-4}$-alkyl, and wherein heterocyclyl is optionally substituted with 1–4 substituents selected from $C_{1-4}$-alkyl, fluorine, chlorine, bromine, cyano, nitro and NRR', wherein R and R' are independently of each other hydrogen or $C_{1-4}$-alkyl; or A' is a group of formula CH(OH)aryl; or A' is a group of formula CH=CHW wherein W represents optionally substituted aryl, substituted with 1–5 substituents and the substituents are selected from $C_{1-4}$-alkyl, $C_{1-4}$-alkoxy, hydroxy, cyano, fluorine, chlorine and bromine, preferred wherein A' is a group selected from $CH_2$-(phenyl-$C_{1-2}$-alkoxy), $CH_2$-(pyridyl-$C_{1-2}$-alkoxy), methyl substituted with optionally substituted phenyl or with optionally substituted 4-pyridyl, wherein phenyl may be substituted with 1–3 substituents or 4-pyridyl is substituted with 1–2 substituents and the substituents are selected from $C_{1-4}$-alkyl, $C_{1-4}$-alkoxy, hydroxy, fluorine, chlorine, bromine, cyano, S—$C_{1-4}$-alkyl and NRR', wherein R and R' are independently of each other hydrogen or $C_{1-4}$-alkyl; or A' is a group of formula $CH_2$-U-heterocyclyl, wherein U is O, S or NR'', wherein R'' is hydrogen or $C_{1-4}$-alkyl, and wherein heterocyclyl is optionally substituted with 1–2 substituents selected from $C_{1-4}$-alkyl, fluorine, chlorine, bromine, cyano, nitro and NRR', wherein R and R' are independently of each other hydrogen or $C_{1-4}$-alkyl, more preferred wherein A' is a group selected from $CH_2$-(phenyl-$C_{1-2}$-alkoxy), $CH_2$-(pyridyl-$C_{1-2}$-alkoxy), methyl substituted with optionally substituted phenyl or with optionally substituted 4-pyridyl, wherein phenyl may be substituted with 1–3 substituents or 4-pyridyl is substituted with 1–2 substituents and the substituents are selected from $C_{1-2}$-alkyl, $C_{1-2}$-alkoxy, hydroxy, fluorine, chlorine, bromine, cyano, S—$C_{1-2}$-alkyl and NRR', wherein R and R' are independently of each other hydrogen or $C_{1-2}$-alkyl, most preferred wherein A' is a group selected from $CH_2$-(aryl-$C_{1-2}$-alkoxy), $CH_2$-(heterocyclyl-$C_{1-2}$-alkoxy), methyl substituted optionally substituted 4-pyridyl, wherein 4-pyridyl is substituted with 1–2 substituents and the substituents are selected from $C_{1-2}$-alkyl, $C_{1-2}$-alkoxy, hydroxy, fluorine, chlorine, bromine, cyano, S—$C_{1-2}$-alkyl and NRR', wherein R and R' are independently of each other hydrogen or $C_{1-2}$-alkyl;

X represents S or O;

hydrolyzable esters or ethers thereof, and pharmaceutically acceptable salts thereof Another preferred embodiment of the invention are novel compounds of formula I-A wherein $R^1$ is $C_{1-4}$-alkyl;

$R^{2'}$ is substituted phenyl, substituted with 1–3 chlorine substituents;

$R^3$ is $C_{1-4}$-alkyl;

A' is a group methyl substituted optionally substituted 4-pyridyl, wherein 4-pyridyl is substituted with 1–2 substituents and the substituents are selected from $C_{1-2}$-alkyl and chlorine;

X represents S or O;

hydrolyzable esters or ethers thereof, and pharmaceutically acceptable salts thereof.

A further preferred embodiment of the invention are novel compounds of formula I-A wherein $R^1$ is $C_{1-12}$-alkyl, $C_{3-8}$-cycloalkyl, acyl, $C_{1-4}$-alkylsulfonyl, optionally substituted phenylsulfonyl, aryl or $C_{1-4}$-alkyl substituted with optionally substituted phenyl wherein phenyl may be substituted with 1–5 substituents selected from $C_{1-4}$-alkyl, $C_{1-4}$-alkoxy, hydroxy, fluorine, chlorine or bromine;

$R^2$ is optionally substituted phenyl;

wherein phenyl may be substituted with 1–5 substituents selected from $C_{1-4}$-alkyl, $C_{1-4}$-alkoxy, hydroxy, fluorine, chlorine or bromine;

$R^3$ is $C_{1-2}$-alkyl or $C_{1-4}$-alkoxy-$C_{1-4}$-alkyl;

A' is a group selected from $CH_2$-(aryl-$C_{1-4}$-alkylamino), $CH_2$-(aryl-$C_{1-4}$-alkoxy), $C_{1-4}$-alkyl substituted with optionally substituted aryl or with optionally substituted 4-pyridyl wherein aryl may be substituted with 1–5 substituents or 4-pyridyl is substituted with 1–4 substituents and the substituents are selected from $C_{1-4}$-alkyl, $C_{1-4}$-alkoxy, hydroxy, fluorine, chlorine or bromine; or A' is a group of formula CH(OH)Z' wherein Z' represents aryl; or

A' is a group of formula CH=CHW wherein W represents optionally substituted aryl or optionally substituted heterocyclyl; and wherein aryl may be substituted with 1–5 substituents or heterocyclyl may be substituted with 1–4 substituents and the substituents are selected from $C_{1-4}$-alkyl, $C_{1-4}$-alkoxy, hydroxy, fluorine, chlorine or bromine;

X represents S or O;

hydrolyzable esters or ethers thereof, and pharmaceutically acceptable salts thereof.

A preferred embodiment of the invention are novel compounds of formula I-A wherein A' is a group selected from $CH_2$-(aryl-$C_{1-4}$-alkylamino), $CH_2$-(aryl-$C_{1-4}$-alkoxy), $CH_2$-(heterocyclyl-$C_{1-4}$-alkoxy), $C_{1-4}$-alkyl substituted with optionally substituted, wherein aryl may be substituted with 1–5 substituents and the substituents are selected from $C_{1-4}$-alkyl, $C_{1-4}$-alkoxy, hydroxy, fluorine, chlorine, bromine, cyano, S—$C_{1-4}$-alkyl and NRR', wherein R and R' are independently of each other hydrogen or $C_{1-4}$-alkyl; or A' is a group of formula $CH_2$-U-heterocyclyl, wherein U is O, S or NR", wherein R" is hydrogen or $C_{1-4}$-alkyl, and wherein heterocyclyl is optionally substituted with 1–4 substituents selected from $C_{1-4}$-alkyl, fluorine, chlorine, bromine, cyano, nitro and NRR', wherein R and R' are independently of each other hydrogen or $C_{1-4}$-alkyl; or A' is a group of formula CH(OH)aryl; or A' is a group of formula CH=CHW wherein W represents optionally substituted aryl or optionally substituted heterocyclyl; and wherein aryl may be substituted with 1–5 substituents or heterocyclyl may be substituted with 1–4 substituents and the substituents are selected from $C_{1-4}$-alkyl, $C_{1-4}$-alkoxy, hydroxy, cyano, fluorine, chlorine and bromine;

X represents S or O;

hydrolyzable esters or ethers thereof, and pharmaceutically acceptable salts thereof An especially preferred embodiment of the invention are novel compounds of formula I-A wherein X represents S.

More preferred embodiments of the invention are novel compounds of formula I-A set out in table 1 (see above):

The pyrazole derivatives provided by the present invention are useful in therapeutic treatment of the human or animal body, specifically the compounds are inhibitors of the human immunodeficiency virus reverse transcriptase enzyme. Accordingly, the present pyrazole derivatives are therapeutically active substances in the treatment of diseases mediated by the human immunodeficiency virus (HIV) and can be used as medicaments for the treatment of such diseases.

They can be used as medicaments, especially for treating viral diseases, immune mediated conditions or diseases, bacterial diseases, parasitic diseases, inflammatory diseases, hyperproliferative vascular diseases, tumors and cancer.

In particular, compounds of the present invention and pharmaceutical compositions containing the same are useful as chemotherapeutic agents, inhibitors of viral replication and modulators of the immune system, and can be used for the treatment of diseases mediated by the human immunodeficiency virus (HIV) other viral diseases such as retroviral infections (either alone or in combination with other antiviral agents such as interferon or derivatives thereof, such as conjugates with polyethylene glycol).

They can be used alone, or in combination with other therapeutically active agents, for example, an immunosuppressant, a chemotherapeutic agent, an anti-viral agent, an antibiotic, an anti-parasitic agent, an anti-inflammatory agent, an anti-fungal agent and/or an anti-vascular hyperproliferation agent.

Compounds, whenever prepared by the processes of the present invention are also an object of the present invention.

The compounds of the present invention can be prepared as shown in the following reaction schemes. The reactions can be carried out in a conventional manner known to those skilled in the art. The starting compounds required for the manufacture of the compounds of formula I are commercially available or can be prepared readily according to methods known in the art.

In the present specification "comprise" means "includes" and "comprising" means "including".

Reaction scheme 1:

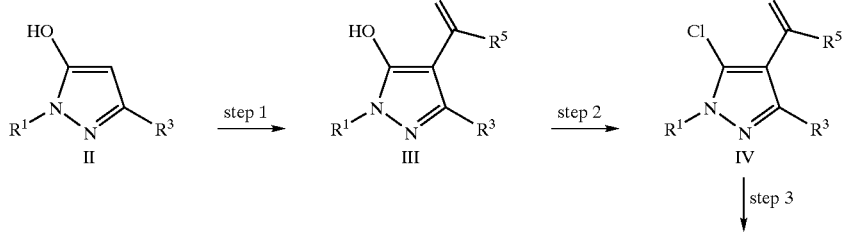

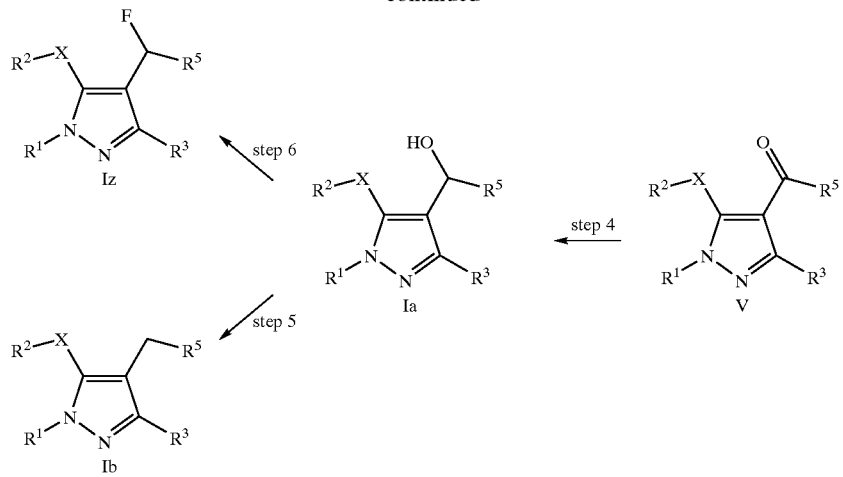

wherein $R^1$, $R^2$, $R^3$ and X are as defined for compounds of formula I and $R^5$ is aryl or heterocyclyl.

In reaction scheme 1, the first reaction step is carried out in that 5-hydroxy pyrazole derivatives of formula II (commercially available or synthesized in a conventional manner known to the skilled in the art as described in e.g. WO 9842678 or J. DeRuiter et al., J. Heterocyclic Chem., 1987, 24, 149) are reacted with $R^5$COCl (commercially available or synthesized according to methods known from textbooks about organic chemistry e.g. from J. March (1992), "Advanced Organic Chemistry: Reactions, Mechanisms, and Structure", 4th ed. John Wiley & Sons) wherein $R^5$ is as defined above in an appropriate solvent to obtain a 4-substituted oxo 5-hydroxy pyrazole derivative of formula III. The reaction is conveniently carried out under conditions known from acylation reactions for example in an inert solvent, such as ethers e.g. anhydrous tetrahydrofuran, diethyl ether, dibutyl ether, dioxane, preferably dioxane, or a mixture of the mentioned solvents, at a reaction temperature from room temperature to boiling temperature of the reaction mixture in the presence of a catalyst such as $Ca(OH)_2$, $K_2CO_3$, $AlCl_3$, $BF_3$, $FeCl_3$, $SnCl_4$ or $ZnCl_2$, preferably $Ca(OH)_2$.

In the second step of the reaction, the 5-hydroxy position of compounds of formula III is chlorinated with a chlorinating agent such as $(COCl)_2$, HCl, $PCl_5$, $PCl_3$, $SOCl_2$ or $POCl_3$ to obtain 5-chloro-pyrazole derivatives of formula IV. The reaction is conveniently carried out under an inert atmosphere such as nitrogen or argon atmosphere at a reaction temperature from room temperature to boiling temperature of the reaction mixture. Preferably, the reaction is carried out in the presence of $POCl_3$ at a reaction temperature between about 50° C. and about 180° C. Optionally, the reaction can be carried out in an organic solvent such as halogenated hydrocarbons (e.g. dichloromethane or trichloromethane), hydrocarbons (e.g. cyclohexane, methyl cyclohexane, decaline, benzene, toluene, o-xylene, m-xylene or p-xylene) or a mixtures of the mentioned solvents.

In the third step of the reaction, compound of formula IV is reacted with $R^2$SH or with $R^2$OH (both agents are commercially available or can be synthesized according to methods known from textbooks about organic chemistry e.g. from J. March (1992), "Advanced Organic Chemistry: Reactions, Mechanisms, and Structure", $4^{th}$ ed. John Wiley & Sons) wherein $R^2$ is as defined for compounds of formula I to obtain the pyrazole derivative of formula V. The reaction is carried out in an appropriate solvent in the presence of a base such as such as n-BuLi, sodium hydride, trialkylamine such as trimethylamine or triethylamine, potassium carbonate, sodium carbonate, magnesium carbonate, calcium carbonate, preferably potassium carbonate. The reaction is conveniently carried out under an inert atmosphere such as nitrogen or argon atmosphere at a reaction temperature from 0° C. to boiling temperature of the reaction mixture, preferably at a reaction temperature between about 10° C. and about 180° C. Appropriate solvents for the reaction are THF or polar aprotic solvents such as dimethylsulfoxide (DMSO), dimethylacetamide or N,N-dimethylformamide (DMF), preferably DMF.

In the fourth step of the reaction, the oxo group of compound of formula V is reduced to obtain the corresponding hydroxy compound of formula Ia. The reaction is conveniently carried out with a base such as sodium borohydride, lithium borohydride or preferably sodium borohydride in an organic solvent for example alcoholic solvents such as methanol, ethanol, propanol, butanol, octanol or cyclohexanol, preferably methanol or ethers (e.g. tetrahydrofuran, diethyl ether, dibutyl ether, dioxane or diglyme) at a reaction temperature from 0° C. to boiling temperature of the reaction mixture, preferably at a reaction temperature between about 5° C. and about 80° C. The reduction reaction is carried out as it is described in textbooks about organic chemistry e.g. from J. March (1992), "Advanced Organic Chemistry: Reactions, Mechanisms, and Structure", $4^{th}$ ed. John Wiley & Sons).

In the fifth step of the reaction, the methyl hydroxy group of compound of formula Ia is further reduced to the corresponding methylene group to obtain the compound of formula Ib. The reaction is conveniently carried out in the presence of trialkylsilane such as trimethylsilane, triethylsilane or tripropylsilane, preferably triethylsilane dissolved in mineral acids such as trifluoroacetic acid (TFA) or in Lewis acids such as $SnCl_4$ (described in D. L. Comins et al., Tet. Lett., 1986, 27, 1869) at a reaction temperature from 0° C. to 80° C., preferably at a reaction temperature between about 5° C. and about 50° C.

The reduction reaction can also be carried out in the presence of NaI, $(CH_3)_3SiCl$ and HBr or as described in textbooks about organic chemistry e.g. from J. March (1992), "Advanced Organic Chemistry: Reactions, Mechanisms, and Structure", $4^{th}$ ed. John Wiley & Sons).

When the hydroxy group is converted into a leaving group such as a mesylate or sulphonate, preferably a mesylate, the reaction can then be carried out in the presence of Zn and acetic acid (described in J. E. Lynch et al., J. Org. Chem., 1997, 62, 9223–9228).

Optionally, the oxo derivative of compound of formula V is directly reduced to the corresponding methylene compound of formula Ib. Such methods for the direct reduction are for example the Clemmensen reduction, the Wolff-Kishner reduction, hydogenolysis of thioacetals or reduction using trialkylsilane such as trimethylsilane, triethylsilane or tripropylsilane, preferably triethylsilane dissolved in mineral acids such as trifluoroacetic acid (TFA).

In the sixth step of the reaction, the methyl hydroxy group of compound of formula Ia is converted into the corresponding fluoromethylene group to obtain the compound of formula Iz. The reaction is carried out by treatment of the compound of formula Ia with a suitable fluorinating agent such as a dialkylaminosuphur trifluoride $(R^7)_2NSF_3$ of formula XIV, wherein $R^7$ can be $C_{1-4}$-alkyl (e.g. ethyl) or $(R^7)_2N$ can be a cyclic amino group (e.g. morpholine). The fluorinating agent is commercially available (e.g. diethylamino sulfur trifluoride (DAST)) or can be synthesized according to known methods in the art. The fluorinating reaction can be carried out as described in textbooks about organic chemistry e.g. from J. March (1992), "Advanced Organic Chemistry: Reactions, Mechanisms, and Structure", 4th ed. John Wiley & Sons).

Reaction scheme 2:

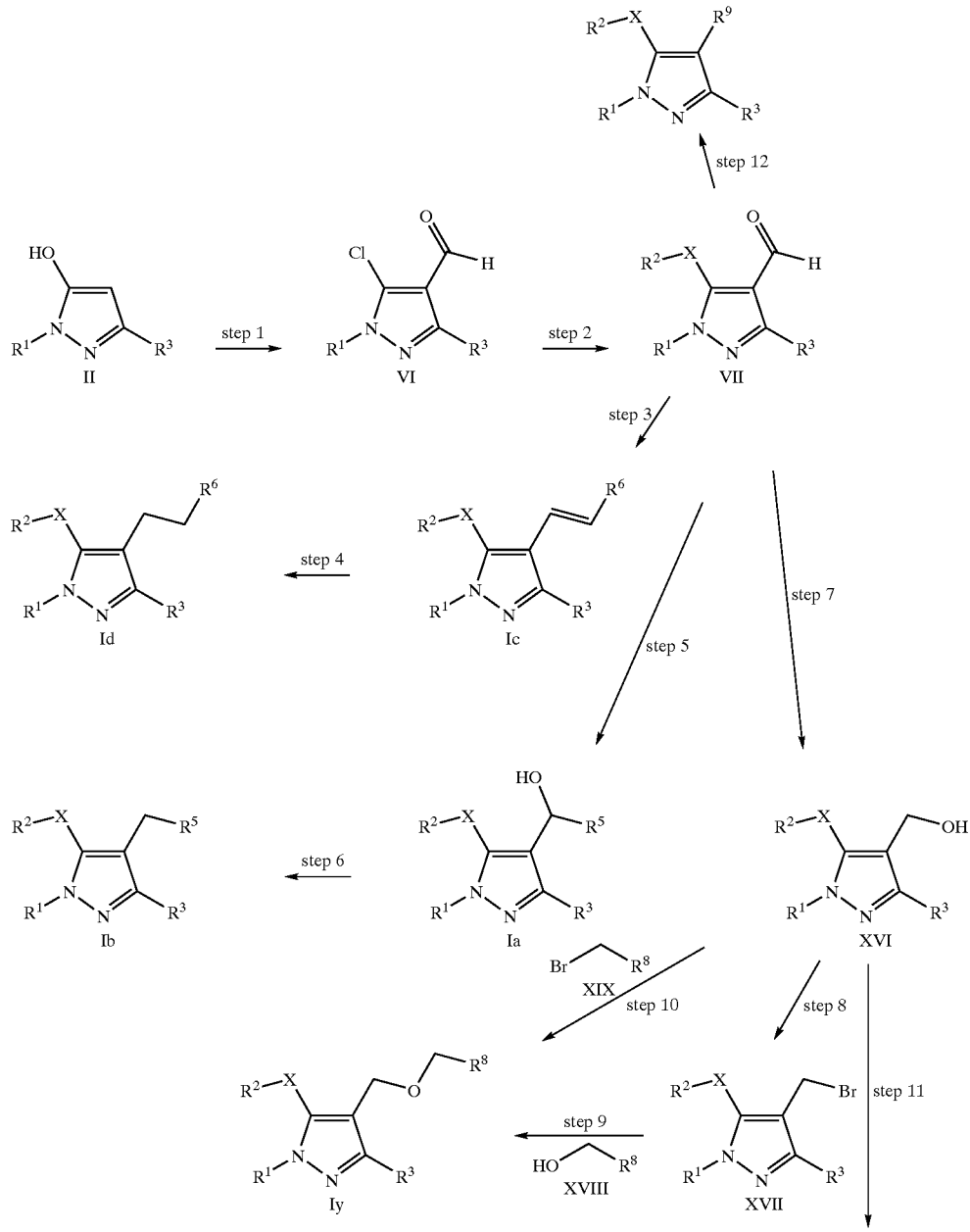

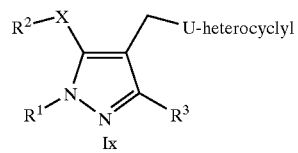

wherein $R^1$, $R^2$, $R^3$, U and X are as defined for compounds of formula I, $R^5$, $R^6$ and $R^8$ are aryl or heterocyclyl and $R^9$ is $CH_2$-(aryl-$C_{1-4}$-alkylamino).

In reaction scheme 2, the first reaction step is carried out in that 5-hydroxy pyrazole derivatives of formula II (commercially available or synthesized in a conventional manner known to the skilled in the art as described in e.g. WO 9842678 or J. DeRuiter et al., J. Heterocyclic Chem., 1987, 24, 149) are converted to 4-carbaldehyde 5-chloro pyrazole derivatives of formula VI. The reaction which includes a hydroxy/chlorine exchange in the 5-position and the introduction of a C(=O)H group in the 4-position of the pyrazole is conveniently carried out with disubstituted formamide such as N,N-dimethylformamide, N,N-methylphenylformamide or N,N-diphenylformamide in the presence of $POCl_3$ according the Vilsmeier reaction. The reaction is carried out under an inert atmosphere such as nitrogen or argon atmosphere at a reaction temperature from room temperature to boiling temperature of the reaction mixture, preferably at a reaction temperature between about 50° C. and about 150° C. Optionally, the reaction can be carried out in an inert organic solvent such as ethers (e.g. tetrahydrofuran, diethyl ether, dibutyl ether or dioxane), polar aprotic solvents such as dimethylsulfoxide (DMSO) or dimethylacetamide N, halogenated hydrocarbons (e.g. dichloromethane or trichloromethane), hydrocarbons (e.g. cydohexane, methyl cyclohexane, decaline, benzene, toluene, o-xylene, m-xylene or p-xylene) or a mixtures of the mentioned solvents. The chlorinating reaction can also be carried out according the method described for reaction scheme 1 (step 2) with chlorinating agent such as $(COCl)_2$, HCl, $PCl_5$, $PCl_3$ or $SOCl_2$. The introduction of the C(=O)H group (formylation reaction) to the pyrazole derivative can also be carried out according to methods known from organic textbooks (J. March (1992), "Advanced Organic Chemistry: Reactions, Mechanisms, and Structure", $4^{th}$ ed. John Wiley & Sons). Such methods are for example Friedel-Crafts reaction, Vilsmeier-Haack reaction, Gattermann reaction, Gattermann-Koch reaction, Hoeben-Hoesch reaction or Reimer-Tiemann reaction.

In the second step of the reaction, compound of formula VI is reacted with $R^2SH$ or with $R^2OH$ (both agents are commercially available or can be synthesized according to methods known from textbooks about organic chemistry e.g. from J. March (1992), "Advanced Organic Chemistry: Reactions, Mechanisms, and Structure", $4^{th}$ ed. John Wiley & Sons) wherein $R^2$ is as defined for compounds of formula I to obtain the pyrazole derivative of formula VII. The reaction is carried out according the method described for reaction scheme 1 (step 3).

In the third step of the reaction, the aldehyde function of compound of formula VII is reacted via a Wittig-Horner reaction with dialkyl phosphonate of formula $(EtO)_2P(=O)(CH_2)_nR^6$ wherein n is a number 1, 2 or 3 to olefinic compound of formula Ic. The reaction is carried out similar the method described in the literature, for example in the presence of a strong base such as n-BuLi or preferably sodium hydride in an organic solvent for example anhydrous ethers such as diethyl ether, dibutyl ether, dioxane, preferably anhydrous tetrahydrofuran under inert atmosphere such as nitrogen or argon atmosphere at a reaction temperature from 0° C. to 80° C., preferably at a reaction temperature between about 5° C. and about 50° C. Optionally, olefinic compound of formula Ic can be obtained through other coupling reactions for example the Wittig reaction.

In the fourth step of the reaction, the olefinic group of compound of formula Ic is hydrogenated to the corresponding compound of formula Id. The reaction is carried out similar to methods described in the literature, for example under hydrogen in the presence of a hydrogenation catalyst in an appropriate solvent at a reaction temperature from 0° C. to 80° C., preferably at a reaction temperature between about 5° C. and about 50° C. The hydrogen pressure can be between about 0 atm and about 100 atm, preferably between about 0 atm and about 50 atm and most preferred between about 0 atm and about 20 atm. The hydrogenation catalyst used for this reaction can be one of the commonly known catalysts such as noble metals (e.g. Pt, Pd or Rh) on supporting materials such as activated carbon or $Al_2O_3$, or generally as described in textbooks about organic chemistry e.g. J. March (1992), "Advanced Organic Chemistry: Reactions, Mechanisms, and Structure", $4^{th}$ ed. John Wiley & Sons). Preferred hydrogenation catalysts are Pd on activated carbon or Raney-Nickel. Appropriate solvents for the hydrogenation reaction are organic solvent such as alcohols (e.g. methanol, ethanol, propanol, butanol, octanol or cyclohexanol), ethers (e.g. tetrahydrofuran, diethyl ether, dibutyl ether or dioxane), ketones (e.g. acetone, butanone or cyclohexanone), polar aprotic solvents such as dimethylsulfoxide (DMSO) or dimethylacetamide N, esters (e.g. ethyl acetate), halogenated hydrocarbons (e.g. dichloromethane or trichloromethane), hydrocarbons (e.g. cyclohexane, methyl cyclohexane, decaline, benzene, toluene, o-xylene, m-xylene or p-xylene) or a mixtures of the mentioned solvents. Preferred solvents are ester, most preferred solvent is ethyl acetate.

In the fifth step of the reaction, the pyrazole of formula VII is derivatised with a Grignard reagent $R^5MgHal$ of formula XV, wherein $R^5$ is aryl or heterocyclyl as defined for compounds of formula I and Hal represents chlorine, bromine or iodine, preferably chlorine (commercially available or synthesised according to textbooks on organic chemistry e.g. from J. March (1992), "Advanced Organic Chemistry: Reactions, Mechanisms and Structure", $4^{th}$ ed. John Wiley and Sons) to obtain the corresponding substituted hydroxymethyl-pyrazole derivative of formula Ia. The derivatisation reaction is conveniently carried out in an inert solvent for example ethers such as tetrahydrofuran, diethyl ether, dibutyl ether, dioxane, diglyme or a mixture of the mentioned solvents, preferably tetrahydrofuran at a reaction temperature between about −10° C. and about 60° C., preferably at a reaction temperature between about 0° C. and about 40° C., more preferred at room temperature. In general, the derivatisation reaction can also be carried out as described in textbooks about organic chemistry e.g. from J. March (1992), "Advanced Organic Chemistry: Reactions, Mechanisms, and Structure", $4^{th}$ ed. John Wiley & Sons. Instead of a Grignard reagent $R^5MgHal$ of formula XV the corresponding lithium reagent of formula $LiR^5$ can be used as well.

In the sixth step of the reaction, the reduction reaction is carried out as described in reaction scheme 1 (step 5) or can also be carried in the presence $P_2I_4$ as described in EP 0627423.

For the synthesis of compounds of formula I wherein $R^1$, $R^2$, $R^3$ and X are as defined in claim 1 and A is $CH_2$-(aryl-$C_{1-4}$-alkoxy) or $CH_2$-(heterocyclyl-$C_{1-4}$-alkoxy), compounds of formula VII are converted via a reduction and subsequent etherification reaction to the corresponding compounds of formula I wherein $R^1$, $R^2$, $R^3$ and X are as defined in claim 1 and A is $CH_2$-(aryl-$C_{1-4}$-alkoxy) or $CH_2$-(heterocyclyl-$C_{1-4}$-alkoxy). Both reactions are known from textbooks about organic chemistry e.g. from J. March (1992), "Advanced Organic Chemistry: Reactions, Mechanisms, and Structure", $4^{th}$ ed. John Wiley & Sons. For example compounds of formula VII are first reduced with an appropriate reducing agent (e.g. $NaBH_4$ in an alcoholic solvent such as methanol) to the corresponding alcohol derivative and secondly reacted with an aryl-$C_{1-4}$ alkyl-halide or heterocyclyl-$C_{1-4}$ alkyl-halide under basic conditions (e.g. NaH in a polar aprotic solvent such as DMF) to the corresponding compounds of formula I wherein $R^1$, $R^2$, $R^3$ and X are as defined in claim 1 and A is $CH_2$-(aryl-$C_{1-4}$-alkoxy) or $CH_2$-(heterocyclyl-$C_{1-4}$-alkoxy).

The above reaction is described in more detail in steps 7–9.

In the seventh step of the reaction, the aldehyde of formula VII is reduced in the presence of a reducing agent to obtain the corresponding hydroxy-methyl derivative of formula XVI. Reducing agents conveniently used for the reaction are preferably sodium borohydride or other reducing agents such as lithium borohydride, sodium triacetoxyborohydride, hydrogen over a catalyst or reducing agents known in the art applied according to known methods described in textbooks on organic chemistry e.g. from J. March (1992), "Advanced Organic Chemistry: Reactions, Mechanisms and Structure", $4^{th}$ ed. John Wiley and Sons. The reduction reaction is conveniently carried out in an organic solvent for example alcoholic solvents such as methanol, ethanol, propanol, butanol, octanol or cyclohexanol, preferably methanol or ethanol or ethers such as tetrahydrofuran, diethyl ether, dibutyl ether, dioxane or diglyme, preferably tetrahydrofuran or a mixture of the mentioned solvents such as methanol and tetrahydrofuran or ethanol and tetrahydrofuran. The reaction is carried out at a reaction temperature between about $-10°$ C. and about $60°$ C., preferably at room temperature. The reduction reaction can also be carried out as described in textbooks about organic chemistry e.g. from J. March (1992), "Advanced Organic Chemistry: Reactions, Mechanisms, and Structure", $4^{th}$ ed. John Wiley & Sons.

In the eighth step of the reaction, the hydroxy-methyl function of compound of formula XVI is converted to the corresponding bromo-methyl derivative of formula XVII according to standard procedures according to methods known from textbooks on organic chemistry e.g. from J. March (1992), "Advanced Organic Chemistry: Reactions, Mechanisms, and Structure", $4^{th}$ ed. John Wiley & Sons. A possible method for the preparation of a bromide derivative of formula XVII is by using tetrabromomethane in the presence of triphenylphosphine in dichloromethane, at room temperature.

In the ninth step of the reaction, the bromide of formula XVII is reacted with an arylmethanol or a heterocyclyl-methanol compound $HOCH_2R^8$ of formula XVIII to obtain the corresponding pyrazole derivative of formula Iy. The reaction is conveniently carried out according to methods known from textbooks on organic chemistry e.g. from J. March (1992), "Advanced Organic Chemistry: Reactions, Mechanisms and Structure", $4^{th}$ ed. John Wiley and Sons). The reaction is for example carried out in the presence of a base such as sodium hydride, lithium hydride, potassium carbonate or triethylamine in an appropriate organic solvent such as tetrahydrofuran (THF) or polar aprotic solvents like dimethylsulfoxide (DMSO), N,N-dimethylacetamide or N,N-dimethylformamide (DMF), preferably DMF or THF, at a reaction temperature between about $-10°$ C. and about $60°$ C., preferably at room temperature.

In the tenth step of the reaction, the bromide, the hydroxymethyl pyrazole derivative $BrCH_2R^8$ of formula XVI is directly converted to the corresponding pyrazole derivative of formula Iy. The reaction is carried out according to standard procedures according to methods known from textbooks on organic chemistry e.g. from J. March (1992), "Advanced Organic Chemistry: Reactions, Mechanisms, and Structure", $4^{th}$ ed. John Wiley & Sons. A possible method for the preparation of the pyrazole derivative of formula Iy is the reaction of the hydroxy-methyl pyrazole derivative of formula XVI with an arylmethylbromide or a heterocyclyl-methylbromide compound of formula XIX in the presence of a base. The reaction may be preferably carried out in an organic solvent such as polar aprotic solvents like N,N-dimethylacetamide or N,N-dimethylformamide (DMF), dichloromethane or tetrahydrofuran using a base such as sodium hydride, lithium hydride, potassium hydride, lithium carbonate, sodium carbonate, potassium carbonate or organic amines such as triethylamine, morpholine or an N-alkyl morpholine such as N-methylmorpholine at a reaction temperature between about $-10°$ C. and about $60°$ C., preferably at room temperature.

In the eleventh step of the reaction, the hydroxy-methyl pyrazole derivative of formula XVI is converted via a Mitsunobu reaction to the corresponding compounds of formula Ix. The reaction is known to those skilled in the art (D. L. Hughes, Organic Preparations and Procedures International, 1996, 28, 127; 0. Mitsunobu, Synthesis 1981, 1). The reaction is carried out in the presence of a trialkyl- or triarylphosphine, such as triphenylphosphine, and a reagent of formula RC(O)N=NC(O)R [R=alkoxy or dialkylamino], such as diethyl azodicarboxylate. The reaction is carried out in an appropriate organic solvent such as dichloromethane, tetrahydrofuran (THF) or polar aprotic solvents like N,N-dimethylacetamide or N,N-dimethylformamide (DMF), preferably DMF or THF, at a reaction temperature between about $-10°$ C. and about $60°$ C., preferably at room temperature.

Compounds of formula Ix, wherein U is S are synthesized starting with bromomethyl intermediate XVII, using an alkylation reaction with a mercapto heterocycle (thio heterocycle of formula Het-SH). This reaction is carried out according to standard procedures according to methods known from textbooks on organic chemistry e.g. from J. March (1992), "Advanced Organic Chemistry: Reactions, Mechanisms, and Structure", $4^{th}$ ed. John Wiley & Sons. The reaction is preferably carried out in an organic solvent such as polar aprotic solvents like N,N-dimethylacetamide or N,N-dimethylformamide (DMF), dichloromethane or tetrahydrofuran using a base such as sodium hydride, lithium hydride, potassium hydride, lithium carbonate, sodium carbonate, potassium carbonate or organic amines such as triethylamine, morpholine or an N-alkyl morpholine such as N-methylmorpholine at a reaction temperature between about −10° C. and about 60° C., preferably at room temperature In the twelfth step of the reaction, compound of formula VII is converted via a reductive amination reaction to the corresponding compounds of formula Iw wherein $R^1$, $R^2$, $R^3$ and X are as defined in claim 1 and $R^9$ is $CH_2$-(aryl-$C_{1-4}$-alkylamino). The reductive amination reaction is known from textbooks about organic chemistry e.g. from J. March (1992), "Advanced Organic Chemistry: Reactions, Mechanisms, and Structure", $4^{th}$ ed. John Wiley & Sons). For example compound of formula VII is reacted with an aryl amine derivative to the corresponding imine derivative and subsequently reduction reaction with for example NaBH (OAc)$_3$ to yield the compounds of formula Iw wherein $R^1$, $R^2$, $R^3$ and X are as defined in claim 1 and $R^9$ is $CH_2$-(aryl-$C_{1-4}$-alkylamino). Optionally, the secondary amine can be alkylated with a $C_{1-4}$-alkyl halide to the corresponding $C_{1-4}$-alkylated compounds of formula Iw. The alkylation reaction is known from textbooks about organic chemistry e.g. from J. March (1992), "Advanced Organic Chemistry: Reactions, Mechanisms, and Structure", $4^{th}$ ed. John Wiley & Sons).

halogenated hydrocarbons (e.g. dichloromethane or trichloromethane) or hydrocarbons (e.g. cyclohexane, methyl cyclohexane, decaline, benzene, toluene, o-xylene, m-xylene or p-xylene), preferably toluene. The reaction is carried out at a reaction temperature from room temperature to boiling temperature of the reaction mixture, preferably at a reaction temperature between about 50° C. and about 150° C.

In the second step of the reaction, compound of formula IX is reacted with $R^5COCl$ (commercially available or synthesized according to methods known from textbooks about organic chemistry e.g. from J. March (1992), "Advanced Organic Chemistry: Reactions, Mechanisms, and Structure", $4^{th}$ ed. John Wiley & Sons) wherein $R^5$ is as defined above in an appropriate solvent to obtain a 4-substituted oxo pyrazole derivative of formula X. The reaction is carried out under the same conditions described for reaction scheme 1 (step 1).

In the third step of the reaction the 5-hydroxy position of compounds of formula X is chlorinated with a chlorinating agent such as $(COCl)_2$, HCl, $PCl_5$, $PCl_3$, $SOCl_2$ or $POCl_3$ to obtain 5-chloro-pyrazole derivatives of formula XI. Conveniently the reaction can be carried out with $POCl_3$ at a reaction temperature between about 0° C. and about boiling Reaction scheme 3:

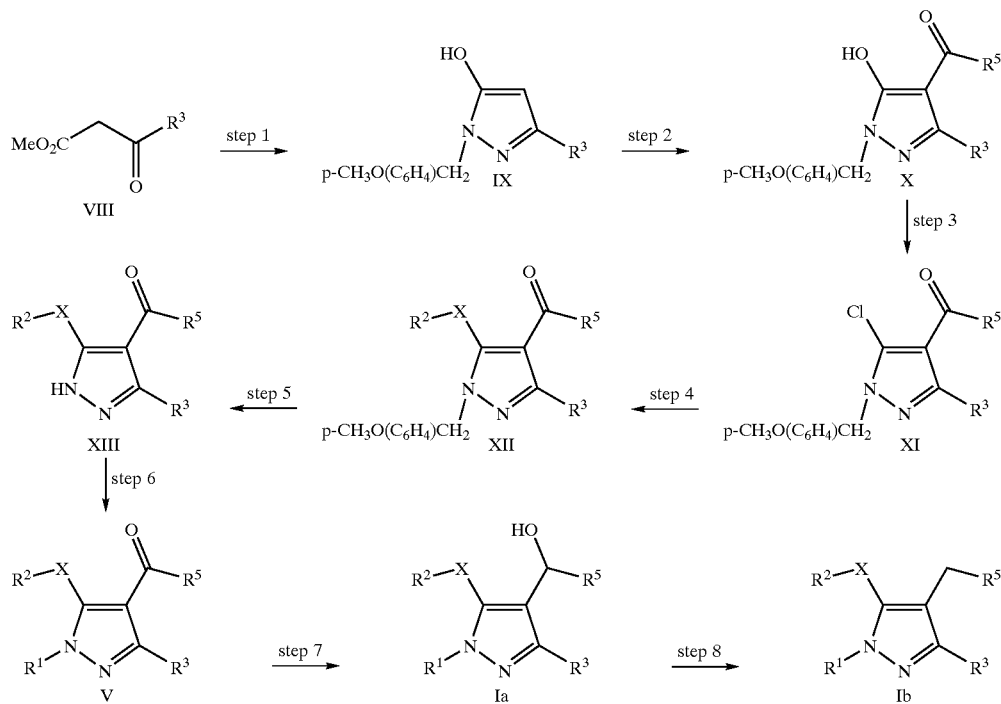

wherein $R^1$, $R^2$, $R^3$ and X are as defined for compounds of formula I and $R^5$ is aryl or heterocyclyl.

In reaction scheme 3, the first reaction step is carried out in that p-$CH_3O(C_6H_4)CH_2NHNH_2.2HCl$ (preparation see example 3) is reacted with compounds of formula VIII to obtain pyrazole derivatives of formula IX. The reaction is conveniently carried out in the presence of a base for example potassium carbonate, sodium carbonate, magnesium carbonate, calcium carbonate, potassium hydroxide, sodium hydroxide, magnesium hydroxide, calcium hydroxide, $N(CH_3)_3$, $N(C_2H_5)_3$, $N(n-C_3H_7)_3$, $N(i-C_3H_7)_3$, preferably a trialkyl amine, in an appropriate solvent such as temperature of the reaction mixture, preferably between about 5° C. and about 100° C. The reaction can optionally be carried out under an inert atmosphere such as nitrogen or argon atmosphere and in an organic solvent such as ethers (e.g. tetrahydrofuran, diethyl ether, dibutyl ether or dioxane), halogenated hydrocarbons (e.g. dichloromethane or trichloromethane), hydrocarbons (e.g. cyclohexane, methyl cyclohexane, decaline, benzene, toluene, o-xylene, m-xylene or p-xylene) or a mixtures of the mentioned solvents.

In the fourth step of the reaction, compound of formula XI is reacted with $R^2SH$ or with $R^2OH$ (both agents are commercially available or can be synthesized according to methods known from textbooks about organic chemistry e.g. from J. March (1992), "Advanced Organic Chemistry: Reactions, Mechanisms, and Structure", 4$^{th}$ ed. John Wiley & Sons) wherein $R^2$ is as defined for compounds of formula I to obtain the pyrazole derivative of formula XII. The reaction is carried out in an appropriate solvent in the presence of a base such as n-BuLi, sodium hydride, trialkylamine such as trimethylamine or triethylamine, potassium carbonate, sodium carbonate, magnesium carbonate, calcium carbonate, preferably potassium carbonate. The reaction is carried out in an appropriate solvent in the presence of a base such as sodium hydride, trialkylamine such as trimethylamine or triethylamine, potassium carbonate, sodium carbonate, magnesium carbonate, calcium carbonate, preferably potassium carbonate. The reaction is conveniently carried out at a reaction temperature from 0° C. to boiling temperature of the reaction mixture, preferably at a reaction temperature between room temperature and about 180° C. Appropriate solvents for the reaction are THF or polar aprotic solvents such as dimethylsulfoxide (DMSO), dimethylacetamide or N,N-dimethylformamide (DMF), preferably DMF.

In the fifth step of the reaction, compound of formula XII is reacted with trifluoroacetic acid to remove the 4-methoxybenzyl group of the pyrazole derivative and to yield to unprotected pyrazole compound of formula XIII. The reaction can also be carried out in mineral acids such as HCl in a suitable solvent such as dioxane, ether ethyl acetate or methanol. The reaction is conveniently carried out at a reaction temperature from room temperature to boiling temperature of the reaction mixture, preferably at a reaction temperature between 40° C. and about 150° C. The reaction can optionally be carried out under an inert atmosphere such as nitrogen or argon atmosphere and in an organic solvent such as alcohols (e.g. methanol, ethanol, propanol, butanol, octanol or cyclohexanol), ethers (e.g. tetrahydrofuran, diethyl ether, dibutyl ether or dioxane), ketones (e.g. acetone, butanone or cyclohexanone), esters (e.g. ethyl acetate), halogenated hydrocarbons (e.g. dichloromethane or trichloromethane), hydrocarbons (e.g. cyclohexane, methyl cyclohexane, decaline, benzene, toluene, o-xylene, m-xylene or p-xylene) or a mixtures of the mentioned solvents.

In the sixth step of the reaction, compound of formula XIII is reacted with an alkylating agent of formula $R^1L$ wherein L is a leaving group such as chlorine, bromine, iodine, mesylate or tosylate, to obtain N-substituted pyrazole derivative of formula V. The reaction is conveniently carried out in an appropriate solvent, under an inert atmosphere such as nitrogen or argon atmosphere in the presence of a strong base such as sodium hydride or lithium hydride, preferably sodium hydride. The reaction temperature is preferably from 0° C. to boiling temperature of the reaction mixture, preferably at a reaction temperature between 10° C. and about 150° C.

Appropriate solvents for the reaction are dry polar aprotic solvents such as THF, dimethylsulfoxide (DMSO), dimethylacetamide or N,N-dimethylformamide (DMF), preferably DMF.

In the seventh step of the reaction, the oxo group of compound of formula V is reduced to obtain the corresponding hydroxy compound of formula Ia. The reaction is carried out under the same conditions described for reaction scheme 1 (step 4).

In the eighth step the methyl hydroxy group of compound of formula Ia is further reduced to the corresponding methylene group to obtain the compound of formula Ib. The reaction is carried out under the same conditions described for reaction scheme 1 (step 5).

The synthesis of compounds of formula I wherein $R^1$ is acyl, $C_{1-4}$-alkylsulfonyl or optionally substituted phenylsulfonyl, $R^2$, $R^3$ and X are as defined for compounds of formula I and $R^5$ is aryl or heterocyclyl is preferably carried out in that compounds of formula XIII are acylated or sulphonylated to the corresponding compounds of formula I wherein $R^1$ is acyl, $C_{1-4}$-alkylsulfonyl or optionally substituted phenylsulfonyl. The acylation or sulphonylation reaction are known from textbooks about organic chemistry e.g. from J. March (1992), "Advanced Organic Chemistry: Reactions, Mechanisms, and Structure", 4$^{th}$ ed. John Wiley & Sons). The further reaction steps are carried out in accordance with the reaction as described in reaction scheme 3.

As mentioned above, the compounds of formula I and hydrolyzable esters or ethers thereof or a pharmaceutically acceptable salt thereof are inhibitors of the human immunodeficiency virus reverse transcriptase enzyme both in vitro and in vivo, and can be used in the control or prevention of diseases mediated by the human immunodeficiency virus (HIV).

The activity of the compounds of formula I for the treatment of diseases mediated by the human immunodeficiency virus (HIV) can be demonstrated with the following assay methods.

Assay Method: HIV-1 Reverse Transcriptase Assay: Inhibitor $IC_{50}$ Determination:

HIV-1 RT assay was carried out in 96-well Millipore filtermat NOB50 plates using purified recombinant enzyme and a poly(rA)/oligo(dT)$_{16}$ template-primer in a total volume of 50 $\mu$L. The assay constituents were 50 mM Tris/HCl, 50 mM NaCl, 1 mM EDTA, 6 mM MgCl$_2$, 5 $\mu$M dTTP, 0.1 $\mu$Ci [$^3$H] dTTP, 5 $\mu$g/ml poly (rA) pre annealed to 2.5 $\mu$g/ml oligo (dT)$_{16}$ and a range of inhibitor concentrations in a final concentration of 10% DMSO. Reactions were initiated by adding 5 nM HIV-1 RT and after incubation at 37° C. for 30 min, they were stopped by the addition of 50 $\mu$l ice cold 20%TCA and allowed to precipitate at 4° C. for 30 min. The precipitates were collected by applying vacuum to the plate and sequentially washing with 2×200 $\mu$l of 10% TCA and 2×200 $\mu$l 70% ethanol. Finally the plates were dried and radioactivity counted in a Wallac Microbeta 1450 after the addition of 15 $\mu$l scintillation fluid per well. $IC_{50}$'s were calculated by plotting % inhibition versus log$_{10}$ inhibitor concentrations.

Antiviral Assay Method:

Anti-HIV antiviral activity was assessed using an adaptation of the method of Pauwels et al. {Pauwels et al., 1988, J Virol Methods 20:309–321}. The method is based on the ability of compounds to protect HIV-infected T lymphoblastoid cells (MT4 cells) from cell-death mediated by the infection. The endpoint of the assay was calculated as the concentration of compound at which the cell viability of the culture was preserved by 50% ('50% inhibitory concentration', $IC_{50}$). The cell viability of a culture was determined by the uptake of soluble, yellow 3-[4,5-dimethylthiazol-2-yl]-2,5-diphenyltetrazolium bromide (MTT) and its reduction to a purple insoluble formazan salt. After solubilization, spectrophotometric methods were employed to measure the amount of formazan product.

MT4 cells were prepared to be in logarithmic-phase growth and a total of 2×10$^6$ cells infected with the HXB2-strain of HIV at a multiplicity of 0.0001 infectious units of virus per cell in a total volume of between 200–500 microliters. The cells were incubated with virus for one hour at 37° C. before removal of virus. The cells are then washed in 0.01 M phosphate buffered saline, pH 7.2 before being resuspensed in culture medium for incubation in culture with serial dilutions of test compound. The culture medium used was RPMI 1640 without phenol red, supplemented with penicillin, streptomycin, L-glutamine and 10% fetal calf serum (GM10).

Test compounds were prepared as 2 mM solutions in dimethyl sulphoxide (DMSO). Four replicate, serial 2-fold dilutions in GM10 were then prepared and 50 microliters amounts placed in 96-well plates over a final nanomolar concentration range of 625–1.22. Fifty microliters GM10 and $3.5 \times 10^4$ infected cells were then added to each well. Control cultures containing no cells (blank), uninfected cells (100% viability; 4 replicates) and infected cells without compound (total virus-mediated cell death; 4 replicates) were also prepared. The cultures were then incubated at 37° C. in a humidified atmosphere of 5% $CO_2$ in air for 5 days.

A fresh solution of 5 mg/mL MTT was prepared in 0.01 M phosphate buffered saline, pH 7.2 and 20 microliters added to each culture. The cultures were further incubated as before for 2 hours. They were then mixed by pipetting up and down and 170 microliters of Triton X-100 in acidified isopropanol (10% v/v Triton X-100 in 1:250 mixture of concentrated HCl in isopropanol). When the formazan deposit was fully solubilized by further mixing, the absorbance (OD) of the cultures was measured at 540 nm and 690 nm wavelength (690 nm readings were used as blanks for artefacts between wells). The percent protection for each treated culture was then calculated from the equation:

$$\% \text{ Protection} = \frac{(OD \text{ drug-treated cultures}) - (OD \text{ untreated virus control cultures})}{(OD \text{ uninfected cultures}) - (OD \text{ untreated virus control cultures})} \times 100\%$$

The $IC_{50}$ can be obtained from graph plots of percent protection versus $\log_{10}$ drug concentration.

In both assays, compounds of formulas I range in activity from an $IC_{50}$ of about 0.5 to about 10000 nM or 0.5 to about 5000 nM, with preferred compounds having a range of activity from about 0.5 to about 750 nM, more preferably about 0.5 to 300 nM, and most preferably about 0.5 to 50 nM.

| Structure | RT $IC_{50}$ [nM] | HIV $IC_{50}$ [nM] |
|---|---|---|
| 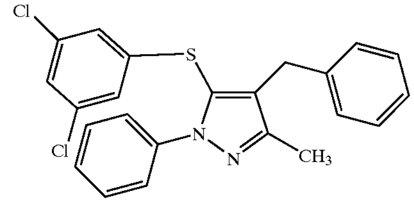 | 2060 | 403 |
| 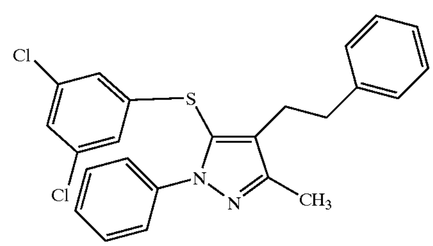 | 3420 | 592 |
| 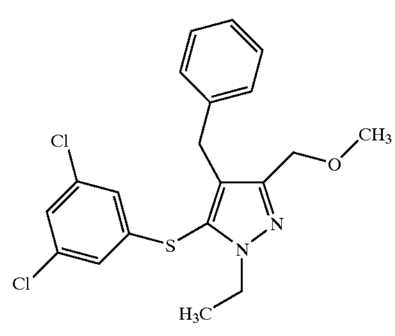 | 8040 | 453 |

-continued

| Structure | RT IC$_{50}$ [nM] | HIV IC$_{50}$ [nM] |
|---|---|---|
| 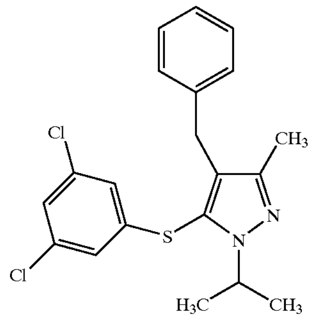 | 270 | 24 |
| 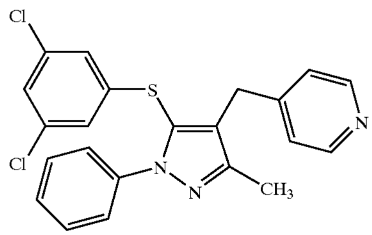 | 105 | 36 |
| 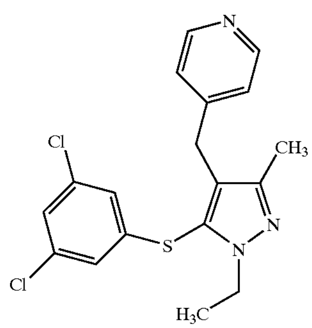 | 84 | 9 |
| 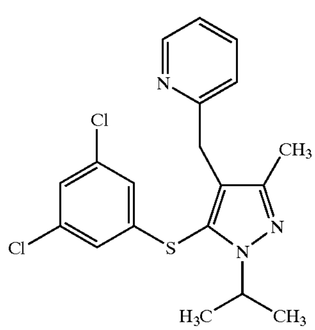 | 1070 | 75 |

-continued

| Structure | RT IC$_{50}$ [nM] | HIV IC$_{50}$ [nM] |
|---|---|---|
| 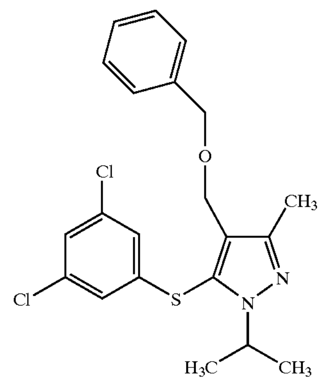 | 349 | 100 |
| 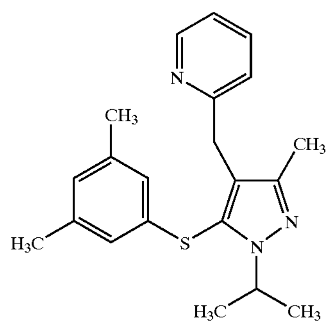 | 950 | 64 |
| 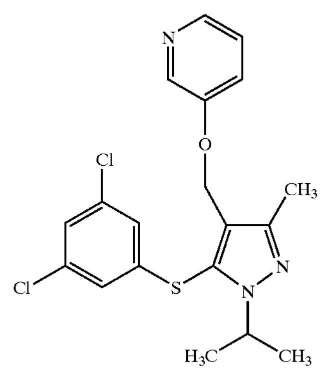 | 313 | 110 |
| 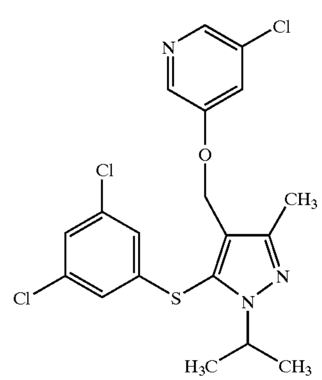 | 650 | 203 |

-continued

| Structure | RT IC$_{50}$ [nM] | HIV IC$_{50}$ [nM] |
|---|---|---|
| 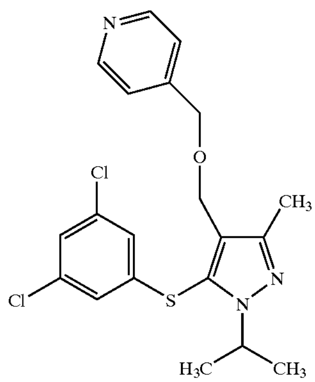 | 112 | 3.6 |
| 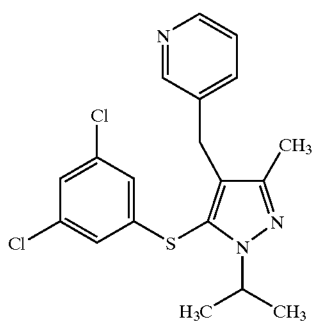 | 572 | 14.6 |
| 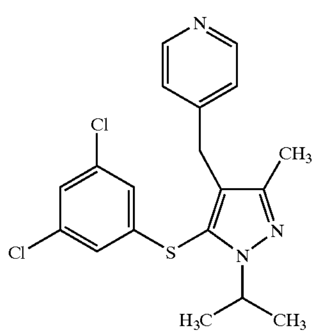 | 76 | 2.7 |
| 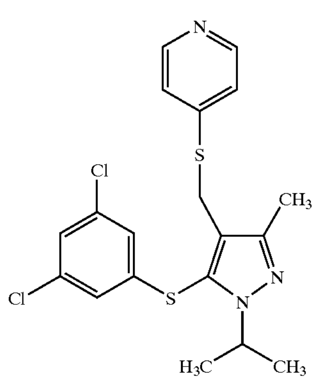 | 292 | 34.1 |

-continued

| Structure | RT IC$_{50}$ [nM] | HIV IC$_{50}$ [nM] |
|---|---|---|
| 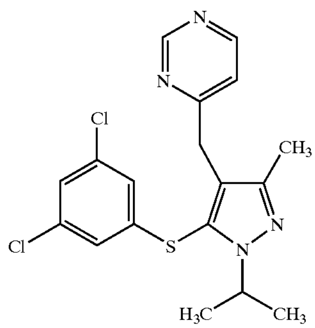 | 456 | 13.5 |
| 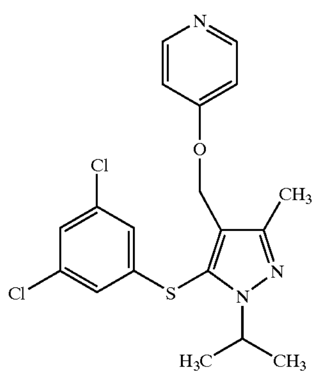 | 252 | 20 |
| 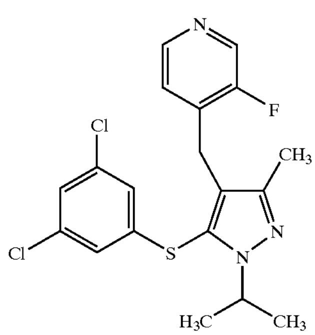 | 373 | 11.1 |
| 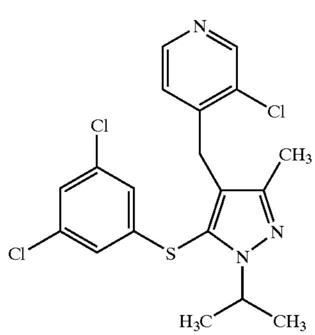 | 177 | 51.7 |

-continued
| Structure | RT IC$_{50}$ [nM] | HIV IC$_{50}$ [nM] |
|---|---|---|
| 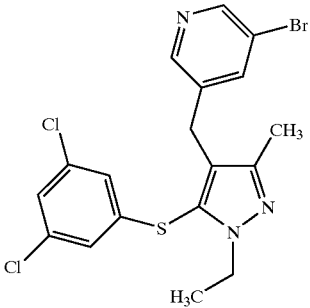 | 398 | 124 |
| 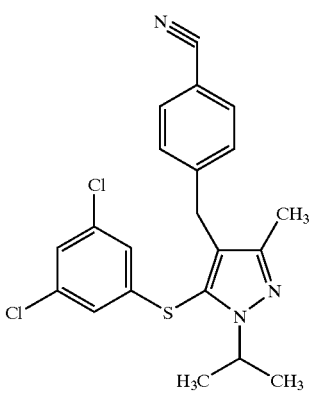 | 176 | 11.9 |
| 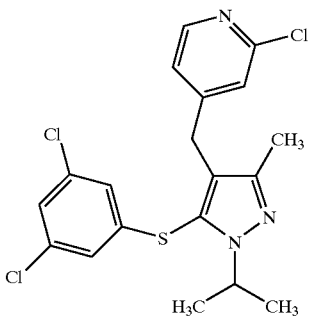 | 109 | 15 |
| 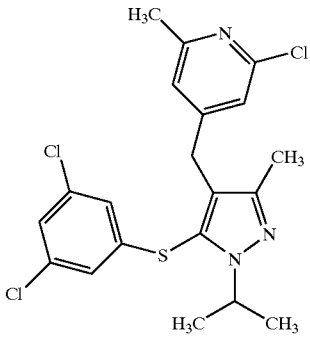 | 880 | 28 |

| Structure | RT IC$_{50}$ [nM] | HIV IC$_{50}$ [nM] |
|---|---|---|
| 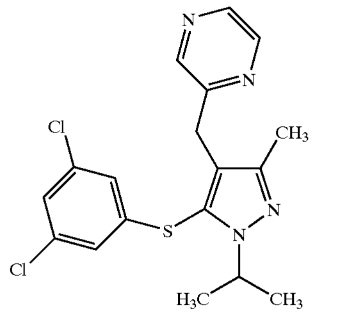 | 270 | 13.9 |
| 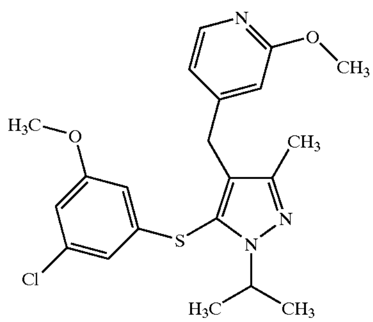 | 298 | 31.5 |
| 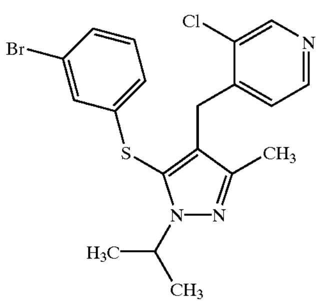 | 5200 | — |
| 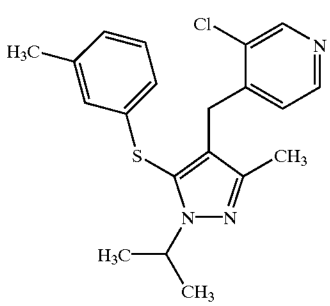 | 1082 | — |
| 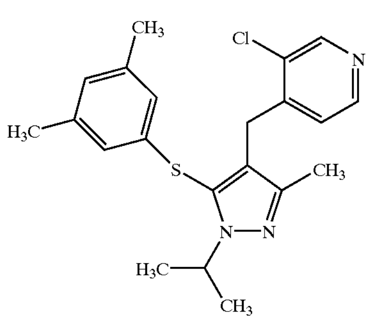 | 607 | — |

| Structure | RT IC$_{50}$ [nM] | HIV IC$_{50}$ [nM] |
|---|---|---|
| 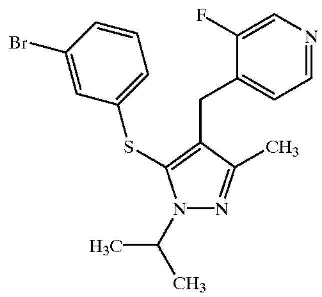 | 463 | 19 |
| 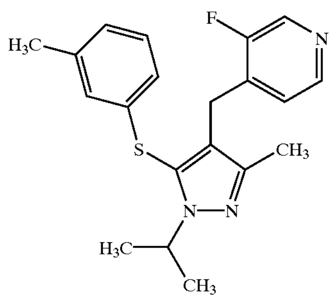 | 480 | 19 |
| 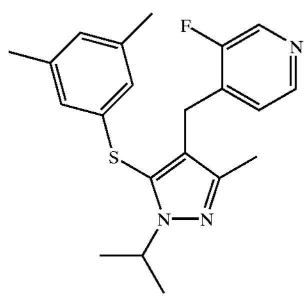 | 90 | 8.1 |

The pyrazole derivatives provided by the present invention are useful in therapeutic treatment of the human or animal body, they are especially useful as inhibitors of the human immunodeficiency virus reverse transcriptase enzyme. Accordingly, the present pyrazole derivatives are therapeutically active substances in the treatment of diseases mediated by the human immunodeficiency virus (HIV) and can be used as medicaments for the treatment of such diseases.

They can be used as medicaments, especially for treating viral diseases, immune mediated conditions or diseases, bacterial diseases, parasitic diseases, inflammatory diseases, hyperproliferative vascular diseases, tumors, and cancer.

In particular, compounds of the present invention and pharmaceutical compositions containing the same are useful as chemotherapeutic agents, inhibitors of viral replication and modulators of the immune system, and can be used for the treatment of diseases mediated by the human immunodeficiency virus (HIV) other viral diseases such as retroviral infections (either alone or in combination with other anti-viral agents such as interferon or derivatives thereof, such as conjugates with polyethylene glycol).

They can be used alone, or in combination with other therapeutically active agents, for example, an immunosuppressant, a chemotherapeutic agent, an anti-viral agent, an antibiotic, an anti-parasitic agent, an anti-inflammatory agent, an anti-fingal agent and/or an anti-vascular hyperproliferation agent.

The products in accordance with the invention can be used as medicaments, e.g. in the form of pharmaceutical preparations which contain them or their salts in admixture with a pharmaceutical, organic or inorganic carrier material which is suitable for parenteral or enteral administration, such as e.g. water, gelatine, gum arabic, lactose, starch, magnesium stearate, talc, vegetable oils, polyalkylene glycols, Vaseline, etc. The pharmaceutical preparations can be present in solid form, e.g. as tablets, dragees, suppositories, capsules, or in liquid form, e.g. as solutions, suspensions or emulsions. They may be sterilized and/or may contain adjuvants such as preservatives, stabilizers, wetting or emulsifying agents, salts for varying the osmotic pressure, anaesthetics or buffers. The compounds of formula I and their salts preferably come into consideration for oral administration and for this purpose are accordingly formulated.

The amount of the compound of formula I required for the treatment of viral diseases, especially diseases mediated by the human immunodeficiency virus (HIV) or other viral diseases will depend on a number of factors including the severity of the disease and the identity, sex and weight of the recipient and will ultimately be at the discretion of the attendant physician. In general, however, a suitable effective dose is in the range of 0.1 to 100 mg per kilogram of body weight of the recipient per day, preferably in the range 0.5 to 50 mg per kilogram of body weight per day and most preferably in the range of 1.0 to 30 mg of body weight per day. An optimum dose is about 5 to 25 mg per kilogram body weight per day. The desired dose is preferably presented as one, two, three, four, five, six or more sub-doses administered at appropriate intervals throughout the day, preferably one, two, three, four or five sub-doses and most preferably one, two or three sub-doses. These sub-doses may be administered in unit dosage forms, for example, containing from 1 to 1500 mg, preferably from 100 to 1400 mg, most preferably from 400 to 1000 mg of active ingredient per unit dosage form.

The dosage of the compounds of general formula I and of the pharmaceutically compatible salts thereof with bases can vary within wide limits and in each individual case will, of course, be fitted to the individual requirements and to the pathogen to be controlled.

As mentioned earlier, medicaments containing a compound of general formula I or a pharmaceutically compatible salt thereof are likewise an object of the present invention, furthermore also a process for the production of such medicaments, which is characterized by bringing one or more compounds of general formula I or pharmaceutically compatible salts thereof and, if desired, one or more other therapeutically valuable substances into a galenical administration form.

It is preferable to administer the compound of formula I as a pharmaceutical formulation. The formulations of the present invention comprise at least one active ingredient of formula I together with one or more pharmaceutically acceptable exipients and optionally one or more other therapeutic agents. Formulations for oral administration may be capsules, cachets or tablets each containing a predetermined amount of active ingredient(s) may be prepared by any method well known in the art of pharmacy. As well as the active ingredients(s) the oral formulation may contain a binder (for example povidone, gelatin, hydroxypropylmethyl cellulose), a lubricant, inert diluent, preservative, disintegrant (for example sodium starch glycollate, cross-linked povidone, cross-linked sodium carboxymethyl cellulose) or a dispersing agent. Formulations for oral use may also include buffering agents to neutralise stomach acidity.

In the following examples the abbreviations used have the following significations:

| | |
|---|---|
| MS | mass spectroscopy |
| ES | electrospray |
| EI | electron impact |
| NMR | nuclear magnetic resonance spectroscopy |
| DMF | N,N-dimethylformamide |
| DMSO | dimethylsulfoxide |
| rt | room temperature |
| min | minute(s) |
| h | hour(s) |

All temperatures are given in degrees Celsius (° C.).

The described NMR spectra were recorded on a Bruker DRX 400 MHz spectrometer with the probe temperature set at 300 K.

The mass spectra indicated by "(M+; EI)", were recorded under electron impact conditions (EI), on a THERMOQUEST MAT95 S with a source temperature of 200° C. Other mass spectra were recorded under electrospray ionization spectra (ESI) conditions, on one of the following machines:

THERMOQUEST SSQ 7000 [Solvent 0.085% TFA in 90% Acetonitrile/water; flow rate 100 microliters/minute; capillary 250° C.; spray voltage 5KV; sheath gas 80 psi], or LC-MS system (liquid chromatograph coupled to mass spectrum) THERMOQUEST TSQ 7000 ELECTROSPRAY or MICROMASS PLATFORM ELECTROSPRAY [Solvent 0.1% TFA in water or 0.085% TFA in 90% acetonitrile/water or 0.085% TFA in acetonitrile].

Compounds, whenever prepared by the processes of the present invention are also an object of the present invention.

The following examples illustrate the present invention:

EXAMPLE 1

4-Benzyl-5-(3,5-Dichlorophenylthio)-3-Methyl-1-Phenyl-1H-Pyrazole

A solution containing 80 mg of [5-(3,5-dichlorophenylthio)-3-methyl-1-phenyl-1H-pyrazol-4-yl]-phenyl-methanol and 64 µl of triethylsilane in 2 ml of trifluoroacetic acid was stirred at rt for 15 h. The mixture was concentrated, diluted with 10 ml of saturated sodium hydrogen carbonate solution and extracted twice with 10 ml of dichloromethane. Combined extracts were dried over magnesium sulphate, filtered and evaporated. The residue was purified by flash chromatography on silica gel using ethyl acetate/petroleum spirit 40°–60° C. (1:10) for the elution to give 60 mg of 4-benzyl-5-(3,5-dichlorophenylthio)-3-methyl-1-phenyl-1H-pyrazole as a colourless gum. Mass spectrum (EI) m/z 424 [M]$^+$. $^1$H NMR (DMSO-d6) 2.26 (s, 3H), 3.88 (s, 2H), 6.77 (d, 2H), 7.13 (m, 3H), 7.20 (m, 2H), 7.32 (t, 1H), 7.35–7.48 (m, 5H).

The starting material [5-(3,5-dichlorophenylthio)-3-methyl-1-phenyl-1H-pyrazol-4-yl]-phenyl-methanol was prepared as follows:

A solution containing 2.0 g of 4-benzoyl-3-methyl-1-phenyl-2-pyrazolin-5-one (commercially available e.g. Aldrich 15,660-4) in 4 ml of phosphorus oxychloride was stirred under nitrogen at 100° C. for 30 min. The mixture was poured into 40 ml of saturated sodium hydrogen carbonate solution and extracted three times with 30 ml of dichloromethane. Combined extracts were dried over magnesium sulphate, filtered and evaporated to give 2.0 g of (5-chloro-3-methyl-1-phenyl-1H-pyrazol-4-yl)-phenyl-methanone as a yellow oil which was used without further purification.

A solution containing 2.0 g of (5-chloro-3-methyl-1-phenyl-1H-pyrazol-4-yl)-phenyl-methanone, 2.0 g of 3,5-dichlorothiophenol and 1.7 g of potassium carbonate in 50 ml of N,N-dimethylformamide was stirred at 60° C. for 19 h. The mixture was partitioned between 100 ml of water and 100 ml of dichloromethane. The organic layer was dried over magnesium sulphate, filtered and evaporated. The residue was purified by flash chromatography on silica gel using methanol/dichloromethane for the elution to give 2.2 g of [5-(3,5-dichloro-phenylsulfanyl)-3-methyl-1-phenyl-1H-pyrazol-4-yl]-phenyl-methanone as a yellow oil. Mass spectrum (ES) m/z 439 [M+H]$^+$, 480 [M+H+CH$_3$CN]$^+$.

A solution of 100 mg of [5-(3,5-dichlorophenylthio)-3-methyl-1-phenyl-1H-pyrazol-4-yl]-phenyl-methanone and 23 mg of sodium borohydride in 5 ml of methanol was stirred at rt for 17 h. The mixture was diluted with 4 ml of water and extracted four times with diethyl ether. Combined extracts were dried over magnesium sulphate, filtered and evaporated. The residue was purified by flash chromatography on silica gel using ethyl acetate/petroleum spirit 40°–60° C. for the elution to give 84 mg of [5-(3,5-dichlorophenylthio)-3-methyl-1-phenyl-1H-pyrazol-4-yl]-phenyl-methanol as a colourless gum. Mass spectrum (EI) m/z 440 [M]$^+$.

EXAMPLES 2–11

The compounds shown in table 2 were prepared in a manner analogous to that scribed in example 1:

TABLE 2

| Ex. | Structure | Name | MS (ES) (M + H)+ |
|---|---|---|---|
| 2 | 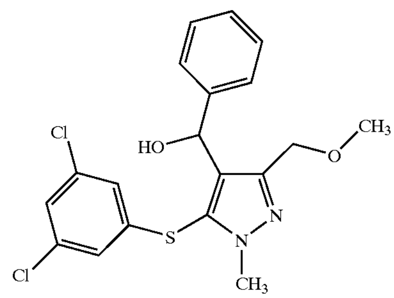 | [5-(3,5-Dichlorophenylthio)-3-(methoxymethyl)-1-methyl-1H-pyrazole-4-yl]-phenyl-methanol | 408 (M+; EI) |
| 3 | 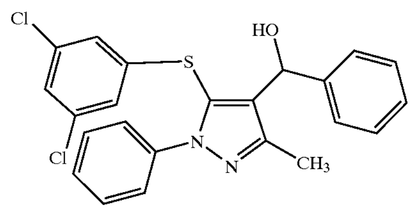 | 5-(3,5-Dichlorophenylthio)-3-methyl-1-phenyl-1H-pyrazole-4-yl]-phenyl-methanol | 440 (M+; EI) |
| 4 | 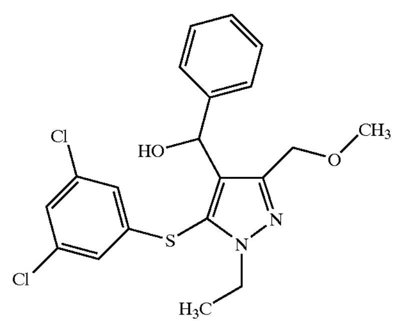 | [5-(3,5-Dichlorophenylthio)-1-ethyl-3-(methoxymethyl)-1H-pyrazole-4-yl]-phenyl-methanol | 422 (M+; EI) |
| 5 | 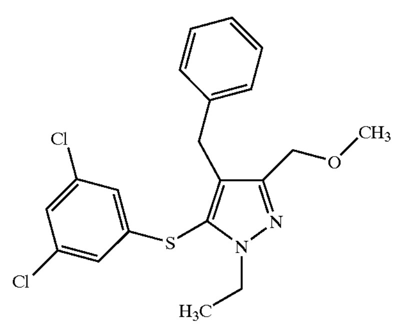 | 4-Benzyl-5-(3,5-dichlorophenylthio)-1-ethyl-3-(methoxymethyl)-1H-pyrazole | 406 (M+; EI) |

TABLE 2-continued

| Ex. | Structure | Name | MS (ES) (M + H)+ |
|---|---|---|---|
| 6 | 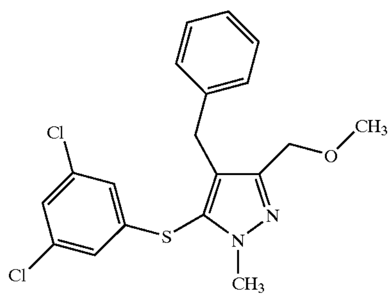 | 4-Benzyl-5-(3,5-dichlorophenylthio)-3-methoxymethyl-1-methyl-1H-pyrazole | 322 (M+; EI) |
| 7 | 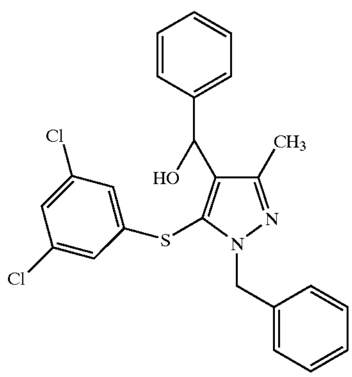 | [5-(3,5-Dichlorophenylthio)-3-methyl-1H-pyrazol-4-yl]-phenyl-methanol | 455 |
| 8 | 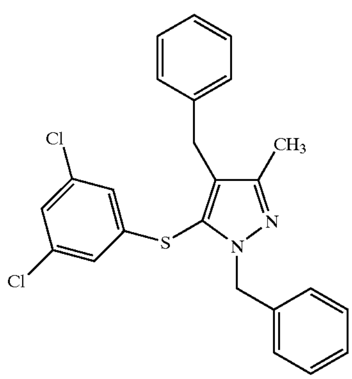 | 1,4-Dibenzyl-5-(3-5-dichlorophenylthio)-3-methyl-1H-pyrazole | 439 |
| 9 | 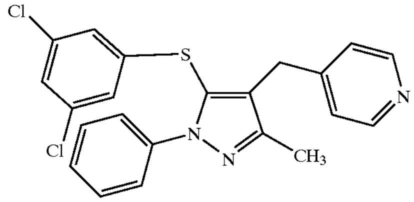 | 4-[5-(3,5-Dichlorophenylthio)-3-methyl-1-phenyl-4-[(4-pyridyl)methyl]-1H-pyrazole | 426 |
| 10 | 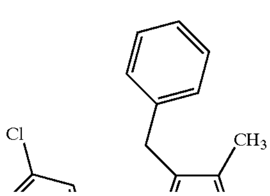 | 4-Benzyl-5-(3,5-dichlorophenylthio)-1-ethyl-3-methyl-1H-pyrazole | 376 (M+; EI) |

EXAMPLE 12

5-(3,5-Dichlorophenylthio)-3-Methyl-4-(2-Phenylethyl)-1-Phenyl-1H-Pyrazole

A suspension containing 95 mg of 5-(3,5-dichlorophenylthio)-3-methyl-1-phenyl-4-styryl-1H-pyrazole and 75 mg of 10% palladium on activated carbon in 10 ml of ethyl acetate was stirred under hydrogen (1 atm) at rt for 40 h. The suspension was filtered on Celite® and the filtrate was evaporated to leave 89 mg of 5-(3,5-dichlorophenylthio)-3-methyl-4-(2-phenylethyl)-1-phenyl-1H-pyrazole as a colourless gum. Mass spectrum (EI) m/z 438[M]$^+$. $^1$H NMR (DMSO-d6) 2.14 (s, 3H), 2.68 (t, 2H), 2.77 (t, 2H), 6.85 (d, 2H), 7.09 (d, 2H), 7.16 (t, 1H), 7.24 (t, 2H), 7.33–7.48 (m, 6H).

The starting material 5-(3,5-dichlorophenylthio)-3-methyl-1-phenyl-4-styryl-1H-pyrazole was prepared as follows:

A solution containing 1.0 g of 5-methyl-2-phenyl-2H-pyrazol-3-ol (commercially available e.g. Aldrich M7,080-0) and 2.1 ml of phosphorus oxychloride in 10 ml of anhydrous N,N-dimethylformamide was stirred under nitrogen at 100° C. for 4 h. The mixture was poured into 70 ml of saturated sodium hydrogen carbonate and extracted three times with 60 ml of dichloromethane. The combined extracts were dried over magnesium sulphate, filtered and evaporated. The residue was purified by chromatography on silica gel using dichloromethane/methanol for the elution to give 177 mg of 5-chloro-3-methyl-1-phenyl-1H-pyrazole-4-carbaldehyde as yellow needles.

A solution containing 175 mg of 5-chloro-3-methyl-1-phenyl-1H-pyrazole-4-carbaldehyde, 142 mg of 3,5-dichlorothiophenol and 132 mg of potassium carbonate in 5 ml of anhydrous N,N-dimethylformamide was stirred under nitrogen at 60° C. for 2 h. The mixture was diluted with 10 ml of water and extracted three times with 8 ml of dichloromethane. The combined extracts were dried over magnesium sulphate, filtered and evaporated. The residue was purified by flash chromatography on silica gel using dichloromethane for the elution to give 164 mg of 5-(3,5-dichlorophenylthio)-3-methyl-1-phenyl-1H-pyrazole-4-carbaldehyde as a yellow oil. Mass spectrum (EI) m/z 362 [M]$^+$.

A solution containing 164 mg of 5-(3,5-dichlorophenylsulphanyl)-3-methyl-1-phenyl-1H-pyrazole-4-carbaldehyde, 103 mg of diethyl benzylphosphonate and 27 mg of sodium hydride (60% in mineral oil) in 5 ml of anhydrous tetrahydrofuran was stirred under nitrogen at rt for 16 h. The solvent was evaporated and the residue was purified by flash chromatography on silica gel using ethyl acetate/petroleum spirit 40°–60° C. (1:10) for the elution to give 162 mg of 5-(3,5-dichlorophenylthio)-3-methyl-1-phenyl-4-styryl-1H-pyrazole as a pale yellow solid. Mass spectrum (EI) m/z 436 [M]$^+$.

EXAMPLES 13–17

The compounds shown in table 3 were prepared in a manner analogous to that described in example 12:

TABLE 3

| Ex. | Structure | Name | MS (ES) (M + H)$^+$ |
|---|---|---|---|
| 13 | 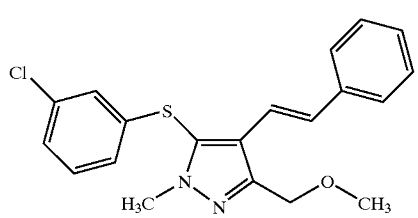 | 5-(3-Chlorophenylthio)-3-methoxymethyl-1-methyl-4-styryl-1H-pyrazole | 371 |
| 14 | 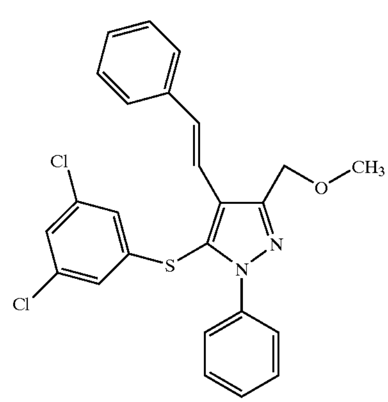 | (E)-5-(3,5-Dichlorophenylthio)-3-(methoxymethyl)-1-phenyl-4-styryl-1H-pyrazole | 467 |

TABLE 3-continued

| Ex. | Structure | Name | MS (ES) (M + H)+ |
|---|---|---|---|
| 15 | 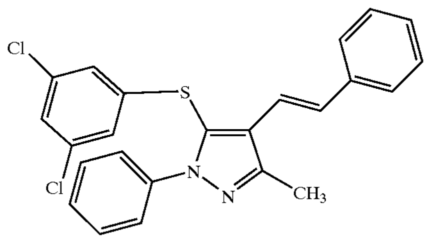 | 5-(3,5-Dichlorophenylthio)-3-methyl-1-phenyl-4-styryl-1H-pyrazole | 436 (M+; EI) |
| 16 | 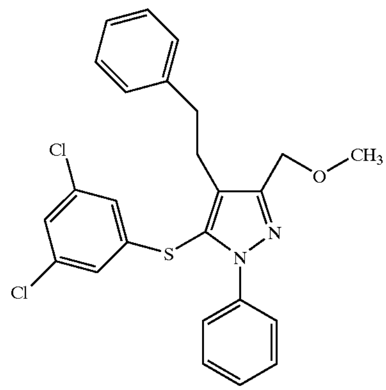 | 5-(3,5-Dichlorophenylthio)-3-(methoxymethyl)-1-phenyl-4-(2-phenylethyl)-1H-pyrazole | 469 |
| 17 | 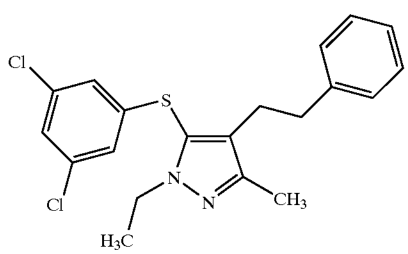 | 5-(3,5-Dichlorophenylthio)-1-ethyl-3-methyl-4-(2-phenylethyl)-1H-pyrazole | 390 (M+; EI) |

EXAMPLE 18

4-Benzyl-5-(3,5-Dichlorophenylthio)-1-Isopropyl-3-Methyl-1H-Pyrazole

A solution containing 30 mg of [5-(3,5-dichlorophenylthio)-1-isopropyl-3-methyl-1H-pyrazol-4-yl]-phenyl-methanol in 1 ml of trifluoroacetic acid was treated with 14 µl of triethylsilane. The mixture was stirred at rt for 15 min. The solvent was evaporated under reduced pressure and then the residue partitioned between diethyl ether/saturated sodium hydrogen carbonate and extracted three times. Combined extracts were washed with brine then dried over anhydrous magnesium sulphate, filtered and evaporated. The residue was purified by flash chromatography on silica gel using diethyl ether/hexane (1:7) for the elution to give 15 mg as a colourless gum. Mass spectrum (ES) m/z 391 [M+H]+. $^1$H NMR (DMSO-$d_6$) 1.27(d, 6H), 2.20(s, 3H), 3.79(s, 2H), 4.67(m, 1H), 6.82(d, 2H), 7.05 (d, 2H), 7.09 (t, 1H), 7.17 (t, 2H), 7.38(t, 1H). The starting material [5-(3,5-dichlorophenyl)-1-isopropyl-3-methyl-1H-pyrazol-4-yl]-phenyl-methanol was prepared as follows:

A solution containing 7.9 ml of hydrazine hydrate in 80 ml of ethanol was treated with 3.7 ml of 4-methoxybenzylchloride and heated at 90° C. for 2.0 h. The solvent was reduced by evaporation under reduced pressure and then the resulting residue was dissolved in 30 ml of ethanol. The solution was acidified with 30 ml of 5N HCl at 0° C. and a white precipitate separated. The white solid was filtered off and dried to give 2.75 g of (4-methoxybenzyl) hydrazine dihydrochloride (PMBNHNH$_2$.2HCl), which was used without further purification.

A solution containing 2.75 g of (4-methoxybenzyl) hydrazine dihydrochloride in 50 ml of toluene was treated with 1.7 ml of triethylamine at rt and then stirred for 5 min. The mixture was then treated with 1.32 ml of methyl acetoacetate and heated at 100° C. for 15 min. The solvent was evaporated under reduced pressure and then the residue partitioned between dichloromethane/10% citric acid and extracted three times. Combined extracts were washed with brine, then dried over anhydrous magnesium sulphate, filtered and evaporated to give a yellow solid. The solid was purified by flash chromatography on silica gel using methanol/dichloromethane (1:49) for the elution to give 2.3 g of 2-(4-methoxybenzyl)-5-methyl-2H-pyrazol-3-ol as a white solid. Mass spectrum (ES) m/z 219 [M+H]+.

A solution containing 1.0 g of 2-(4-methoxybenzyl)-5-methyl-2H-pyrazol-3-ol in 30 ml of dioxan was treated with 679 mg of calcium hydroxide and 800 µl of benzoyl chloride, then heated at 110° C. for 2 h. To the mixture was added 20 drops of water and the mixture heated for a further 2 h. The solvent was evaporated under reduced pressure and the residue partitioned between dichloromethane/10% citric acid. The organic phase was washed with brine, then dried over anhydrous magnesium sulphate, filtered and evaporated to give yellow oil. The oil was purified twice by flash chromatography on silica gel, initially using methanol/dichloromethane (1:49) to give a red solid, then ethyl acetate/hexane (1:1 to 2:1) for the elutions to give 400 mg of [5-hydroxy-1-(4-methoxybenzyl)-3-methyl-1H-pyrazol-4-yl]-phenyl-methanone as a yellow gum. Mass spectrum (ES) m/z 323 [M+H]⁺.

A solution containing 400 mg of [5-hydroxy-1-(4-methoxybenzyl)-3-methyl-1H-pyrazol-4-yl]-phenyl-methanone in 5 ml of phosphorus oxychloride was heated at 40° C. for 30 min. The mixture was poured into iced saturated sodium hydrogen carbonate and extracted with dichloromethane three times. The combined extracts were washed with brine then dried over anhydrous magnesium sulphate, filtered and evaporated. The residue was purified by flash chromatography on silica gel using diethyl ether/hexane (1:3) for the elution to give 170 mg of [5-chloro-1-(4-methoxybenzyl)-3-methyl-1H-pyrazol-4-yl]-phenyl-methanone as a yellow gum. Mass spectrum (ES) m/z 341[M+H]⁺.

A solution containing 170 mg of [5-chloro-1-(4-methoxybenzyl)-3-methyl-1H-pyrazol-4-yl]-phenyl-methanone in 10 ml of N,N-dimethylformamide was treated with 83 mg of potassium carbonate and 107 mg of 3,5-dichlorothiophenol. The mixture was heated at 100° C. for 4 h. The mixture was treated with a further 83 mg of potassium carbonate and 107 mg of 3,5-dichlorothiophenol. The mixture was then heated at 50° C. for 64 h. The mixture was treated with a further 83 mg of potassium carbonate and 107 mg of 3,5-dichlorothiophenol. The mixture was then heated at 100° C. for 2 h. The solvent was removed under reduced pressure and residue partitioned between dichloromethane/water, washed with brine then dried over anhydrous magnesium sulphate, filtered and evaporated. The residue was purified via flash chromatography on silica gel using diethyl ether/petroleum ether (1:4 to 1:3) to give 140 mg of [5-(3,5-dichlorophenylthio)-1-(4-methoxybenzyl)-3-methyl-1H-pyrazol-4-yl]-phenyl-methanone as a colourless oil. Mass spectrum (ES) m/z 483[M+H]⁺.

140 mg of [5-(3,5-dichlorophenylthio)-1-(4-methoxybenzyl)-3-methyl-1H-pyrazol-4-yl]-phenyl-methanone was treated with 4 ml of trifluoroacetic acid. The solution was then heated at reflux for 2 h. The solvent was evaporated under reduced pressure. The residue was then partitioned between dichloromethane/saturated sodium hydrogen carbonate, washed with brine then dried over anhydrous magnesium sulphate, filtered and evaporated to give 75 mg of [5-(3,5-dichlorophenylthio)-3-methyl-1H-pyrazol-4-yl]-phenyl-methanone as a yellow solid which was used without further purification. Mass spectrum (ES) m/z 363[M+H]⁺.

A solution containing 75 mg of [5-(3,5-dichlorophenylthio)-3-methyl-1H-pyrazol-4-yl]-phenyl-methanone in 2 ml of dry N,N-dimethylformamide (DMF) at rt under nitrogen was treated with 12 mg of sodium hydride. The mixture was then stirred for 2 min. To the mixture was added 25 µl of 2-iodopropane. The mixture was then stirred for 20 min. To the mixture was added 2 ml of water and then the mixture was extracted with ethyl acetate three times. Combined extracts were washed with brine then dried over anhydrous magnesium sulphate, filtered and evaporated. The residue 7; was purified by flash chromatography on silica gel using diethyl ether hexane (1:7) for the elution to give 32 mg of [5-(3,5-dichlorophenylthio)-1-isopropyl-3-methyl-1H-pyrazol-4-yl]-phenyl-methanone as a colourless oil. Mass spectrum (ES) m/z 405[M+H]⁺.

A solution containing 32 mg of [5-(3,5-dichlorophenylthio)-1-isopropyl-3-methyl-1H-pyrazol-4-yl]-phenyl-methanone in 2 ml of methanol was treated with 6 mg of sodium borohydride at rt under nitrogen. The mixture was then stirred at rt overnight. To the mixture was added 2 ml of water and then extracted with diethyl ether three times. Combined extracts were washed with brine then dried over anhydrous magnesium sulphate, filtered and evaporated to give 30 mg of [5-(3,5-dichlorophenylthio)-1-isopropyl-3-methyl-1H-pyrazol-4-yl]-phenyl-methanol as a white solid which was used without further purification. Mass spectrum (ES) m/z 407[M+H]⁺.

EXAMPLES 19–22

The compounds shown in table 4 were prepared in a manner analogous to that described in example 18:

TABLE 4

| Ex. | Structure | Name | MS (ES) (M + H)⁺ |
|---|---|---|---|
| 19 | 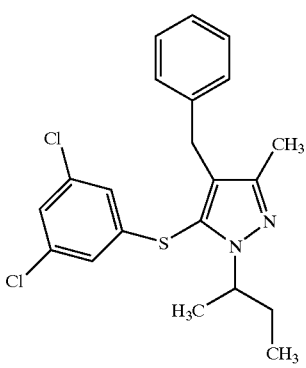 | 4-Benzyl-1-sec-butyl-5-(3,5-dichlorophenylthio)-3-methy-1H-pyrazole | 405 |

TABLE 4-continued

| Ex. | Structure | Name | MS (ES) (M + H)+ |
|---|---|---|---|
| 20 | 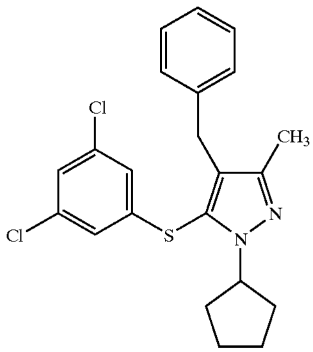 | 4-Benzyl-1-cyclopentyl-5-(3,5-dichlorophenylthio)-3-methyl-1H-pyrazole | 417 |
| 21 | 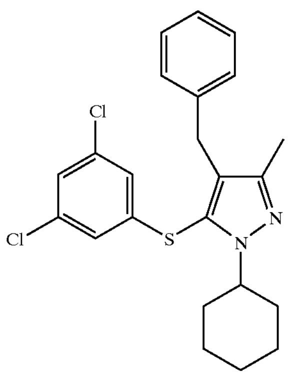 | 4-Benzyl-1-cyclohexyl-5-(3,5-dichlorophenylthio)-3-methyl-1H-pyrazole | 431 |
| 22 | 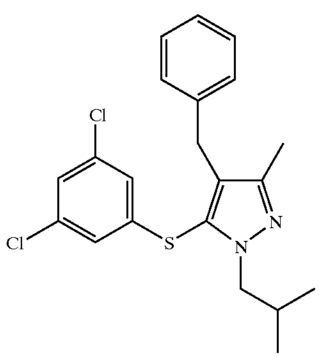 | 4-Benzyl-5-(3,5-dichlorophenylthio)-1-isobutyl-3-methyl-1H-pyrazole | 405 |

EXAMPLE 23

4-Benzyl-1-Ethyl-5-(4-Methoxyhenoxy)-3-Methyl-1H-Pyrazole

A solution containing 54 mg of [1-ethyl-5-(4-methoxyphenoxy)-3-methyl-1H-pyrazol-4-yl]-phenyl-methanol and 28 μl of triethylsilane in 2 ml of trifluoroacetic acid was stirred at room temperature for 22 h. The mixture was concentrated and saturated sodium hydrogen carbonate (6 ml) was added. The mixture was extracted three times with 8 ml of dichloromethane. The combined extracts were dried over magnesium sulphate, filtered and evaporated. The residue was purified by flash chromatography on silica gel using ethyl acetate/petroleum ether (bp 40–60° C.) (1:4) for the elution to give 33 mg of 4-benzyl-1-ethyl-5-(4-methoxyphenoxy)-3-methyl-1H-pyrazole as a yellow oil. Mass spectrum (ES) m/z 323 [M+H]+, 364 [M+H+CH₃CN]+. ¹H NMR (DMSO-d6) 1.19 (t, 3H), 2.00 (s, 3H), 3.46 (s, 2H), 3.70 (s, 3H), 3.80 (q, 2H), 6.82–6.89 (m, 4H), 7.01 (d, 2H), 7.12 (t, 1H), 7.20 (t, 2H).

The starting material [1-ethyl-5-(4-methoxyphenoxy)-3-methyl-1H-pyrazol-4-yl]-phenyl-methanol was prepared as followed:

A suspension of 3.9 g of ethyl hydrazine oxalate and 3.6 ml of triethylamine in 80 ml of toluene was stirred at room temperature for 15 min. 2.8 ml of methyl acetoacetate was added and the mixture was azeotroped for 1.5 h. The mixture was evaporated and the residue was purified by flash chromatography on silica gel using dichloromethane/methanol (97:3) for the elution to give 3.1 g of 2-ethyl-5-methyl-2H-pyrazol-3-ol as an orange solid.

A suspension of 1.4 g of 2-ethyl-5-methyl-2H-pyrazol-3-ol, 1.6 g of calcium hydroxide and 1.3 ml of benzoyl chloride in 70 ml of 1,4-dioxane was stirred at 110° C. for 3.5 h. 1 ml of water was added and the mixture was stirred at 110° C. for 2 h. 25 ml of 2N hydrochloric acid was added.

The mixture was stirred at room temperature for 16 h and extracted three times with 60 ml of ethyl acetate. The combined extracts were dried over magnesium sulphate, filtered and evaporated to give 3.1 g of (1-ethyl-5-hydroxy-3-methyl-1H-pyrazol-4-yl)-phenyl-methanone as a yellow oil which was used without further purification. Mass spectrum (ES) m/z 231 [M+H]$^+$, 272 [M+H+CH$_3$CN]$^+$.

A solution of 2.6 g of (1-ethyl-5-hydroxy-3-methyl-1H-pyrazol-4-yl)-phenyl-methanone in 4 ml of phosphorus oxychloride was stirred at 80° C. for 1.5 h. The mixture was poured into 300 ml of saturated sodium hydrogen carbonate and extracted three times with 70 ml of dichloromethane. The combined extracts were dried over magnesium sulphate, filtered and evaporated. The residue was purified by flash chromatography on silica gel using ethyl acetate/petroleum ether (bp 40–60° C.) (1:4) for the elution to give 1.74 g of (5-chloro-1-ethyl-3-methyl-1H-pyrazol-4-yl)-phenyl-methanone as a pale yellow liquid. Mass spectrum (ES) m/z 249 [M+H]$^+$, 290 [M+H+CH$_3$CN]$^+$.

A mixture of 129 mg of (5-chloro-1-ethyl-3-methyl-1H-pyrazol-4-yl)-phenyl-methanone, 141 mg of 4-methoxyphenol and 33 mg of sodium hydride (60% in mineral oil) in 3 ml of anhydrous N,N-dimethylformamide was stirred under nitrogen at 110° C. for 5 h. Water (8 ml) was added and the mixture was extracted three times with 10 ml of dichloromethane. The combined extracts were dried over magnesium sulphate, filtered and evaporated. The residue was purified by flash chromatography on silica gel using ethyl acetate/petroleum ether (bp 40–60° C.) (1:3) for the elution to give 100 mg of [1-ethyl-5-(4-methoxyphenoxy)-3-methyl-1H-pyrazol-4-yl]-phenyl-methanone as a yellow oil. Mass spectrum (ES) m/z 337 [M]$^+$, 378 [M+H+CH3CN]$^+$.

A solution of 77 mg of [1-ethyl-5-(4-methoxyphenoxy)-3-methyl-1H-pyrazol-4-yl]-phenyl-methanone and 119 mg of sodium borohydride in 5 ml of methanol was stirred at room temperature for 24 h. 20 ml of water was added and the mixture was extracted three times with 15 ml of diethyl ether. The combined extracts were dried over magnesium sulphate, filtered and evaporated to give 54 mg of [1-ethyl-5-(4-methoxyphenoxy)-3-methyl-1H-pyrazol-4-yl]-phenyl-methanol as a colourless gum which was used without further purification. Mass spectrum (ES) m/z 339 [M+H]$^+$, 380 [M+H+CH$_3$CN]$^+$.

EXAMPLE 24

4-Benzyloxymethyl-5-(3,5-Dichlorophenylthio)-3-Methyl-1-Phenyl-1H-Pyrazole

A solution containing 115 mg of [5-(3,5-dichlorophenylthio)-3-methyl-1-phenyl-1H-pyrazol-4-yl]-methanol, 54 mg of benzyl bromide and 38 mg of sodium hydride (60% in mineral oil) in 3 ml of anhydrous N,N-dimethylformamide was stirred under nitrogen at 100° C. for 2 hours. Water (10 ml) was added and the mixture was extracted three times with 8 ml of dichloromethane. Combined extracts were dried over magnesium sulphate, filtered and evaporated. The residue was purified twice by flash chromatography on silica gel using ethyl acetate/petroleum ether (bp 40–60° C.) (1:4) then dichloromethane for the elution to give 35 mg of 4-benzyloxymethyl-5-(3,5-dichlorophenylthio)-3-methyl-1-phenyl-1H-pyrazole as a colourless gum. Mass spectrum (ES) m/z 455 [M+H]$^+$, 496 [M+H+CH$_3$CN]$^+$. $^1$H NMR (DMSO-d$_6$) 2.36 (s, 3H), 4.47 (s, 2H), 4.49 (s, 2H), 6.96 (d, 2H), 7.24–7.47 (m, 11H).

The starting material [5-3,5-dichlorophenylthio)-3-methyl-1-phenyl-1H-pyrazol-4-yl]-methanol was prepared as follows:

A mixture of 1.35 g of 5-(3,5-dichlorophenylthio)-3-methyl-1-phenyl-1H-pyrazole-4-carboxaldehyde and 0.84 g of sodium borohydride in 10 ml of methanol was stirred at room temperature for 30 minutes. Water (10 ml) was added and the mixture was extracted four times with 15 ml of diethyl ether. Combined extracts were dried over magnesium sulphate, filtered and evaporated to leave 670 mg of [5-(3,5-dichloro-phenylsulphanyl)-3-methyl-1-phenyl-1H-pyrazol-4-yl]methanol as a grey paste which was used without further purification. Mass spectrum (ES) m/z 365 [M+H]$^+$, 406 [M+H+CH$_3$CN]$^+$.

EXAMPLE 25

2-[5-(3,5-Dichloro-Phenylsulfanyl)-1-Isopropyl-3-Methyl-1H-Pyrazol-4-Ylmethoxy]-Pyridine To a solution of 75 mg of [5-(3,5-dichlorophenyl)-1-isopropyl-3-methyl-1H-pyrazol-4-yl]-methanol in 8 mL of tetrahydronfuran was added 24 mg of 3-hydroxypyridine, 71 mg of triphenylphosphine and 43 µL of diethylazodicarboxylate. The reaction mixture was stirred at room temperature for 3 hours. Additional 24 mg of 3-hydroxypyridine, 71 mg of triphenylphosphine and 43 µL of diethylazodicarboxylate were added and the reaction stirred over night at room temperature. The solvent was evaporated and the residue partitioned between dichloromethane and water. The aqueous phase was extracted three times with 10 ml of dichloromethane. Combined extracts were dried over magnesium sulphate, filtered and evaporated. The residue was purified twice by flash chromatography on silica gel using diethyl ether/hexane (1:2 then 2:1) for the elution to give 100 mg of 2-[5-(3,5-dichloro-phenylsulfanyl)-1-isopropyl-3-methyl-1H-pyrazol-4-ylmethoxy]-pyridine as a yellow gum. Mass spectrum (ES) m/z 408 [M+H]$^+$.

The starting material [5-(3,5-dichlorophenyl)-1-isopropyl-3-methyl-1H-pyrazol-4-yl]-methanol was prepared as follows:

A mixture of 1.27 g of 5-hydroxy-1-isopropyl-3-methyl-1H-pyrazole, 3.4 mL of phosphorus oxychloride and 5.2 mL of dimethylformamide were heated at 100° C. under nitrogen for 1 hour. The reaction mixture was allowed to cool to room temperature and then partitioned between 20 mL of saturated sodium bicarbonate solution and 20 mL of dichloromethane. The aqueous phase was extracted twice with 20 ml of dichloromethane. Combined extracts were dried over magnesium sulphate, filtered and evaporated. The yellow residue was purified by flash chromatography on silica gel using ethyl acetate/diethyl ether (1:5 then 1:4) for the elution to give 213 mg of (5-chloro-1-isopropyl-3-methyl-1H-pyrazol-4-yl)-carbaldehyde as a white solid. Mass spectrum (ES) m/z 228 [M+H+MeCN]$^+$.

To a solution of 213 mg of (5-chloro-1-isopropyl-3-methyl-1H-pyrazol-4-yl)-carbaldehyde in 3 mL of N,N-dimethylformamide was added 245 mg of 3,5-dichlorothiophenol and 190 mg of potassium carbonate. The reaction mixture was heated at 60° C. for 2 hours then a further 125 mg of 3,5-dichlorothiophenol and 95 mg of potassium carbonate were added. The mixture was heated at 60° C. for a further 1 hour then cooled to room temperature overnight. The solvent was evaporated and the residue partitioned between 20 mL of dichloromethane and 20 mL of water. The aqueous phase was extracted twice with 10 mL of dichloromethane and combined extracts were washed with brine, dried, filtered and evaporated to give a yellow oil which was purified by flash chromatography on silica gel using diethyl ether/hexane (1:7 then 1:5) for the elution to give 317 mg of [5-(3,5-dichlorophenyl)-1-isopropyl-3-methyl-1H-pyrazol-4-yl]-carbaldehyde as a white solid. Mass spectrum (ES) m/z 329 [M+H]+.

To a solution of 1.07 g of [5-(3,5-dichlorophenyl)-1-isopropyl-3-methyl-1H-pyrazol-4-yl]-carbaldehyde in 30 mL of methanol at room temperature was added 740 mg of sodium borohydride portionwise. The reaction mixture was stirred at room temperature for 5 hours then quenched with 5 mL of water. The aqueous phase was extracted three times with 10 mL of ethyl acetate and combined extracts were washed with brine, dried, filtered and evaporated to give [5-(3,5-dichlorophenyl)-1-isopropyl-3-methyl-1H-pyrazol-4-yl]-methanol as a colourless oil. Mass spectrum (ES) m/z 331 [M+H]+.

EXAMPLE 26

1-[5-(3,5-Dichloro-Phenylsulfanyl)-1-Isopropyl-3-Methyl-1H-Pyrazol-4-Ylmethyl]-1H-Pyridin-2-One To a solution of 119 mg of [5-(3,5-dichlorophenyl)-1-isopropyl-3-methyl-1H-pyrazol-4-yl]-methanol in 5 mL of dichloromethane was added 43 mg of 2-hydroxypyridine, 113 µL of tributylphosphine and 78 mg of TMAD. The reaction 1 mixture was stirred at room temperature for 2 hours then the solvent was evaporated. The residue was purified by flash chromatography on silica gel using diethyl ether/petrol (1:5 up to 3:1) for the elution to give 317 mg of 1-[5-(3,5-dichloro-phenylsulfanyl)-1-isopropyl-3-methyl-1H-pyrazol-4-ylmethyl]-1H-pyridin-2-one as a colourless gum. Mass spectrum (ES) m/z 329 [M+H]+.

EXAMPLE 27

4-[5-(3,5-Dichloro-Phenylsulfanyl)-1-Isopropyl-3-Methyl-1H-Pyrazol-4-Ylmethoxymethyl]-Pyridine To a solution of 100 mg of [5-(3,5-dichlorophenyl)-1-isopropyl-3-methyl-1H-pyrazol-4-yl]-methanol in 3 mL of N,N-dimethylformamide was added 24 mg of sodium hydride (60% dispersion in oil). The mixture was stirred for 5 minutes then 96 mg of 4-bromomethylpyridine.hydrobromide was added. The reaction mixture was stirred at room temperature for 1 hour then quenched with 5 mL of water. The aqueous phase was extracted three times with 10 mL of dichloromethane and combined extracts were washed with brine, dried, filtered and evaporated to give a red oil which was purified by flash chromatography on silica gel using ethyl acetate/hexane (1:2 then 1:1) for the elution to give 62 mg of 4-[5-(3,5-dichloro-phenylsulfanyl)-1-isopropyl-3-methyl-1H-pyrazol-4-ylmethoxymethyl-]-pyridine as a colourless gum. Mass spectrum (ES) m/z 422 [M+H]+, 463 [M+H+MeCN]+.

EXAMPLE 28

4-[[5-(3,5-Dichloro-Phenylsulfanyl)-1-Isopropyl-3-Methyl-1H-Pyrazol-4-yl]-Hydroxy-Methyl]-Pyridine 593 mg of 4-Bromopyridine.hydrobromide was treated with 15 mL of 5% aqueous sodium hydrogen carbonate and extracted three times with 20 mL of diethyl ether and combined extracts were washed with brine, dried, filtered and evaporated to give a colourless oil which was dissolved in 3 mL of tetrahydrofuran. To this solution, under nitrogen at room temperature, was added 1.52 mL of a 3.0 M solution of isopropyl magnesium chloride in diethyl ether. The reaction mixture was stirred at room temperature for 1.5 hours then a solution of 1.0 g of [5-(3,5-dichlorophenyl)-1-isopropyl-3-methyl-1H-pyrazol-4-yl]-carbaldehyde in 10 mL of tetrahydrofuran was added. The reaction mixture was stirred at room temperature overnight then 20 mL of water added. The aqueous phase was extracted three times with 10 mL of dichloromethane and combined extracts were washed with brine, dried, filtered and evaporated to give a yellow oil which was purified by flash chromatography on silica gel using ethyl acetate/hexane (1:2 then 2:1) for the elution to give 835 mg of 4-[[5-(3,5-dichloro-phenylsulfanyl)-1-isopropyl-3-methyl-1H-pyrazol-4-yl]-hydroxy-methyl]-pyridine as a colourless gum. Mass spectrum (ES) m/z 408 [M+H]+, 449 [M+H+MeCN]+.

EXAMPLE 29

4-[5-(3,5-Dichloro-Phenylsulfanyl)-1-Isopropyl-3-Methyl-1H-Pyrazol-4-Ylmethyl]-Pyridine A solution of 466 mg of phosphorus tetraiodide in 15 mL of benzene was heated at 80° C. for 15 minutes. To this solution was added dropwise a solution of 400 mg of 4-[[5-(3,5-dichloro-phenylsulfanyl)-1-isopropyl-3-methyl-1H-pyrazol-4-yl]-hydroxy-methyl]-pyridine in 10 mL of benzene. The mixture was then heated at 80° C. for 1 hour then allowed to cool to room temperature. Then 8 mL of 10% aqueous sodium bisulphite solution was added and the biphasic mixture stirred for 1 hour. The aqueous phase was extracted three times with 30 mL of ethyl acetate and combined extracts were washed with brine, dried, filtered and evaporated to give a yellow residue which was purified by flash chromatography on silica gel using ethyl acetate/hexane (1:1 then 2:1) for the elution to give 238 mg of 4-[5-(3,5-dichloro-phenylsulfanyl)-1-isopropyl-3-methyl-1H-pyrazol-4-ylmethyl]-pyridine as a white solid. Mass spectrum (ES) m/z 392 [M+H]+, 433 [M+H+MeCN]+.

EXAMPLE 30

4-[[5-(3,5-Dichloro-Phenylsulfanyl)-1-Isopropyl-3-Methyl-1H-Pyrazol-4-yl]-Fluoro-Methyl]-Pyridine To a −78° C. solution of 200 mg of 4-[[5-(3,5-dichloro-phenylsulfanyl)-1-isopropyl-3-methyl-1H-pyrazol-4-yl]-hydroxy-methyl]-pyridine in 5 mL of dichloromethane was added 68 µL of diethylamino sulfur trifluoride. The reaction mixture was stirred for 1 hour at −78° C. then quenched with saturated aqueous sodium hydrogen carbonate. The aqueous phase was extracted three times with 10 mL of dichloromethane and combined extracts were washed with brine, dried, filtered and evaporated to give a blue gum which was purified by flash chromatography on silica gel using diethyl ether/hexane (1:2 then 1:1) for the elution to give 118 mg of 4-[[5-(3,5-Dichloro-phenylsulfanyl)-1-isopropyl-3-methyl-1H-pyrazol-4-yl]-fluoro-methyl]-pyridine as a colourless oil. Mass spectrum (ES) m/z 410 [M+H]+, 451 [M+H+MeCN]+.

EXAMPLE 31

4-[5-(3,5-Dichloro-Phenylsulfanyl)-1-Isopropyl-3-Methyl-1H-Pyrazol-4-Ylmethyl]-3-Fluoro-Pyridine A solution of 278 mg of phosphorus tetraiodide in 10 mL of toluene was heated at 80° C. for 20 minutes. To this solution was added dropwise a solution of 259 mg of 4-[[5-(3,5-dichloro-phenylsulfanyl)-1-isopropyl-3-methyl-1H-pyrazol-4-yl]-hydroxy-methyl]-pyridine in 5 mL of benzene. The mixture was then heated at 80° C. for 20 minutes then allowed to cool to room temperature. Then 10 mL of 10% aqueous sodium bisulphite solution was added and the biphasic mixture stirred for 1 hour. The aqueous phase was extracted three times with 20 mL of ethyl acetate and combined extracts were washed with brine, dried, filtered and evaporated to give a yellow oil which was purified by flash chromatography on silica gel using diethyl ether/hexane (1:1 then 2:1) for the elution to give 35 mg of 4-[5-(3,5-Dichloro-phenylsulfanyl)-1-isopropyl-3-methyl-1H-pyrazol-4-ylmethyl]-3-fluoro-pyridine as a pale yellow solid. Mass spectrum (ES) m/z 410 [M+H]$^+$, 451 [M+H+MeCN]$^+$.

The starting material 4-[5-(3,5-dichloro-phenylsulfanyl)-1-isopropyl-3-hydroxymethyl-1H-pyrazol-4-ylmethyl]-3-fluoro-pyridine was prepared as follows:

To a −78° C. solution of 65 μL of 3-fluoropyridine in 2.5 mL of anhydrous tetrahydrofuran was added 381 μL of a 2M solution of lithium diisopropylamide in heptane/tetrahydrofuran/ethylbenzene. The mixture was stirred at −78° C. for 1 hour then treated dropwise with a solution of 250 mg of [5-(3,5-dichlorophenyl)-1-isopropyl-3-methyl-1H-pyrazol-4-yl]-carbaldehyde in 2 mL of anhydrous tetrahydrofuran. The reaction mixture was stirred for 30 minutes then allowed to warm to room temperature when it was quenched with water. The aqueous phase was extracted three times with 20 mL of diethyl ether and combined extracts were washed with brine, dried, filtered and evaporated to give a yellow oil which was purified by flash chromatography on silica gel using ethyl acetate/hexane (1:3 then 1:1) for the elution to give 259 mg of 4-[5-(3,5-dichloro-phenylsulfanyl)-1-isopropyl-3-hydroxymethyl-1H-pyrazol-4-ylmethyl]-3-fluoro-pyridine as a colourless oil. Mass spectrum (ES) m/z 426 [M+H]$^+$, 467 [M+H+MeCN]$^+$.

EXAMPLE 32

[5-(3,5-Dichloro-Phenylsulphanyl)-1-Ethyl-3-Methyl-1H-Pyrazol-4-Ylmethyl]-Pyridin-3-Yl-Amine A mixture of 227 mg of 4-bromoethyl-5-(3,5-dichloro-phenylsulphanyl)-1-ethyl-3-methyl-1H-pyrazole, 62 mg of 3-aminopyridine and 36 mg of sodium hydride (60% in mineral oil) in 3 ml of anhydrous N,N-dimethylformamide was stirred under nitrogen at 110° C. for 15 minutes. Water (10 ml) was added and the mixture was extracted three times with 8 ml of dichloromethane. The combined extracts were dried over magnesium sulphate, filtered and evaporated. The residue was purified by flash chromatography on silica gel using dichloromethane/methanol for the elution to give 17 mg of [5-(3,5-dichloro-phenylsulphanyl)-1-ethyl-3-methyl-1H-pyrazol-4-ylmethyl]-pyridin-3-yl-amine as a brown gum. $^1$H NMR (DMSO-d$_6$) 1.19 (t, 3H), 2.27 (s, 3H), 4.05–4.11 (m, 4H), 6.03 (t, 1H), 6.87 (d, 1H), 6.99 (m, 1H), 7.04 (d, 2H), 7.44 (t, 1H), 7.72 (dd, 1H), 7.94 (d, 1H).

The starting material 4-bromoethyl-5-(3,5-dichloro-phenylsulphanyl)-1-ethyl-3-methyl-1H-pyrazole was prepared as follow:

A suspension of 23 g of ethyl hydrazine oxalate and 22 ml of triethylamine in 500 ml of toluene was stirred at room temperature for 15 minutes. 17 ml of methyl acetoacetate was added and the mixture was azeotroped for 1.5 hours. The mixture was evaporated and the residue was purified by flash chromatography on silica gel using dichloromethane/methanol (97:3) for the elution to give 19 g of 2-ethyl-5-methyl-2H-pyrazol-3-ol as an orange solid.

To 28.7 ml of anhydrous N,N-dimethylformamide at 0° C. were added slowly 80.7 ml of phosphorus oxychloride then 15.6 g of 2-ethyl-5-methyl-2H-pyrazol-3-ol. The mixture was stirred under nitrogen at 80° C. for 1 hour, poured into 700 ml of water at 0° C. then extracted six times with 350 ml of diethyl ether. The combined extracts were dried over magnesium sulphate, filtered and evaporated to leave 9.3 g of 5-chloro-1-ethyl-3-methyl-1H-pyrazole-4-carbaldehyde as an orange liquid which was used without further purification.

A mixture of 9.2 g of 5-chloro-1-ethyl-3-methyl-1H-pyrazole-4-carbaldehyde, 14.3 g of 3,5-dichlorothiophenol and 11.8 g of potassium carbonate in 40 ml of anhydrous N,N-dimethylformamide was stirred under nitrogen at 100° C. for 18 hours. Water (200 ml) was added and the mixture was extracted three times with 100 ml of dichloromethane. The combined extracts were dried over magnesium sulphate, filtered and evaporated. The residue was purified by flash chromatography on silica gel using dichloromethane/petroleum ether (bp 40–60° C.) for the elution to give 12.2 g of 5-(3,5-dichloro-phenylsulphanyl)-1-ethyl-3-methyl-1H-pyrazole-4-carbaldehyde as an orange solid. Mass spectrum (ES) m/z 356 [M+CH$_3$CN+H]$^+$.

A mixture of 1.1 g of 5-(3,5-dichloro-phenylsulphanyl)-1-ethyl-3-methyl-1H-pyrazole-4-carbaldehyde and 0.53 g of sodium borohydride in 25 ml of anhydrous methanol was stirred under nitrogen at room temperature for 15 minutes. Water (25 ml) was added and the mixture was extracted three times with 20 ml of diethyl ether. The combined extracts were dried over magnesium sulphate, filtered and evaporated. The residue was purified by flash chromatography on silica gel using ethyl acetate/petroleum ether (bp 40–60° C.) (1:3) for the elution to give 902 mg of [5-(3,5-dichloro-phenylsulphanyl)-1-ethyl-3-methyl-1H-pyrazol-4-yl]-methanol as a yellow oil. Mass spectrum (ES) m/z 317 [M+H]$^+$.

A mixture of 460 mg of [5-(3)5-dichloro-phenylsulphanyl)-1-ethyl-3-methyl-1H-pyrazol-4-yl]-methanol, 481 mg of carbon tetrabromide and 380 mg of triphenylphosphine in 20 ml of dichloromethane was stirred at room temperature for 24 hours. The solvent was evaporated. The residue was purified by flash chromatography on silica gel using ethyl acetate/petroleum ether (bp 40–60° C.) (1:4) for the elution to give 392 mg of 4-bromoethyl-5-(3,5-dichloro-phenylsulfanyl)-1-ethyl-3-methyl-1H-pyrazole as a pale yellow oil. Mass spectrum (ES) m/z 317 [M-Br+H$_2$O ]$^+$.

The compounds shown in table 5 were prepared in a manner analogous to that described above:

TABLE 5

| Ex. | Structure | Name | MS ES (M + H)+ |
|---|---|---|---|
| | | 2-[4-Benzyl-5-(3,5-dichloro-phenylsulfanyl)-3-methyl pyrazol-1-yl]-pyridine | 427 |
| | | 4-Benzyl-3-methyl-5-(3-nitro-phenoxy)-1-phenyl-1H-pyrazole | 386 |
| | | 3-(4-Benzyl-5-methyl-2-phenyl-2H-pyrazol-3-yloxy)-benzonitrile | 366 |
| | | 2-[5-(3,5-Dichloro-phenylsulfanyl)-1-isopropyl-3-methyl-1H-pyrazol-4-ylmethyl]-pyridine | 393 |

TABLE 5-continued

| Ex. | Structure | Name | MS ES (M + H)+ |
|---|---|---|---|
| | | 4-Benzyloxymethyl-5-(3,5-dichloro-phenylsulfanyl)-1-isopropyl-3-methyl-1H-pyrazole | 422 |
| | | 2-[5-(3,5-Dimethyl-phenylsulfanyl)-1-isopropyl-3-methyl-1H-pyrazol-4-ylmethyl]-pyridine | 352 |
| | | 2-[5-(3-Chloro-phenylsulfanyl)-1-isopropyl-3-methyl-1H-pyrazol-4-ylmethyl]-pyridine | 359 |
| 25 | 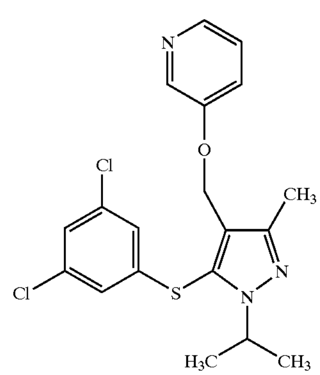 | 2-[5-(3,5-Dichloro-phenylsulfanyl)-1-isopropyl-3-methyl-1H-pyrazol-4-ylmethoxy]-pyridine | 409 |

TABLE 5-continued

| Ex. | Structure | Name | MS ES (M + H)+ |
|---|---|---|---|
|  |  | 3-Chloro-5-[5-(3,5-dichloro-phenylsulfanyl)-1-isopropyl-3-methyl-1H-pyrazol-4-ylmethoxy]-pyridine | 443 |
| 26 | 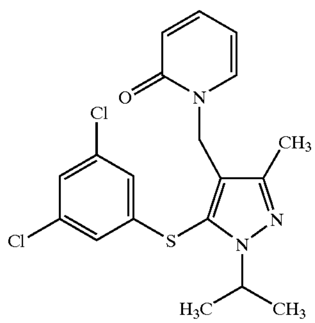 | 1-[5-(3,5-Dichloro-phenylsulfanyl)-1-isopropyl-3-methyl-1H-pyrazol-4-ylmethyl]-1H-pyridin-2-one | 409 |
|  |  | 3-[5-(3,5-Dichloro-phenylsulfanyl)-1-ethyl-3-methyl-1H-pyrazol-4-ylmethyl]-pyridine | 379 |
|  |  | 3-[5-(3,5-Dichloro-phenylsulfanyl-1-isopropyl-3-methyl-1H-pyrazol-4-ylmethyl]-3H-pyrimidin-4-one | 379 |

TABLE 5-continued

| Ex. | Structure | Name | MS ES (M + H)+ |
|---|---|---|---|
| 27 | 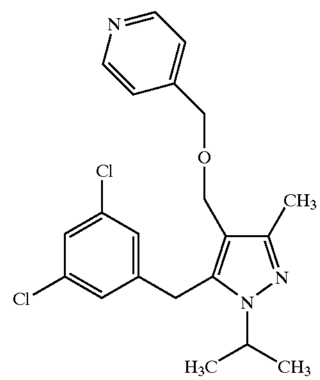 | 4-[5-(3,5-Dichloro-phenylsulfanyl)-1-isopropyl-3-methyl-1H-pyrazol-4-ylmethoxymethyl]-pyridine | 423 |
| | | 3-(4-Benzyl-5-methyl-2-phenyl-2H-pyrazol-3-ylsulfanyl)-benzonitrile | 382 |
| | | 3-[5-(3,5-Dichloro-phenylsulfanyl)-1-isopropyl-3-methyl-1H-pyrazol-4-ylmethyl]-pyridine | 393 |
| | | [5-(3,5-Dichloro-phenylsulfanyl)-1-isopropyl-3-methyl-1H-pyrazol-4-yl]-pyridin-2-yl-methanol | 409 |

TABLE 5-continued

| Ex. | Structure | Name | MS ES (M + H)+ |
|---|---|---|---|
|  |  | [5-(3,5-Dichloro-phenylsulfanyl)-1-isopropyl-3-methyl-1H-pyrazol-4-yl]-pyridin-4-yl-methanol |  |
| 29 | 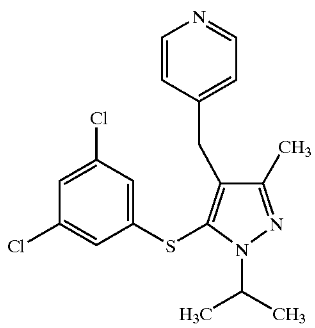 | 4-[5-(3,5-Dichloro-phenylsulfanyl)-1-isopropyl-3-methyl-1H-pyrazol-4-ylmethyl]-pyridine | 392 |
|  |  | 4-[5-(3,5-Dichloro-phenylsulfanyl)-1-isopropyl-3-methyl-1H-pyrazol-4-ylmethylsulfanyl]-pyridine |  |
|  |  | 4-Benzyl-5-(3,5-dichloro-phenylsulfanyl)-3-methyl-1-(2,2,2-trifluoro-ethyl)-1H-pyrazole |  |

TABLE 5-continued

| Ex. | Structure | Name | MS ES (M + H)+ |
|---|---|---|---|
| 30 | 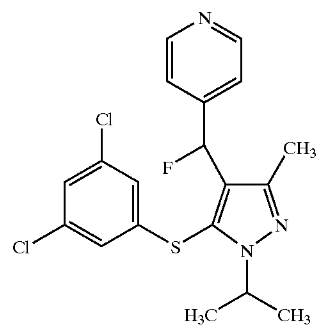 | 4-{[5-(3,5-Dichloro-phenylsulfanyl)-1-isopropyl-3-methyl-1H-pyrazol-4-yl]-fluoro-methyl}-pyridine | 410 |
| | | 5-[5-(3,5-Dichloro-phenylsulfanyl)-1-ethyl-3-methyl-1H-pyrazol-4-ylmethoxy]-2-methyl-pyridine | |
| | | 5-Bromo-4-[5-(3,5-dichloro-phenylsulfanyl)-1-isopropyl-3-methyl-1H-pyrazol-4-ylmethyl]-pyrimidine | |
| | | 3-[5-(3,5-Dichloro-phenylsulfanyl)-1-ethyl-3-methyl-1H-pyrazol-4-ylmethoxy]-2-nitro-pyridine | |

TABLE 5-continued

| Ex. | Structure | Name | MS ES (M + H)+ |
|---|---|---|---|
| | | 4-[5-(3,5-Dichloro-phenylsulfanyl)-1-ethyl-3-methyl-1H-pyrazol-4-ylmethylsulfanyl]-pyridine | 411 |
| | | 4-[5-(3,5-Dichloro-phenylsulfanyl)-1-ethyl-3-methyl-1H-pyrazol-4-ylmethoxy]-pyridine | 395 |
| | | 4-[5-(3,5-Dichloro-phenylsulfanyl)-1-isopropyl-3-methyl-1H-pyrazol-4-ylmethyl]-pyrimidine | 394 |
| | | 3-[5-(3,5-Dichloro-phenylsulfanyl)-1-ethyl-3-methyl-1H-pyrazol-4-ylmethoxy]]-pyridin-2-ylamine | 410 |

TABLE 5-continued

| Ex. | Structure | Name | MS ES (M + H)+ |
|---|---|---|---|
|  |  | 4-[5-(3,5-Dichloro-phenylsulfanyl)-1-isopropyl-3-methyl-1H-pyrazol-4-ylmethoxy]-pyridine | 409 |
| 31 | 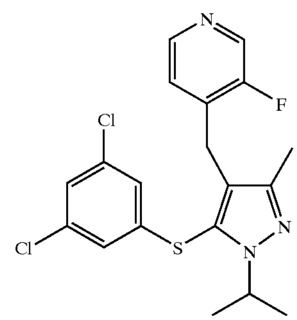 | 4-[5-(3,5-Dichloro-phenylsulfanyl)-1-isopropyl-3-methyl-1H-pyrazol-4-ylmethyl]-3-fluoro-pyridine | 411 |
|  |  | 4-[5-(3,5-Dichloro-phenylsulfanyl)-1-ethyl-3-methyl-1H-pyrazol-4-ylmethyl]-3-fluoro-pyridine | 397 |
|  |  | 3-Chloro-4-[5-(3,5-dichloro-phenylsulfanyl)-1-ethyl-3-methyl-1H-pyrazol-4-ylmethyl]-pyridine | 413 |

TABLE 5-continued

| Ex. | Structure | Name | MS ES (M + H)+ |
|---|---|---|---|
|  |  | 3-Chloro-4-[5-(3,5-dichloro-phenylsulfanyl)-1-isopropyl-3-methyl-1H-pyrazol-4-ylmethyl]-pyridine | 427 |
|  |  | 4-[5-(3,5-Dichloro-phenylsulfanyl)-1-ethyl-3-methyl-1H-pyrazol-4-ylmethoxy]-6-methyl-pyrimidin-2-ylamine | 425 |
|  |  | 3-Bromo-5-[5-(3,5-dichloro-phenylsulfanyl)-1-ethyl-3-methyl-1H-pyrazol-4-ylmethyl]-pyridine | 458 |
| 32 | 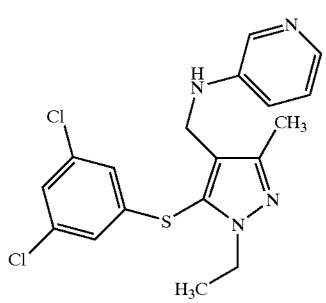 | [5-(3,5-Dichloro-phenylsulfanyl)-1-ethyl-3-methyl-1H-pyrazol-4-ylmethyl]-pyridin-3-yl-amine | 394 |

TABLE 5-continued

| Ex. | Structure | Name | MS ES (M + H)+ |
|---|---|---|---|
| | | 4-[5-(3,5-Dichloro-phenylsulfanyl)-1-isopropyl-3-methyl-1H-pyrazol-4-ylmethyl]-benzonitrile | 417 |
| | | 2-Chloro-4-[5-(3,5-dichloro-phenylsulfanyl)-1-isopropyl-3-methyl-1H-pyrazol-4-ylmethyl]-pyridine | 427 |
| | | 2-Chloro-4-[5-(3,5-dichloro-phenylsulfanyl)-1-isopropyl-3-methyl-1H-pyrazol-4-ylmethyl]-6-methyl-pyridine | 441 |
| | | 2-[5-(3,5-Dichloro-phenylsulfanyl)-1-isopropyl-3-methyl-1H-pyrazol-4-ylmethyl]-pyrazine | 394 |

TABLE 5-continued

| Ex. | Structure | Name | MS ES (M + H)+ |
|-----|-----------|------|----------------|
| | | 4-[5-(3-Chloro-5-methoxy-phenylsulfanyl)-1-isopropyl-3-methyl-1H-pyrazol-4-ylmethyl]-2-methoxy-pyridine | 419 |
| | | 3-[[5-(3,5-Dichlorophenylthio)-3-methyl-1-phenyl-1H-pyrazol-4-yl]methyl]-2-(methylthio)pyridine | 473 |
| | | 4-[5-(3-Bromo-phenylsulfanyl)-1-isopropyl-3-methyl-1H-pyrazol-4-ylmethyl]-3-chloro-pyridine | 437 |
| | | 3-Chloro-4-(1-isopropyl-3-methyl-5-m-tolylsulfanyl-1H-pyrazol-4-ylmethyl)-pyridine | 373 |

TABLE 5-continued

| Ex. | Structure | Name | MS ES (M + H)+ |
|---|---|---|---|
| | | 3-Chloro-4-[5-(3,5-dimethyl-phenylsulfanyl)-1-isopropyl-3-methyl-1H-pyrazol-4-ylmethyl]-pyridine | 387 |
| | | 4-[5-(3-Bromo-phenylsulfanyl)-1-isopropyl-3-methyl-1H-pyrazol-4-ylmethyl]-3-fluoro-pyridine | 421 |
| | | 3-Fluoro-4-(1-isopropyl-3-methyl-5-m-tolylsulfanyl-1H-pyrazol-4-ylmethyl)-pyridine | 356 |
| | | 4-[5-(3,5-Dimethyl-phenylsulfanyl)-1-isopropyl-3-methyl-1H-pyrazol-4-ylmethyl]-3-fluoro-pyridine | 370 |
| | | 5-(3,5-Dichloro-phenylsulfanyl)-1-isopropyl-3-methyl-4-thiophen-3-ylmethyl-1H-pyrazole | 398 |

| Ex. | Structure | Name | MS ES (M + H)+ |
|---|---|---|---|
| | 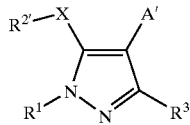 | {3-[5-(3,5-Dichloro-phenylsulfanyl)-1-isopropyl-3-methyl-1H-pyrazol-4-ylmethyl]-phenyl}-dimethyl-amine | 435 |
| | | 4-[5-(3,5-Dichloro-phenylsulfanyl)-1-isopropyl-3-methyl-1H-pyrazol-4-ylmethyl]-3,5-dimethyl-isoxazole | 411 |
| | | 6-[5-(3,5-Dichloro-phenylsulfanyl)-1-isopropyl-3-methyl-1H-pyrazol-4-ylmethyl]-pyridine-2-carbonitrile | 418 |

What is claimed is:

1. A compound of the formula wherein $R^1$ is optionally substituted $C_{1-12}$-alkyl, $C_{3-8}$-cycloalkyl, acyl, $C_{1-4}$-alkylsulfonyl, optionally substituted phenylsulfonyl, aryl, heterocyclyl or $C_{1-4}$-alkyl substituted with phenyl, wherein the heterocycle is furyl, 1-pyrrolyl, 2-pyrrolyl, 1-thiophenyl, 2-thiophenyl, 2-pyridinyl (2-pyridyl), 3-pyridinyl (3-pyridyl), 4-pyridinyl (4-pyridyl), 1H-pyridin-2-one, 1H-pyridin-4-one, 3H-pyrimidine-4-one, pyridazine (1,2-diazine), pyrimidine (1,3-diazine), pyrazine (1,4-diazine), oxazole or isoxazole (iso-oxazole), the substituted $C_{1-12}$-alkyl is substituted with 1–5 substituents selected from fluorine, chlorine and bromine, and the substituted phenyl is substituted with 1–5 substituents selected from $C_{1-4}$-alkyl, $C_{1-4}$-alkoxy, hydroxy, fluorine, chlorine, bromine and cyano;

$R^{2'}$ is phenyl or phenyl substituted with 1–5 substituents selected from $C_{1-4}$-alkyl, $C_{1-4}$-alkoxy, hydroxy, fluorine, chlorine, bromine, cyano and nitro;

$R^3$ is $C_{1-12}$-alkyl or $C_{1-4}$-alkoxy-$C_{1-4}$-alkyl;

A' is a group selected from $CH_2$-(aryl-$C_{1-4}$-alkylamino), $CH_2$-(aryl-$C_{1-4}$-alkoxy), $C_{1-4}$-alkyl substituted with unsubstituted aryl, aryl substituted with 1–5 substituents selected from $C_{1-4}$-alkyl, $C_{1-4}$-alkoxy, hydroxy, fluorine, chlorine, bromine, cyano, S—$C_{1-4}$-alkyl and NRR', unsubstituted 4-pyridyl, or 4-pyridyl substituted with 1–4 substituents selected from $C_{1-4}$-alkyl, $C_{1-4}$-alkoxy, hydroxy, fluorine, chlorine, bromine, cyano, S—$C_{1-4}$-alkyl and NRR', wherein R and R' are independently of each other hydrogen or $C_{1-4}$-alkyl, or $CH_2$-(heterocyclyl-$C_{1-4}$-alkoxy) wherein the heterocycle is furyl, 1-pyrrolyl, 2-pyrrolyl, 1-thiophenyl, 2-thiophenyl, 2-pyridinyl (2-pyridyl), 3-pyridinyl (3-pyridyl), 4-pyridinyl (4-pyridyl), 1H-pyridin-2-one, 1H-pyridin-4-one, 3H-pyrimidine-4-one, pyridazine (1,2-diazine), pyrimidine (1,3-diazine), pyrazine (1,4-diazine), oxazole or isoxazole (iso-oxazole); or A' is a group of formula $CH_2$-U-heterocyclyl,
   wherein the heterocycle is furyl, 1-pyrrolyl, 2-pyrrolyl, 1-thiophenyl, 2-thiophenyl, 2-pyridinyl (2-pyridyl), 3-pyridinyl (3-pyridyl), 4-pyridinyl (4-pyridyl), 1H-pyridin-2-one, 1H-pyridin-4-one, 3H-pyrimidine-4-one, pyridazine (1,2-diazine), pyrimidine (1,3-diazine), pyrazine (1,4-diazine), oxazole or isoxazole (iso-oxazole),
   wherein U is O, S or NR", wherein R" is hydrogen or $C_{1-4}$-alkyl, and
   wherein heterocyclyl is optionally substituted with 1–4 substituents selected from $C_{1-4}$-alkyl, fluorine, chlorine, bromine, cyano, nitro and NRR', wherein R and R' are independently of each other hydrogen or $C_{1-4}$-alkyl; or A' is a group of formula CH(OH)aryl; or A' is a group of formula CH=CHW
   wherein W is unsubstituted aryl, aryl substituted with 1–5 substituents selected from $C_{1-4}$-alkyl, $C_{1-4}$-alkoxy, hydroxy, cyano, fluorine, chlorine and bromine, heterocyclyl, optionally substituted with 1–4 substituents selected from $C_{1-4}$-alkyl, $C_{1-4}$-alkoxy, hydroxy, cyano, fluorine, chlorine and bromine, and wherein said heterocycle is furyl, 1-pyrrolyl, 2-pyrrolyl, 1-thiophenyl, 2-thiophenyl, 2-pyridinyl (2-pyridyl), 3-pyridinyl (3-pyridyl), 4-pyridinyl (4-pyridyl), 1H-pyridin-2-one, 1H-pyridin-4-one, 3H-pyrimidine-4-one, pyridazine (1,2-diazine), pyrimidine (1,3-diazine), pyrazine (1,4-diazine), oxazole or isoxazole (iso-oxazole);

X is S or O;

or the pharmaceutically acceptable hydrolyzable esters or ethers thereof or pharmaceutically acceptable salts thereof.

2. The compound according to claim 1 wherein
$R^1$ is optionally substituted $C_{1-12}$-alkyl, $C_{3-8}$-cycloalkyl, aryl, heterocyclyl or $C_{1-4}$-alkyl substituted with phenyl, wherein the substituted $C_{1-12}$-alkyl is substituted with 1–5 fluorine substituents;

$R^2$ is phenyl substituted with 1–5 substituents selected from $C_{1-4}$-alkyl, $C_{1-4}$-alkoxy, fluorine, chlorine, bromine, cyano and nitro;

A' is a group selected from $CH_2$-(phenyl-$C_{1-4}$-alkoxy), $CH_2$-(pyridyl-$C_{1-4}$-alkoxy), $C_{1-4}$-alkyl substituted with unsubstituted aryl, aryl substituted with 1–5 substituents selected from $C_{1-4}$-alkyl, $C_{1-4}$-alkoxy, hydroxy, fluorine, chlorine, bromine, cyano, S—$C_{1-4}$-alkyl and NRR', unsubstituted 4-pyridyl or 4-pyridyl substituted with 1–4 substituents selected from $C_{1-4}$-alkyl, $C_{1-4}$-alkoxy, hydroxy, fluorine, chlorine, bromine, cyano, S—$C_{1-4}$-alkyl and NRR', wherein R and R' are independently of each other hydrogen or $C_{1-4}$-alkyl; or A' is a group of formula $CH_2$-U-heterocyclyl,
   wherein U is O, S or NR", wherein R" is hydrogen or $C_{1-4}$-alkyl, and
   wherein heterocyclyl is optionally substituted with 1–4 substituents selected from $C_{1-4}$-alkyl, fluorine, chlorine, bromine, cyano, nitro and NRR', wherein R and R' are independently of each other hydrogen or $C_{1-4}$-alkyl; or A' is a group of formula CH(OH)aryl; or A' is a group of formula CH=CHW
   wherein W is aryl substituted with 1–5 substituents selected from $C_{1-4}$-alkyl,
   $C_{1-4}$-alkoxy, hydroxy, cyano, fluorine, chlorine and bromine;

X is S or O.

3. The compound according to claim 1 wherein
$R^1$ is optionally substituted $C_{1-7}$-alkyl, $C_{3-8}$-cycloalkyl, aryl, heterocyclyl or $C_{1-4}$-alkyl substituted with optionally substituted phenyl, wherein the substituted $C_{1-7}$-alkyl is substituted with 1–3 fluorine substituents;

$R^{2'}$ is phenyl substituted with 1–3 substituents selected from $C_{1-4}$-alkyl, $C_{1-4}$-alkoxy, fluorine, chlorine, bromine, cyano and nitro;

$R^3$ is $C_{1-7}$-alkyl or $C_{1-4}$-alkoxy-$C_{1-2}$-alkyl;

A' is a group selected from $CH_2$-(phenyl-$C_{1-2}$-alkoxy), $CH_2$-(pyridyl-$C_{1-2}$-alkoxy), methyl substituted with unsubstituted phenyl, phenyl substituted with 1–3 substituents selected from $C_{1-4}$-alkyl, $C_{1-4}$-alkoxy, hydroxy, fluorine, chlorine, bromine, cyano, S—$C_{1-4}$-alkyl and NRR', unsubstituted 4-pyridyl or 4-pyridyl substituted with 1–2 substituents selected from $C_{1-4}$-alkyl, $C_{1-4}$-alkoxy, hydroxy, fluorine, chlorine, bromine, cyano, S—$C_{1-4}$-alkyl and NRR', wherein R and R' are independently of each other hydrogen or $C_{1-4}$-alkyl; or A' is a group of formula $CH_2$-U-heterocyclyl,
   wherein U is O, S or NR", wherein R" is hydrogen or $C_{1-4}$-alkyl, and
   wherein heterocyclyl is optionally substituted with 1–2 substituents selected from $C_{1-4}$-alkyl, fluorine, chlorine, bromine, cyano, nitro and NRR', wherein R and R' are independently of each other hydrogen or $C_{1-4}$-alkyl;

X is S or O.

4. The compounds according to claim 1 wherein
$R^1$ is optionally substituted $C_{1-7}$-alkyl, $C_{3-8}$-cycloalkyl, phenyl, pyridyl or benzyl, wherein the substituted $C_{1-7}$-alkyl is substituted with 1–3 fluorine substituents;

$R^{2'}$ is phenyl substituted with 1–3 substituents selected from $C_{1-2}$-alkyl, fluorine, chlorine and cyano;

$R^3$ is $C_{1-7}$-alkyl or $C_{1-2}$-alkoxy-$C_{1-2}$-alkyl; and

A' is a group selected from $CH_2$-(phenyl-$C_{1-2}$-alkoxy), $CH_2$-(pyridyl-$C_{1-2}$-alkoxy), methyl substituted with unsubstituted phenyl, phenyl substituted with 1–3 substituents selected from $C_{1-2}$-alkyl, $C_{1-2}$-alkoxy, hydroxy, fluorine, chlorine, bromine, cyano, S—$C_{1-2}$-alkyl and NRR', unsubstituted 4-pyridyl, or 4-pyridyl substituted with 1–2 substituents selected from $C_{1-2}$-alkyl, $C_{1-2}$-alkoxy, hydroxy, fluorine, chlorine, bromine, cyano, S—$C_{1-2}$-alkyl and NRR', wherein R and R' are independently of each other hydrogen or $C_{1-2}$-alkyl;

X is S or O.

5. The compound according to claim 1 wherein
$R^1$ is $C_{1-7}$-alkyl;

$R^{2'}$ is phenyl substituted with 1–3 substituents selected from chlorine and cyano;

$R^3$ is $C_{1-7}$-alkyl;

A' is a group selected from $CH_2$-(aryl-$C_{1-2}$-alkoxy), $CH_2$-(heterocyclyl-$C_{1-2}$-alkoxy), methyl substituted with optionally substituted 4-pyridyl, wherein the substituted 4-pyridyl is substituted with 1–2 substituents selected from $C_{1-2}$-alkyl, $C_{1-2}$-alkoxy, hydroxy, fluorine, chlorine, bromine, cyano, S—$C_{1-2}$-alkyl and NRR', wherein R and R' are independently of each other hydrogen or $C_{1-2}$-alkyl; and X is S or O.

6. The compound according to claim 1 wherein $R^1$ is $C_{1-4}$-alkyl;

$R^2$ is phenyl substituted with 1–3 chlorine substituents;

$R^3$ is $C_{1-4}$-alkyl;

A' is methyl substituted with optionally substituted 4-pyridyl, wherein the substituted 4-pyridyl is substituted with 1–2 substituents selected from $C_{1-2}$-alkyl and chlorine; and X is S or O.

7. The compound according to claim 1 wherein

A' is a group selected from $CH_2$-(aryl-$C_{1-4}$-alkylamino), $CH_2$-(aryl-$C_{1-4}$-alkoxy), $CH_2$-(heterocyclyl-$C_{1-4}$-alkoxy), $C_{1-4}$-alkyl substituted with optionally substituted aryl, wherein the substituted aryl is substituted with 1–5 substituents selected from $C_{1-4}$-alkyl, $C_{1-4}$-alkoxy, hydroxy, fluorine, chlorine, bromine, cyano, S—$C_{1-4}$-alkyl and NRR', wherein R and R' are independently of each other hydrogen or $C_{1-4}$-alkyl; or A' is a group of formula $CH_2$-U-heterocyclyl,
   wherein U is O, S or NR'', wherein R'' is hydrogen or $C_{1-4}$-alkyl, and
   wherein heterocyclyl is optionally substituted with 1–4 substituents selected from $C_{1-4}$-alkyl, fluorine, chlorine, bromine, cyano, nitro and NRR', wherein R and R' are independently of each other hydrogen or $C_{1-4}$-alkyl; or A' is a group of formula CH(OH)aryl; or A' is a group of formula CH=CHW
   wherein W is unsubstituted aryl, aryl substituted with 1–5 substituents selected from $C_{1-4}$-alkyl, $C_{1-4}$-alkoxy, hydroxy, cyano, fluorine, chlorine and bromine, unsubstituted heterocyclyl, or heterocyclyl substituted with 1–4 substituents selected from $C_{1-4}$-alkyl, $C_{1-4}$-alkoxy, hydroxy, cyano, fluorine, chlorine and bromine;

X is S or O;

or the pharmaceutically acceptable hydrolyzable esters or ethers thereof, and pharmaceutically acceptable salts thereof.

8. A compounds according to the formula

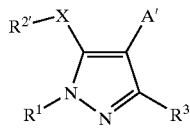

wherein $R^1$ is $C_{1-12}$-alkyl, $C_{3-8}$-cycloalkyl, acyl, $C_{1-4}$-alkylsulfonyl, optionally substituted phenylsulfonyl, aryl or $C_{1-4}$-alkyl substituted with phenyl or with phenyl is substituted with 1–5 substituents selected from $C_{1-4}$-alkyl, $C_{1-4}$-alkoxy, hydroxy, fluorine, chlorine or bromine;

$R^{2'}$ is phenyl or phenyl substituted with 1–5 substituents selected from $C_{1-4}$-alkyl, $C_{1-4}$-alkoxy, hydroxy, fluorine, chlorine or bromine;

$R^3$ is $C_{1-12}$-alkyl or $C_{1-4}$-alkoxy-$C_{1-4}$-alkyl;

A' is a group selected from $CH_2$-(aryl-$C_{1-4}$-alkylamino), $CH_2$-(aryl-$C_{1-4}$-alkoxy), $C_{1-4}$-alkyl substituted with unsubstituted aryl, aryl substituted with 1–5 substituents selected from $C_{1-4}$-alkyl, $C_{1-4}$-alkoxy, hydroxy, fluorine, chlorine and bromine, unsubstituted 4-pyridyl, or 4-pyridyl substituted with 1–4 substituents selected from $C_{1-4}$-alkyl, $C_{1-4}$-alkoxy, hydroxy, fluorine, chlorine and bromine; or A' is a group of formula CH(OH)Z'
   wherein Z' is aryl; or A' is a group of formula CH=CHW
   wherein W is unsubstituted aryl, aryl substituted with 1–5 substituents selected from $C_{1-4}$-alkyl, $C_{1-4}$-alkoxy, hydroxy, fluorine, chlorine and bromine, heterocyclyl optionally substituted with 1–4 substituents selected from $C_{1-4}$-alkyl, $C_{1-4}$-alkoxy, hydroxy, fluorine, chlorine and bromine, and wherein said heterocycle is furyl, 1-pyrrolyl, 2-pyrrolyl, 1-thiophenyl, 2-thiophenyl, 2-pyridinyl (2-pyridyl), 3-pyridinyl (3-pyridyl), 4-pyridinyl (4-pyridyl), 1H-pyridin-2-one, 1H-pyridin-4-one, 3H-pyrimidine-4-one, pyridazine (1,2-diazine), pyrimidine (1,3-diazine), pyrazine (1,4-diazine), oxazole or isoxazole (iso-oxazole);

X is S or O;

or the pharmaceutically acceptable hydrolyzable esters or ethers thereof, and pharmaceutically acceptable salts thereof.

9. The compound according to claim 1 wherein

X is S.

10. The compound according to claim 8 wherein X is S.

11. A pharmaceutical composition comprising a pharmaceutically effective amount of a compound according to claim 1 and a pharmaceutically inert carrier.

* * * * *